US012642861B2

(12) United States Patent
Verkade et al.

(10) Patent No.: US 12,642,861 B2
(45) **Date of Patent: *Jun. 2, 2026**

(54) ENEDIYNE CONJUGATES

(71) Applicant: SynAffix B.V., Oss (NL)

(72) Inventors: Jorge Merijn Mathieu Verkade, Eindhoven (NL); Jorin Hoogenboom, Wageningen (NL); Maria Antonia Van Berkel, Wijchen (NL); Floris Louis Van Delft, Nijmegen (NL)

(73) Assignee: SYNAFFIX B.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,887

(22) Filed: Jan. 9, 2023

(65) Prior Publication Data

US 2023/0346965 A1 Nov. 2, 2023

Related U.S. Application Data

(63) Continuation of application No. 16/894,602, filed on Jun. 5, 2020, now Pat. No. 11,547,763, which is a (Continued)

(30) Foreign Application Priority Data

Dec. 6, 2017 (EP) .................................... 17205712

(51) Int. Cl.
*A61K 47/68* (2017.01)
*C07K 16/32* (2006.01)

(52) U.S. Cl.
CPC ...... *A61K 47/6809* (2017.08); *A61K 47/6889* (2017.08); *C07K 16/32* (2013.01)

(58) Field of Classification Search
None
See application file for complete search history.

(56) References Cited

FOREIGN PATENT DOCUMENTS

| | | | |
|---|---|---|---|
| EP | 0 289 030 A2 | 11/1988 | |
| WO | WO-2014065661 A1 * | 5/2014 | ............ A61K 47/61 |

(Continued)

OTHER PUBLICATIONS

Jewett et al., Chem Soc Rev. Apr. 2010; 39(4): 1272-1279 (Year: 2010).*

(Continued)

*Primary Examiner* — Karl J Puttlitz
(74) *Attorney, Agent, or Firm* — Foley & Lardner LLP

(57) ABSTRACT

The invention relates to compounds of general structure (1): Q-$(L^1)_n$-$(L^2)_o$-$(L^3)_p$-$(L^4)_q$-D (1), wherein Q is a click probe; D is a cytotoxin containing an enediyne moiety; $L^1$, $L^2$, $L^3$ and $L^4$ are each individually linkers that together link Q to D; n, o, p and q are each individually 0 or 1, provided that n+o+p+q=1, 2, 3 or 4, wherein D comprises a functional moiety (21):

(21)

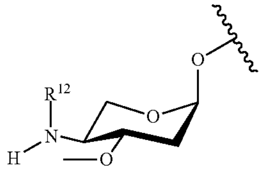

wherein $R^{12}$=$C_{1-3}$-alkyl, the wavy line indicates the connection to the remainder of the cytotoxin, and wherein D is conjugated to $(L^4)_q$ by replacing the amine H atom, and to conjugates obtainable by reacting the compound according to the invention with a protein comprising a click probe F capable of reacting with click probe Q in a click reaction. The invention further relates to a bioconjugate according to general structure (2): Pr-[$(L^6)$-Z-$(L^1)_n$-$(L^2)_o$-$(L^3)_p$-$(L^4)_q$-D]

(Continued)

$_{xx}$ (2), wherein Z is a connecting group that is formed in a click reaction, $L^6$ is a linker that links Z to Pr and Pr is a (glyco)protein.

16 Claims, 6 Drawing Sheets

Related U.S. Application Data continuation of application No. PCT/EP2018/083775, filed on Dec. 6, 2018.

(56) References Cited

FOREIGN PATENT DOCUMENTS

| | | | | | |
|---|---|---|---|---|---|
| WO | WO-2016/172273 | A1 | | 10/2016 | |
| WO | WO-2017137456 | A1 | * | 8/2017 | A61K 47/549 |
| WO | WO-2017137457 | A1 | * | 8/2017 | A61K 38/07 |
| WO | WO-2017172907 | A1 | * | 10/2017 | A61K 39/395 |
| WO | WO-2018/138591 | A1 | | 8/2018 | |

OTHER PUBLICATIONS

Brian H. Northrop et al: "Thiol-maleimide "click" chemistry: evaluating the influence of solvent, initiator, and thiolon the reaction mechanism, kinetics, and selectivity", Polymer Chemistry, vol. 6, No. 18, Jan. 1, 2015 (Jan. 1, 2015), pp. 3415-3430.

International Search Report mailed Mar. 1, 2019 in International Application No. PCT/EP2018/083775, 4 pages.

Jewett et al., "Cu-free click cycloaddition reactions in chemical biology", Chem Soc Rev, 2010, 39(4), (29 pages).

Jorge M. M. Verkade et al: "A Polar Sulfamide Spacer Significantly Enhances the Manufacturability, Stability, and Therapeutic Index of Antibody-Drug Conjugates", Antibodies, vol. 7, No. 1, Feb. 20, 2018 (Feb. 20, 2018), p. 12.

Kang et al., "Recent developments in chemical conjugation strategies targeting native amino acids in proteins and their applications in antibody-drug conjugates," Royal Society of Chemistry, Chemical Science, 2021, 12, 13613.

Nicolaou et al., "Chemistry and biology of natural and designed enediyndes," Proc. Natl. Acad. Sci. USA, vol. 90, pp. 5881-5888, Jul. 1993.

Zhong et al., "Problems and Solutions in Click Chemistry Applied to Drug Probes", Scientific Reports, 2016 (6 pages).

* cited by examiner

ENEDIYNE CONJUGATES

CROSS-REFERENCE TO RELATED APPLICATIONS

This application is a continuation of U.S. application Ser. No. 16/894,602, filed Jun. 5, 2020, which application is a continuation of International Application No. PCT/EP2018/083775, filed Dec. 6, 2018, which claims the benefit of and priority to European Application No. 17205712.7, filed Dec. 6, 2017, both of which are hereby incorporated by reference herein in their entireties.

FIELD OF THE INVENTION

The present invention is in the field of bioconjugation. More specifically, the invention relates to specific compounds that are useful for preparing bioconjugates, in particular antibody-drug conjugates (ADCs).

BACKGROUND

The enediynes represent one of the most fascinating families of natural products for their unprecedented molecular architecture and extraordinary biological activities. Since the neocarzinostatin (NCS) chromophore structure was first unveiled in 1985, the enediyne family has grown steadily to 11 structurally characterized members and 4 additional members isolated in their cycloaromatized form known to date. Classified into two subcategories according to the size of the enediyne core structures, members of the 9-membered enediyne subcategory include NCS, C-1027, kedarcidin (KED), maduropeptin (MDP), N1999A2, the sporolides (SPO), the cyanosporasides (CYA and CYN), and the fijiolides, with the latter four isolated in cycloaromatized form. Members of the 10-membered enediyne subcategory include the calicheamicins (CAL), the esperamicins (ESP), dynemicin (DYN), namenamicin, shishijimicin, and uncialamycin (UCM).

The enediynes have had a profound impact on modern chemistry, biology, and medicine. All enediynes contain a unit consisting of two acetylenic groups conjugated to a double bond or an incipient double bond within the 9- or 10-membered carbocycle. As a consequence of this structural feature, the enediynes share a mode of action: electronic rearrangement of the enediyne carbocycle produces a transient benzenoid diradical. When positioned within the minor groove of DNA, the diradical abstracts hydrogen atoms from the deoxyribose backbone of duplex DNA; the DNA-centered radicals can then cause interstrand cross-links (ICLs) or react with molecular oxygen, leading ultimately to DNA double-strand breaks, or both. With their exquisite mode of action and their extraordinary cytotoxicity, the enediynes have been successfully translated into clinical drugs. It is remarkable that, among the 11 enediynes known to date, two [NCS as poly(styrene-comaleic acid)-conjugated NCS (SMANCS) and calicheamicin as gemtuzumab ozogamicin (Mylotarg) and inotuzumab ozogamicin (Besponsa)] have been developed into marketed drugs, one (C-1027, also known as lidamycin) has been in phase II clinical trials, and several have been (esperamicin, dynemicin, kedarcidin) or still are (uncialamycin) in preclinical studies, representing an astonishing and remarkable success rate with the enediyne class of natural products.

Calicheamicin $\gamma_1^I$ (also known as LL-E33288) was discovered in the early 1980s, when it was isolated from bacteria residing on a chalky rock from a site near a Texas highway. Calicheamicin $\gamma_1^I$ was found to possess phenomenally high potency against tumor cells, which provided the impetus for its structure elucidation (see below), and consists of three domains: (1) an enediyne segment ("molecular warhead"), (2) a trisulfide moiety ("triggering device") and (3) an oligosaccharide chain ("recognition device").

Due to their unique mode of action and potency, several analogues of the calicheamicins have been tested in preclinical models as potential antitumor agents. Their development as single agent therapies has not been pursued, however, because of delayed toxicities that limit the therapeutic dose range for treatment. However, the potency of calicheamicins makes them ideal for antibody-targeted chemotherapy.

Antibody-targeted chemotherapy is known in the art, and consists of treatment of a cancer patient with a recombinant antibody covalently bound to a cytotoxic chemical via a synthetic linker (S. C. Alley et al, *Curr. Opin. Chem. Biol.* 2010, 14, 529-537). The main objective of an antibody-drug conjugate (ADC), also called immunotoxin, is to combine the high specificity of a monoclonal antibody for a tumor-associated antigen with the pharmacological potency of a "small" cytotoxic drug (typically 300 to 2,000 Da). Examples of ADCs include gemtuzumab ozogamicin (Mylotarg; anti-CD33 mAb conjugated to calicheamycin, Pfizer/Wyeth); brentuximab vedotin (SGN-35, Adcetris, a CD30-targeting ADC consisting of brentuximab, covalently linked to MMAE (monomethylauristatin E), Seattle Genetics); trastuzumab-DM1 conjugate (T-DM1). ADCs known from the prior art are commonly prepared by conjugation of the linker-toxin to the side chain of antibody amino acid lysine or cysteine, by acylation or alkylation, respectively. Some early generation ADCs were prepared by conjugation of a hydrazide derivative of the cytotoxic chemical to an oxidized glycan of the monoclonal antibody.

The first series of antibody conjugates of calicheamicin $\gamma_1^I$ were based on attachment to the anti-MUC1 antibody CTM01 via a hydrazone linkage to the oxidized antibody glycan as a site of hydrolytic release (see for example Hinman et al. *Cancer Res.* 1993, 53, 3336-3342). In addition, the original trisulfide moiety is replaced by a dimethylated, stabilized disulfide, which likely prevents the premature release of calicheamicin by circulating reduced thiols (e.g. glutathione). Thirdly, comparison of the therapeutic efficacy of several calicheamicin conjugates against the MX-1 xenograft tumor implanted in nude mice indicated that the therapeutic window was highest for the N-acetylated derivative of the calicheamicin core.

Further work on conjugates of the same anti-MUC1 antibody by Hamann et al. (*Bioconj. Chem.* 2005, 16, 346-353) showed that the "amide conjugate" which lacks the hydrazone site of hydrolysis was equivalent or superior to the amide-linker ADC in all preclinical models examined, especially against resistant cell lines. On the basis of these findings, an amide-linked ADC with calicheamicin payload (CMB-401) was clinically evaluated for the treatment of recurrent platinum-sensitive epithelial ovarian carcinoma (EOC) but was discontinued after a phase II study did not meet its end-point (see for example Chan et al. *Canc. Immunol. Immunother.* 2003, 52, 243-248).

In contrast to the CMT01-conjugate, it was found by Hamann et al. (*Bioconj. Chem.* 2002, 13, 40-46) that ADCs based on the anti-CD33 murine antibody P67.6 showed a clear benefit for a hydrolytic release mechanism of the calicheamicin derivative, as afforded by the hydrazone conjugate, versus the non-cleavable amide conjugate, in terms of beneficial potency and selectivity in vitro, in vivo, and ex vivo. As a consequence, the P67.6-calicheamicin hydrazone conjugate was a priori selected for application in development of an ADC against acute myeloid leukemia (AML). However, it was later reported by the same authors (Hamann et al., *Bioconj. Chem.* 2002, 13, 47-58) that the humanized version of P67.6 was not suitable to make hydrazone conjugates because of unexpected sensitivity of the antibody to periodate oxidation. A series of bifunctional linkers was therefore developed, resulting in a new class of 'hybrid' conjugates, combining stable attachment of the calicheamicin to lysines but with the hydrazone incorporated in the linker as a site of hydrolytic release. The optimized conjugate chosen for clinical trials, CMA-676, was found to be significantly more potent and selective than the carbohydrate conjugate it replaced. In clinical trials, CMA-676 selectively inhibited leukemia colony formation by marrow cells from a significant proportion of AML patients and became the first antibody-targeted chemotherapeutic agent approved by the FDA in 2000, gemtuzumab ozogamicin (Mylotarg®), for older patients with CD33-positive AML who had experienced a relapse (Stasi, *Expert Opin. Biol. Ther.* 2008, 8, 527-540).

However, in a post-approval study it was found that gemtuzumab ozogamicin in combination with chemotherapy did not demonstrate improved survival but instead showed a higher rate of toxicity than chemotherapy alone, leading to a high number of early deaths and then the voluntary withdrawal of this ADC from the market by Pfizer in 2010. Nevertheless, Mylotarg® remained in clinical use under 'compassionate use' regulation, during which studies it was observed that a treatment regimen based on fractionated dosing outweighed the risks and afforded significant clinical benefit. Based on these observations, Mylotarg® was resubmitted to FDA to receive approval again on Sep. 1, 2017. Better then with the first approval, clinical indication this time included adults not only with refractory, but also with newly diagnosed acute CD33-positive AML.

Just two weeks earlier, on Aug. 17, 2017, FDA approved another ADC, Besponsa®, for treatment of adults with relapsed or refractory acute lymphoblastic leukemia (ALL). Besponsa® (inotuzomab ozogamicin) is composed of a CD22-targeting monoclonal antibody (G544) conjugated to identical linker-calicheamicin format as present in Mylotarg®.

An alternative cleavable linker to acid-sensitive hydrazone is disclosed in WO2016/172273, based on well-established dipeptide cathepsin-sensitive substrate. In addition, conjugation technology for attachment of calicheamicin to the monoclonal antibody is changed from amide bond (with lysine side-chains) to maleimide (with cysteine side-chains), and other mainstream conjugation technologies suggested. Also in WO2016/172273, N-acetylcalicheamicin $\gamma_1^I$ (R=Ac) is used throughout as the calicheamicin derivative of choice, although unmodified calicheamicin $\gamma_1^I$ (R=H) and a large number of other acylated derivatives at the N-ethyl sugar component are also claimed.

Lee et al. (*J. Am. Chem. Soc.* 1987, 109, 3464-3466 and *J. Am. Chem. Soc.* 1992, 114, 985-997), as part of their efforts to elucidate the structure of the calicheamicin antibiotics, were the first to report on the N-acetylated version of calicheamicin $\gamma_1^I$. Specifically, it was shown that treatment of a methanolic solution of calicheamicin $\gamma_1^I$ with a large excess of acetic anhydride (varying from 50 to >100 equivalents) for 3-4 hours affords N-acetylcalicheamicin $\gamma_1^I$ after concentration and purification. A similar procedure is disclosed in EP0392376, as well as two specific other acylated derivatives of calicheamicin $\gamma_1^I$, i.e. formyl- and N-monomethylsuccinyl calicheamicin $\gamma_1^I$. N-formylcalicheamicin $\gamma_1^I$ was obtained by a similar procedure as N-acetylcalicheamicin $\gamma_1^I$, i.e. using large excess of highly reactive mixed anhydride of formic acid and acetic acid, properly characterized and subjected to in vitro evaluation studies. Synthesis of the N-monomethylsuccinylcalicheamicin $\gamma_1^I$ derivative is described by stirring of methanolic solution of calicheamicin $\gamma_1^I$ with 28 equivalents of the anhydride of succinic acid monomethyl ester for 3 days. Next, concentration and trituration of a 'gummy precipitate' was followed by precipitation from a mixture of ethyl acetate/diethyl ether/hexane, to afford the crude N-monomethylsuccinylacetyl calicheamicin $\gamma_1^I$, which was not further analyzed or evaluated.

In a similar approach, it is demonstrated in EP0289030 that esperamicin, an enediyne antibiotic with a structure highly resembling calicheamicin, can be efficiently acetylated by stirring with 40 equivalents of acetic anhydride for 48 h or with 30 equivalents for 16 h at 30° C.

These examples demonstrate that acylation of enediyne antibiotics having an N-alkylsugar in their structure, and calicheamicins in particular, can be achieved by treatment with excess of a small and highly reactive anhydride reagent like acetic anhydride or formic/acetic mixed anhydride.

While until recently all calicheamicin-based ADCs were obtained by an exchange reaction of the trisulfide moiety, Bernt et al. (Bioconj. Chem. 2009, 20, 1587-1594) for the first time describe how a specific calicheamicin derivative, calicheamicin Θ, can be connected to an anti-CD19 antibody through the N-ethyl sugar at the other end of the molecule. To this end, a pyridiyldisulfide linker containing an N-hydroxysuccinimide ester (2 equivalents) and dimethylaminopyridine (not quantified) as catalyst in DMSO, is reacted with calicheamicin Θ by stirring for 6 h at 0° C. Without further purification, the resulting mixture is added to the sulfhydryl-modified anti-CD19 antibody in PBS buffer, to generate an ADC with average two (2) molecules of calicheamicin Θ per antibody, as determined by absorption spectroscopy (analytical method not specified). Consecutive in vitro cytotoxicity determination as well as an in vivo xenograft study suggest a beneficial therapeutic effect for the anti-CD19-calicheamicin Θ conjugate, however given the lack of analytical data on the ADC it cannot be concluded whether this effect is due to the anticipated conjugation through the N-ethyl sugar or through any of the free alcohol functions of calicheamicin Θ (5 in total), given the well-established procedure for the formation of an ester by treatment of an alcohol with an activated ester in the presence of DMAP. In addition, given the lack of experimental verification, it cannot be excluded that in vitro and in vivo response is the result of the combination of naked anti-CD19 and free calicheamicin Θ.

In WO2017172907, it is disclosed how calicheamicin $\gamma_1^I$ can be connected through its N-ethylaminosugar to either cysteine or lysine side chains of a monoclonal antibody. To this end, calicheamicin $\gamma_1^I$ is reacted with an active ester or carbonate, leading to an amide or carbamate derivative at the N-ethylaminosugar, which is then further modified to give a construct containing a specific cleavable linker (oligopeptide, Val-Cit-PABC or Val-Ala-PABC) and a reactive moiety at the other end (maleimide, ortho-bishaloalkylaromatic molecules or active esters), for conjugation to cysteine or lysine. Another optional modification of calicheamicin $\gamma_1^I$ as described in WO2017172907 involves the exchange of the trisulfide moiety to a functionalized or isopropyl disulfide, by means of a well-known procedure involving treatment with excess of a mercaptan. By introduction of a mercaptan containing a hydrophilic group (further containing an alcohol group, a sulfonate group, or a carbohydrate group) it is suggested that the resulting ADCs display improved solubility in aqueous buffer and mitigate the issue of aggregation. In addition, a sterically hindered disulfide moiety instead of the natural trisulfide of calicheamicin improves stability of the payload in vivo. However, multiple synthetic steps are in all cases required to reach from calicheamicin $\gamma_1^I$ to the reactive derivative suitable for conjugation with antibody.

The advantage of the extremely high potency of enediyne antibiotics offers a considerable potential for incorporation into antibody-drug conjugates and therefore a benefit for patients. However, the manufacturing and handling of these highly potent active ingredients also potentially poses occupational risk for workers, even at very low airborne concentrations. As a result, safe handling systems to protect a healthy workforce against the adverse effects of these materials are routinely used by (bio)pharmaceutical manufacturing companies, such as containment devices with transfer chambers and airlocks, and with careful monitoring of airborne drug concentration. One effective way to reduce the occupational risk of workers in pharmaceutical manufacturing is to reduce the number of synthetic steps with the highly potent ingredient.

Besides direct conjugation of toxic payload through acylation of lysine (as applied in Mylotarg, Besponsa and Kadcyla) or alkylation of cysteine (as applied in Adcetris), a promising alternative approach to prepare antibody-drug conjugates involves the generation or functionalization of a monoclonal antibody with a so-called click probe to undergo attachment of toxic payload by click reaction in the second step. Typically, the click reaction will involve a [3+2] or [4+2] cycloaddition between two functional groups, such as strained cycloalkyne groups, terminal alkyne groups, azido groups, tetrazine groups and strained cycloalkene groups.

A well-known click reaction is the 1,3-dipolar cycloaddition of an azide with an alkyne group to form a stable triazole. The 1,3-dipolar cycloaddition can be performed between an azide and a terminal acetylene group in the present of copper(I). Alternatively, the 1,3-dipolar cycloaddition of azide can be performed in the absence of copper(I) if a strained (hetero)cycloalkyne is employed, in particular a (hetero)cyclooctyne. Well-known examples of (hetero) cyclooctynes used for metal-free click chemistry are difluorinated cyclooctyne (DIFO), benzoannulated cyclooctyne (DIBO, DIBAC, BARAC and COMBO) or cyclooctyne fused with a cyclopropane ring (BCN). With these strained alkynes, 1,3-dipolar cycloaddition also takes place with other 1,3-dipoles such as nitrones, nitrile oxides and diazo compounds.

Another well-known class of click reactions involve the Diels-Alder cycloaddition of an electron-poor aromatic moiety (such as a tetrazine, a triazine or a 1,2-orthoquinone) with a strained alkene or strained alkyne. Most prominently, the cycloaddition of a tetrazine with a strained alkene is employed because of its exceptionally high reaction rate. Most common tetrazines in this regard are (functionalized) 3-phenyltetrazine, 3,6-diphenyltetrazine or 3,6-dipyridyltetrazines. Most common strained alkenes involve (functionalized) methylcyclopropene or trans-cyclooctene (TCO), as well as variants thereof.

In order to prepare an antibody-drug conjugate by means of a click chemistry reaction, one (or more) click chemistry probe(s) must be installed onto the monoclonal antibody and the mutually reactive probe onto the toxic payload. The latter molecule can be readily prepared by chemical procedures known in the art. Installment of a click probe onto a monoclonal antibody can be achieved in a variety of manners, as for example summarized in Aggerwal et al. (*Bioconj. Chem.* 2015, 26, 176-192), including (a) direct chemical conjugation, (b) genetic encoding of a particular amino acid (or peptide sequence) followed by installation of click probe through this particular amino acid (or peptide sequence), (c) genetic encoding or incorporation by auxotrophic organism of a non-natural amino acid already harboring a click probe and (d) direct enzymatic modification of the monoclonal antibody.

One of the oldest and most versatile methods for antibody modification is through lysine conjugation, due to solvent accessibility and the high abundance of these residues on a protein surface. In general, this is achieved through the formation of an amide bond between a lysine residue and activated esters, such as N-hydroxysuccinimide (NHS), pentafluorophenol, or 4-sulfotetrafluorophenyl esters. An alternatively chemical approach for antibody conjugation involves treatment of antibody with mild reducing agent such as TCEP, followed by alkylation of liberated thiol groups with a suitable electrophilic reagent such as a maleimide, 1,2-bisbromomaleimide, 1,2-bisbromopyridazinedione, 1,2-bisbromomethylbenzene or bissulfone reagents, as summarized in Dovgan et al. *Bioconj. Chem.* 2017, 28, 1452-1457. Obviously, either method of lysine acylation or cysteine alkylation is highly suitable for installation of a click probe onto the antibody if already present in the electrophilic reagent. For example, Dovgan et al. show how treatment of a monoclonal antibody with 4-azidobenzoyl fluoride leads to efficient acylation of lysine residues in a PBS buffer, suitable for installation of toxic payload by copper-free click conjugation with BCN-modified monomethylauristatin E (MMAE). Another example is provided by Maruani et al. (*Nat. Communications* 2015, DOI: 10.1038/ncomms7645) for installation of alkyne group onto monoclonal antibodies by partial reduction followed by treatment with a suitably functionalized 1,2-bisbromopyridazinedione.

In order to achieve better control of conjugation site, monoclonal antibodies can be genetically modified with a specific additional cysteine, which can be chemoselectively modified after recombinant expression (Junutula et al. *Nat. Biotechnol.* 2008, 26, 925-932). Alternatively, a designed peptide tag can be installed into the monoclonal antibody for enzymatic modification. The latter types of enzymatic tagging methods include for example biotin ligase, transglutaminase, and lipoic acid ligase, as summarized by Aggerwal et al. (*Bioconj. Chem.* 2015, 26, 176-192).

Methods for genetic encoding of non-natural amino acids by ribosomal incorporation into proteins are well-known in the art and provide an elegant solution to the problem of site-specific engineering of functionality into a protein. In the most widely used method for non-natural amino acid incorporation, a mutant protein encoded by a gene with the amber stop codon (TAG) at the site of the desired non-natural amino acid is expressed in cells, along with a corresponding orthogonal tRNA/aminoacyl-tRNA synthetase (aaRS) pair capable of installing the non-natural amino acid at the amber stop codon site. Genetic encoding has inter alia been employed for installation of azide, tetrazine, cyclooctyne, cyclopropene or trans-cyclooctene moieties onto proteins. Another method to introduce a non-natural amino acid into a protein involves the metabolic incorporation of a non-natural amino acid, for example azidohomoalanine, instead of a natural amino acid, by an auxotrophic organism.

The fourth method of modification of antibodies with a click probe involves the enzymatic modification at a specific site. For example, it has been shown by Dennler et al. (*Bioconj. Chem.* 2014, 25, 569-578) that enzymatic deglycosylation at N297 of trastuzumab liberates a specific glutamine residue (N295) for modification with transglutaminase, thereby enabling the installation of an azide moiety. A similar strategy was employed by van Geel et al. (*Bioconj. Chem.* 2015, 26, 2233-2242), involving trimming of antibody glycan with an endoglycosidase, thereby liberating the core N-acetylglucosamine for enzymatic installation of an azidosugar under the action of a glycosyl transferase.

Hydrophobic interaction chromatography (HIC) is a non-denaturing liquid chromatography method that separates proteins based on their affinity to a hydrophobic stationary phase. ADCs typically have a rightward shift of the major peak as compared to their corresponding naked mAb due to the hydrophobicity of the payload, and ADCs with a higher DAR therefore have a longer HIC retention time, reflecting greater hydrophobic character. It has been demonstrated that in order to interact with the HIC stationary phase, the linker-payload must be able to reach out into bulk solvent. Therefore, the HIC retention of ADCs may be a crude method of comparing the steric accessibility of the linker-payload toward metabolic enzymes (see for example Tumey et al., *ACS Med. Chem. Lett.* 2016, 7, 977-982). In addition, pharmacokinetics of ADCs are inversely correlated to ADC hydrophobicity, therefore ADCs with longer HIC retention times are cleared faster (see for example Lyon et al, *Nat. Biotechn.* 2015, 33, 733-736 and Tumey et al., *AAPS J.,* 2017, 19, 1123-1135). As convenient measure to predict the pharmacokinetics of a given ADC is therefore by calculation of a HIC relative retention time (rrt), by dividing the absolute retention time of the ADC by the retention time of a mAb reference standard (unmodified antibody). Thus, small relative retention times (up to ~1.3) reflect a relatively non-hydrophobic ADC with pharmacokinetics likely not significantly altered from the that of the naked antibody.

Another important ADC attribute is aggregation. The increase in susceptibility of ADCs to aggregation could directly affect thermal stability and serum half-life and therefore impact manufacturing, storage and in vivo performance (efficacy, toxicity, and immune reaction of patients). Therefore, it is essential to keep aggregation propensity level low.

SUMMARY OF THE INVENTION

We here describe for the first time enediyne derivatives harboring at their alkylaminosugar a reactive moiety suitable to undergo click chemistry conjugation with a monoclonal antibody, which was demonstrated to be particularly suitable for the generation of site-specific and stable ADCs. The required click-probe and cleavable linker-functionalized enediyene derivatives were either prepared in a multistep sequence or preferably obtained in a single acylation step from the enediyne or its N-aminoacylated derivative, thereby significantly simplifying the synthetic process. In addition, by incorporation of a specific acylsulfamide functionality in the linker between the click probe and enediyne, aggregation of the ADC is reduced and pharmacokinetics improved. Further improvement of stability and PK can be achieved by a tri- to disulfide exchange with a mercaptan containing a hydrophilic group, prior to or after modification of the enediyne at its alkylaminosugar.

The invention in its key aspects relates to compounds of general structure (1): Q-$(L^1)_n$-$(L^2)_o$-$(L^3)_p$-$(L^4)_q$-D (1), wherein Q is a click probe; D is a cytotoxin containing an enediyne moiety; $L^1$, $L^2$, $L^3$ and $L^4$ are each individually linkers that together link Q to D; n, o, p and q are each individually 0 or 1, provided that n+o+p+q=1, 2, 3 or 4, wherein D comprises a functional moiety (21):

(21)

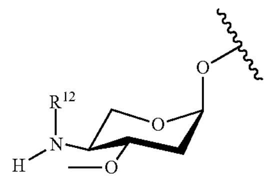

wherein $R^{12}$=$C_{1-3}$-alkyl, the wavy line indicates the connection to the remainder of the cytotoxin, and wherein D is conjugated to $(L^4)_q$ by replacing the amine H atom, and to conjugates obtainable by reacting the compound according to the invention with a protein comprising a click probe F capable of reacting with click probe Q in a click reaction. The invention further relates to a bioconjugate according to general structure (2): Pr-[$(L^6)$-Z-$(L^1)_n$-$(L^2)_o$-$(L^3)_p$-$(L^4)_q$-D]$_{xx}$ (2), wherein Z is a connecting group that is formed in a click reaction, $L^6$ is a linker that links Z to Pr and Pr is a protein and xx is an integer in the range 1-8, preferably in the range 2-8.

DETAILED DESCRIPTION OF THE INVENTION

Definitions

Figure 1:
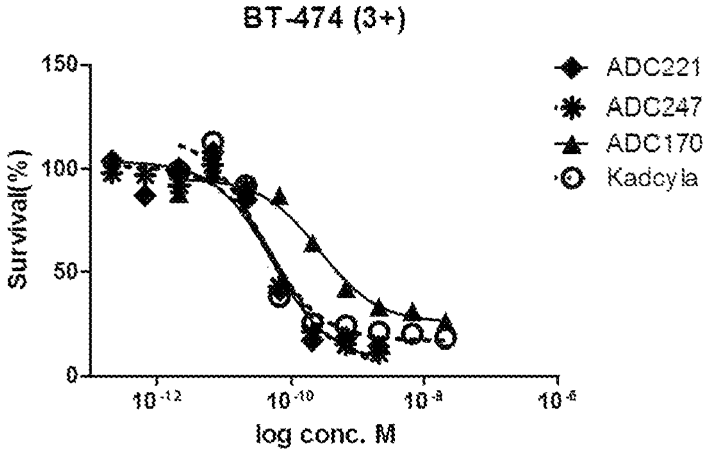
FIG. 1 shows the in vitro cytotoxicity plots for calicheamicin-based ADCs ADC170, ADC221, ADC247 and Kadcyla® on HER2 3+-positive BT-474 cell lines.
Figure 2A:
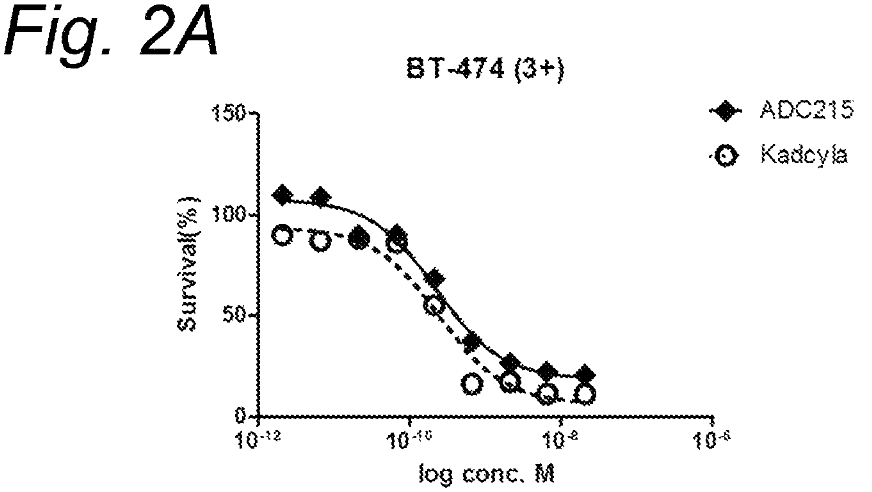
FIG. 2A shows the in vitro cytotoxicity plots for calicheamicin-based ADC215 and Kadcyla® on HER2 3+-positive BT-474 cell lines.
Figure 2B:
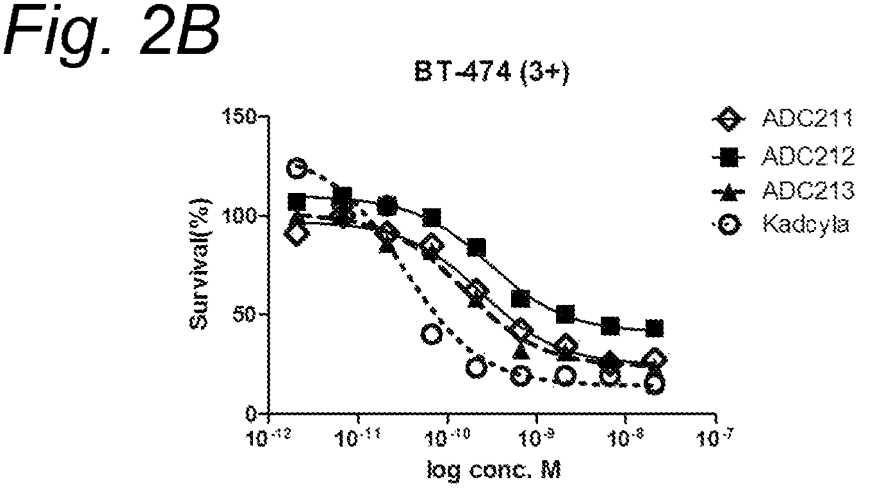
FIG. 2B shows the in vitro cytotoxicity plots for calicheamicin-based ADC211-213 and Kadcyla® on HER2 3+-positive BT-474 cell lines.
Figure 2C:
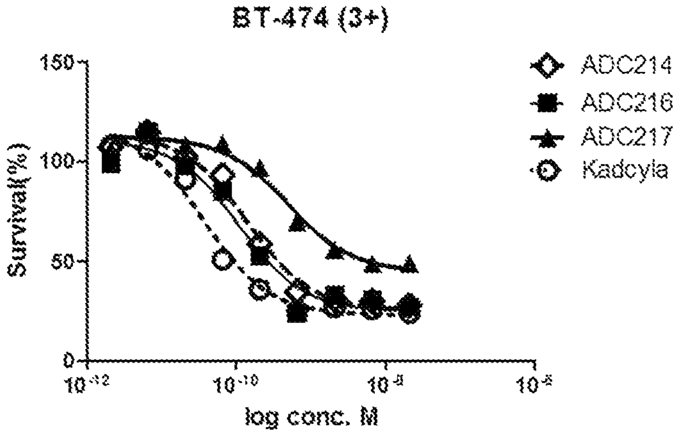
FIG. 2C shows the in vitro cytotoxicity plots for calicheamicin-based ADC214, ADC216 and ADC217 and Kadcyla® on HER2 3+-positive BT-474 cell lines.
Figure 2D:
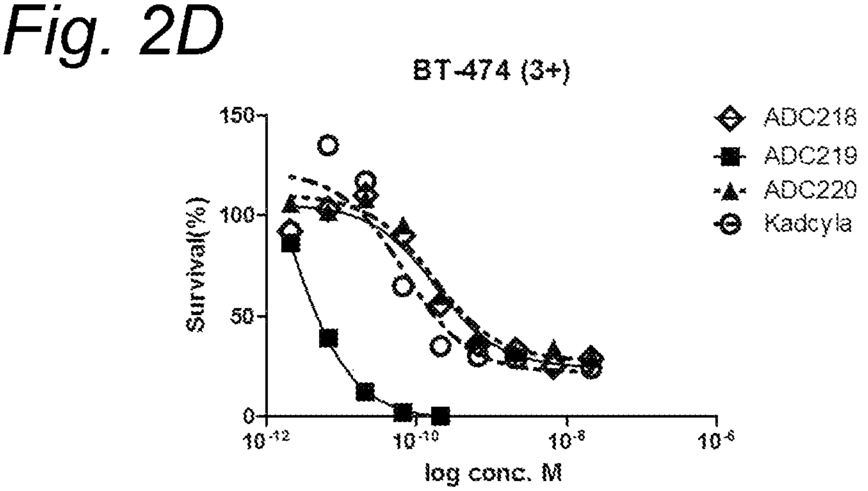
FIG. 2D shows the in vitro cytotoxicity plots for calicheamicin-based ADC218-220 and Kadcyla® on HER2 3+-positive BT-474 cell lines.
Figure 2E:
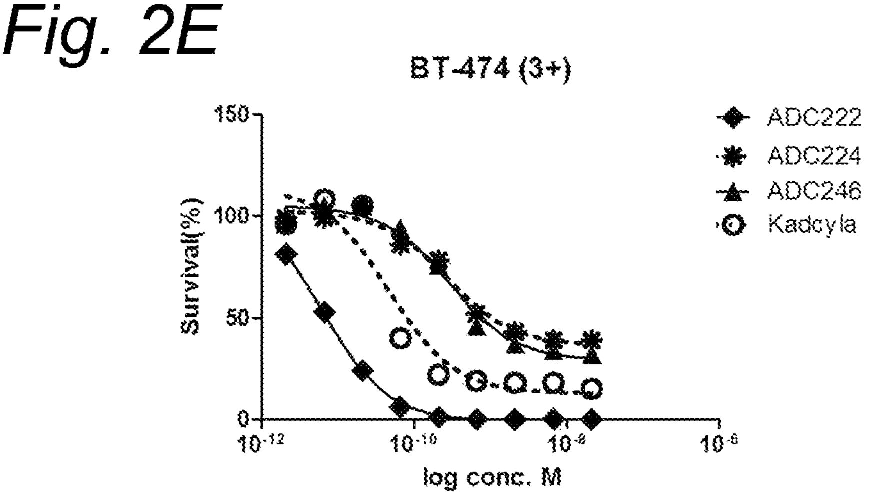
FIG. 2E shows the in vitro cytotoxicity plots for calicheamicin-based ADC222, ADC224 and ADC246 FIG. 2E), and Kadcyla® on HER2 3+-positive BT-474 cell lines.

The verbs "to comprise" and "to contain", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (candida antartica lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, $F(ab')_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

A linker is herein defined as a moiety that connects (covalently links) two or more elements of a compound. A linker may comprise one or more spacer moieties. A spacer-moiety is herein defined as a moiety that spaces (i.e. provides distance between) and covalently links together two (or more) parts of a linker. The linker may be part of e.g. a linker-construct, a linker-conjugate or a bioconjugate, as defined below.

A "hydrophilic group" or "polar linker" is herein defined as any molecular structure containing one or more polar functional groups that imparts improved polarity, and therefore improved aqueous solubility, to the molecule it is attached too. Preferred hydrophilic groups are selected from a carboxylic acid group, an alcohol group, an ether group, a polyethylene glycol group, an amino group, an ammonium group, a sulfonate group, a phosphate group, an acyl sulfamide group or a carbamoyl sulfamide group. In addition to higher solubility other effects of the hydrophilic group include improved click conjugation efficiency, and, once incorporated into an antibody-drug conjugate: less aggregation, improved pharmacokinetics resulting in higher efficacy and in vivo tolerability.

The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt. The term "pharmaceutically accepted" salt means a salt that is acceptable for administration to a patient, such as a mammal (salts with counterions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

The term "enediyne" refers to any cytotoxin characterized by the presence of a 3-ene-1,5-diyne structural feature as part of a cyclic molecule as known in the art and include neocarzinostatin (NCS), C-1027, kedarcidin (KED), maduropeptin (MDP), N1999A2, the sporolides (SPO), the cyanosporasides (CYA and CYN), and the fijiolides, calicheamicins (CAL), the esperamicins (ESP), dynemicin (DYN), namenamicin, shishijimicin, and uncialamycin (UCM).

The term "alkylaminosugar" as used herein means a tetrahydropyranyl moiety connected to an alcohol function via its 2-position, thereby forming an acetal function, and further substituted by (at least) one N-alkylamino group in position 3, 4 or 5. "N-alkylamino group" in this context refers to an amino group having one methyl, ethyl or 2-propyl group.

The term "click probe" refers to a functional moiety that is capable of undergoing a click reaction, i.e. two compatible click probes mutually undergo a click reaction such that they are covalently linked in the product. Compatible probes for click reactions are known in the art, and preferably include (cyclic) alkynes and azides. In the context of the present invention, click probe Q in the compound according to the invention is capable of reacting with click probe F on the (modified) protein, such that upon the occurrence of a click reaction, a conjugate is formed wherein the protein is conjugated to the compound according to the invention. Herein, F and Q are compatible click probes.

An "acylsulfamide moiety" is herein defined as a sulfamide moiety ($H_2NSO_2NH_2$) that is N-acylated or N-carbamoylated on one end of the molecule and N-alkylated (mono or bis) at the other end of the molecule.

ASPECTS OF THE INVENTION

In one aspect, the invention concerns compounds of general structure (1)

$$Q—(L^1)_n—(L^2)_o—(L^3)_p—(L^4)_q—D \quad (1)$$

wherein:

Q is a click probe;

D is a cytotoxin containing an enediyne moiety as further defined here below;

$L^1$, $L^2$, $L^3$ and $L^4$ are linkers that together link Q to D as further defined here below;

n, o, p and q are individually 0 or 1, provided that n+o+p+q=1, 2, 3 or 4.

Also contemplated within the first aspect of the invention are salts, preferably pharmaceutically acceptable salts, of the compound according to structure (1).

In one aspect, the invention concerns a process for synthesising a compound according to general structure (1), comprising acylation of D through its N-alkylaminosugar with an activated carbonate form of Q-$(L^1)_n$ or Q-$(L^1)_n$-$(L^2)_o$-$(L^3)_p$ such as a p-nitrophenylcarbonate or N-hydroxysuccinimidyl carbonate derivative.

In another aspect, the invention concerns a process for synthesising a compound according to general structure (1), comprising acylation of D through its N-alkylaminosugar with an activated ester form of Q-$(L^1)_n$-$(L^4)_q$ or Q-$(L^1)_n$-$(L^2)_o$-$(L^3)_p$-$(L^4)_q$ such as a chloro, a p-nitrophenylcarbonate or N-hydroxysuccinimidyl ester derivative.

In yet another aspect, the invention concerns a process for synthesising a compound according to general structure (1), comprising acylation of D through its N-alkylaminosugar with an N-protected and activated ester form of $(L^4)_q$ followed by N-deprotection and acylation with an activated carbonate form of Q-$(L^1)_n$ or Q-$(L^1)_n$-$(L^2)_o$-$(L^3)_p$ such as a p-nitrophenylcarbonate or N-hydroxysuccinimidyl carbonate derivative.

In one aspect, the invention concerns a process for preparing a protein-conjugate, comprising reacting the compound according to general structure (1) with a modified protein comprising a click probe F which is capable of reacting with click probe Q in a click reaction. In this reaction, a conjugate according to formula (2) is formed:

$$Pr—[(L^6—Z—(L^1)_n—(L^2)_o—(L^3)_p—(L^4)_q—D]_{xx} \quad (2)$$

wherein $L^1$, $L^2$, $L^3$, $L^4$, D, n, o, p and q are as defined above for the compound according to the invention; Z is a connecting group comprising a moiety that is obtained in a click reaction between Q and F, preferably Z contains a triazole moiety; $L^6$ is a linker that links Z to Pr; and Pr is a protein, preferably a glycoprotein, most preferably an antibody and xx is an integer in the range 1-8, preferably in the range 2-8.

The inventions further concerns the bioconjugate thus obtained and the medical use thereof.

Compound of General Structure (1)

In one aspect, the invention concerns compounds of general structure (1)

$$Q-(L^1)_n-(L^2)_o-(L^3)_p-(L^4)_q-D \quad (1)$$

wherein:

Q is a click probe;

D is a cytotoxin containing an enediyne moiety as further defined here below;

$L^1$, $L^2$, $L^3$ and $L^4$ are linkers that together link Q to D as further defined here below;

n, o, p and q are individually 0 or 1, provided that n+o+p+q=1, 2, 3 or 4.

Click Probe Q

Q represents a click probe. Click probes are herein defined as moieties that comprise a reactive group that is capable of undergoing a click reaction, defined herein as a (2+3) or (2+4) cycloaddition between two functional groups, thereby forming a stable covalent bond, that show high mutual reactivity but at the same time low reactivity for natural biomolecular functionality, such as those present in proteins, nucleic acids, glycans and lipids. Moreover, a click reaction as defined herein can be performed in (nearly) every solvent of choice, including water (and buffered systems thereof), DMSO, DMA, DMF and propylene glycol. Suitable reactive groups include strained cycloalkyne groups, terminal alkyne groups, azido groups, tetrazine groups and strained cycloalkene groups.

The most preferred click reaction in the context of the present invention is the 1,3-dipolar cycloaddition, wherein an 1,3-dipole is reacted with a dipolarophile. Q can either be the dipole or the dipolarophile, although it is preferred that Q is the dipolarophile. The preferred dipole is an azido group. The preferred dipolarophile is an alkyne group. In one preferred embodiment, the reactive group comprises an alkyne moiety or an azide moiety.

In case Q comprises an alkyne moiety, Q is preferably selected from a terminal alkyne and a (hetero)cycloalkyne. Preferably, Q comprises a (hetero)cyclooctyne moiety, most preferably Q comprises a cyclooctyne moiety, i.e. a moiety according to structure (9a) below. Herein, the alkynes and (hetero)cycloakynes may optionally be substituted.

In a preferred embodiment, Q is an alkynyl group, wherein the alkynyl group is linear or branched, and wherein the alkynyl group is optionally substituted. Preferably, the alkynyl group is a terminal alkynyl group. Preferably said alkynyl group is a $C_2$-$C_{24}$ alkynyl group, more preferably a $C_2$-$C_{12}$ alkynyl group, and even more preferably a $C_2$-$C_6$ alkynyl group. More preferably, the alkynyl group is according to structure (9b) below. Herein, l is an integer in the range of 0 to 10, preferably in the range of 0 to 6. More preferably, l is 0, 1, 2, 3 or 4, more preferably l is 0, 1 or 2 and most preferably l is 0 or 1.

In another preferred embodiment, Q is a (hetero)cycloalkynyl group. The (hetero)cycloalkynyl group is optionally substituted. Preferably, the (hetero)cycloalkynyl group is a (hetero)cyclooctynyl group, i.e. a heterocyclooctynyl group or a cyclooctynyl group, wherein the (hetero)cyclooctynyl group is optionally substituted. In a further preferred embodiment, the (hetero)cyclooctynyl group is according to formula (9c), also referred to as a DIBO group, (9d), also referred to as a BARAC group or (9e), also referred to as a DIBAC or DBCO group, all as shown below, wherein U is O or $NR^9$. Herein, $R^9$ is selected from the group consisting of hydrogen, a linear or branched $C_1$-$C_{12}$ alkyl group or a $C_4$-$C_{12}$ (hetero)aryl group. Preferably, $R^9$ is hydrogen or a $C_1$-$C_6$ alkyl group, more preferably $R^9$ is hydrogen or a $C_1$-$C_4$ alkyl group. Even more preferably $R^9$ is hydrogen or methyl, ethyl, n-propyl, i-propyl, n-butyl, s-butyl or t-butyl. Most preferably $R^9$ is hydrogen or methyl. The aromatic rings in (9c) are optionally O-sulfonylated at one or more positions, whereas the rings of (9d) and (9e) may be halogenated at one or more positions. For Q=(9c), the moiety U may overlap with the terminal moiety of the linker $(L^1)_n$-$(L^2)_o$-$(L^3)_p$-$(L^4)_q$, typically of linker $L^1$, such that it is only present once. In other words, moiety U may be absent from Q=(9c) in case the linker comprises a moiety U directly connected to Q. For Q=(9e), the C(O) moiety may overlap with the terminal moiety of the linker $(L^1)_n$-$(L^2)_o$-$(L^3)_p$-$(L^4)_q$, typically of linker $L^1$, such that it is only present once. In other words, the C(O) moiety may be absent from Q=(9e) in case the linker comprises a C(O) moiety directly connected to Q.

In another preferred embodiment, Q is an, optionally substituted, bicyclo[6.1.0]non-4-yn-9-yl] group, also referred to as a BCN group. Preferably, the bicyclo[6.1.0]non-4-yn-9-yl] group is according to formula (9f) as shown below, wherein V is $-(CH_2)_l$ and l is an integer in the range of 0 to 10, preferably in the range of 0 to 6. More preferably, l is 0, 1, 2, 3 or 4, more preferably l is 0, 1 or 2 and most preferably l is 0 or 1. In the context of group (9f), l is most preferably 1.

In another preferred embodiment, Q is an optionally substituted tetrazinyl group, more preferably, said tetrazinyl group is according to formula (9g), as shown below, wherein $R^{18}$ is selected from the group consisting of hydrogen, a linear or branched $C_1$-$C_{12}$ alkyl group or a $C_4$-$C_{12}$ (hetero)aryl group. Preferably, $R^{18}$ is hydrogen, a $C_1$-$C_6$ alkyl group or a $C_4$-$C_{10}$ (hetero)aryl group, more preferably $R^{18}$ is hydrogen, a $C_1$-$C_4$ alkyl group or a $C_4$-$C_6$ (hetero)aryl group. Even more preferably $R^{18}$ is hydrogen, methyl, ethyl, n-propyl, i-propyl, n-butyl, s-butyl, t-butyl or pyridyl. Yet even more preferably $R^{18}$ is hydrogen, methyl or pyridyl.

In another preferred embodiment, Q is a cycloalkenyl group. The cycloalkenyl group is optionally substituted. Preferably said cycloalkenyl group is a $C_3$-$C_{24}$ cycloalkenyl group, more preferably a $C_3$-$C_{12}$ cycloalkenyl group, and even more preferably a $C_3$-$C_8$ cycloalkenyl group. In a preferred embodiment, the cycloalkenyl group is a trans-cycloalkenyl group, more preferably a trans-cyclooctenyl group (also referred to as a TCO group) and most preferably a trans-cyclooctenyl group according to formula (9h) or (9i) as shown below. In another preferred embodiment, the cycloalkenyl group is a cyclopropenyl group, wherein the cyclopropenyl group is optionally substituted. In another preferred embodiment, the cycloalkenyl group is a norbornenyl group, an oxanorbornenyl group, a norbornadienyl group or an oxanorbornadienyl group, wherein the norbornenyl group, oxanorbornenyl group, norbornadienyl group or an oxanorbornadienyl group is optionally substituted. In a further preferred embodiment, the cycloalkenyl group is according to formula (9j), (9k), (9l) or (9m) as shown below, wherein T is $CH_2$ or O, $R^{26}$ is independently selected from the group consisting of hydrogen, a linear or branched $C_1$-$C_{12}$ alkyl group or a $C_4$-$C_{12}$ (hetero)aryl group, and $R^{26}$ is selected from the group consisting of hydrogen and fluorinated hydrocarbons. Preferably, $R^{26}$ is independently hydrogen or a $C_1$-$C_6$ alkyl group, more preferably $R^{26}$ is independently hydrogen or a $C_1$-$C_4$ alkyl group. Even more preferably $R^{26}$ is independently hydrogen or methyl, ethyl, n-propyl, i-propyl, n-butyl, s-butyl ort-butyl. Yet even more preferably $R^{26}$ is independently hydrogen or methyl. In a further preferred embodiment, $R^{19}$ is selected from the group of hydrogen and $—CF_3$, $—C_2F_5$, $—C_3F_7$ and $—C_4F_9$, more preferably hydrogen and $—CF_3$. In a further preferred embodiment, the cycloalkenyl group is according to formula (9j), wherein one $R^{26}$ is hydrogen and the other $R^{26}$ is a methyl group. In another further preferred embodiment, the cycloalkenyl group is according to formula (9k), wherein both $R^{26}$ are hydrogen. In these embodiments it is further preferred that I is 0 or 1. In another further preferred embodiment, the cycloalkenyl group is a norbornenyl (T is $CH_2$) or an oxanorbornenyl (T is O) group according to formula (9l), or a norbornadienyl (T is $CH_2$) or an oxanorbornadienyl (T is O) group according to formula (9m), wherein $R^{26}$ is hydrogen and $R^{19}$ is hydrogen or $—CF_3$, preferably $—CF_3$.

In another preferred embodiment, Q is an azido group according to structure (9n) below. Herein, l is an integer in the range of 0 to 10, preferably in the range of 0 to 6. More preferably, l is 0, 1, 2, 3 or 4, more preferably l is 0, 1 or 2 and most preferably l is 0 or 1.

(9a)

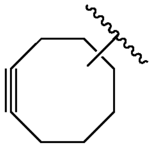

(9b)

$—(CH_2)_l—C≡CH$ (9c)

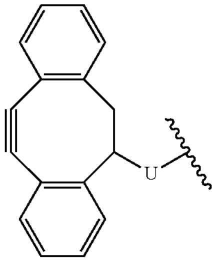

(9d)

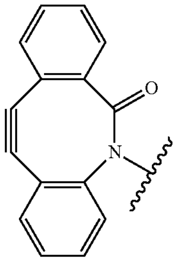

(9e)

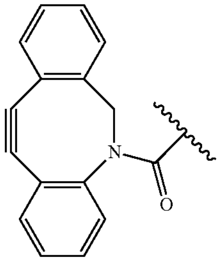

-continued (9f)

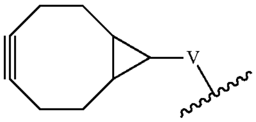

(9g)

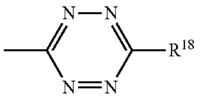

(9h)

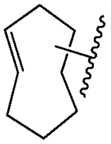

(9i)

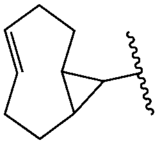

(9j)

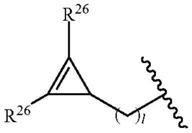

(9k)

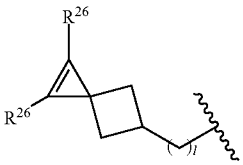

(9l)

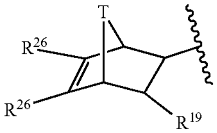

(9m)

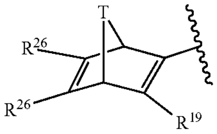

(9n)

$—(CH)_l—N_3$

In one embodiment, Q is according to general structure (10a):

(10a)

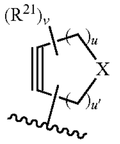

Herein $R^{21}$ is independently selected from the group consisting of hydrogen, halogen, $—OR^{22}$, $—NO_2$, —CN, $—S(O)_2R^{22}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)

arylalkyl groups and wherein the alkyl groups, (hetero)aryl groups, alkyl(hetero)aryl groups and (hetero)arylalkyl groups are optionally substituted, wherein two substituents $R^{21}$ may be linked together to form an annelated cycloalkyl or an annelated (hetero)arene substituent, and wherein $R^{22}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

X is $C(R^{25})_2$, O, S or $NR^{25}$, wherein $R^{25}$ is $R^{21}$ or $-(L^1)_n-(L^2)_o-(L^3)_p-(L^4)_q-D$;

u is 0, 1, 2, 3, 4 or 5;

u' is 0, 1, 2, 3, 4 or 5;

wherein u+u'=5;

v=9 or 10.

In one embodiment, Q is according to general structure (10b):

(10b)

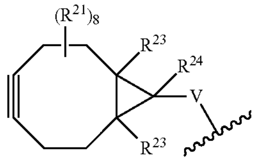

Herein $R^{21}$ is independently selected from the group consisting of hydrogen, halogen, $-OR^{22}$, $-NO_2$, $-CN$, $-S(O)_2R^{22}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{21}$ may be linked together to form an annelated cycloalkyl or an annelated (hetero)arene substituent, and wherein $R^{22}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

$R^{23}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups $R^{24}$ is selected from the group consisting of hydrogen, $(V)_t-(L^1)_n-(L^2)_o-(L^3)_p-(L^4)_q-D$, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted; and $V=(CH_2)_l$ and l is an integer in the range of 0 to 10.

Cytotoxin D

D represents a cytotoxin that comprises an enediyne moiety. Such cytotoxins are also known as enediyne antibiotics. Preferably, D is selected from the group consisting of calicheamicins, esperamicins, shishijimicin and namenamicin. The enediyne antibiotic in the context of the present invention is characterized by a common structural moiety according to structure (21). The inventors have developed a mode of derivatisation to enable conjugation of these potent toxins to antibodies. As such, the high toxicity of the enediynes is channelled to the target site, such as the tumour. The combination of the location of the conjugation, via structural moiety (21), and the mode of conjugation, using a click probe, provides unprecedented advantages both for the final antibody-conjugate as well as in the process for synthesizing the antibody-conjugate.

Structural motive (21) contains a tetrahydropyran ring substituted with a methoxy and a secondary amine moiety. The wavy line indicates the connection to the remainder of the cytotoxin. Amine substituent $R^{12}=C_{1-3}$-alkyl, typically ethyl or isopropyl. In the compounds according to the present invention, the amine H is replaced by $Q-(L^1)_n-(L^2)_o-(L^3)_p-(L^4)_q-$, as in structure (22). Thus, in one embodiment, the compound according to the invention is represented by general structure (22), wherein the wavy line indicates the connection to the remainder of the cytotoxin.

(21)

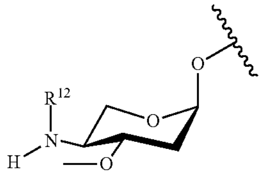

(22)

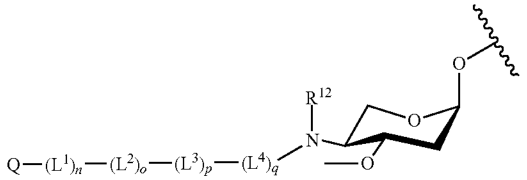

Enediyne antibiotics having structural moiety (21) are well known in the art, and include calicheamicins, esperamicins, shishijimicins and namenamicins. Thus, in one embodiment, the cytotoxin is selected from this list. Amongst the calicheamicins, calicheamicin $\gamma_1^I$ is most preferred. Amongst the esperamicins, esperamicin A1 is most preferred. Amongst the shishijimicins, shishijimicin A is most preferred. Functional derivatives of these cytotoxins are also considered part of the present invention, especially for those having structural moiety (21). In the context of the present invention, an especially preferred derivatisation of the enediyne antibiotic is the transformation of the $-S_3CH_3$ moiety (as present in the unmodified enediyne antibiotic) to an $-S_2R^2$ moiety, wherein $R^2$ is further defined below. Thus, in one embodiment, the cytotoxin contains the structural motive (26).

(26)

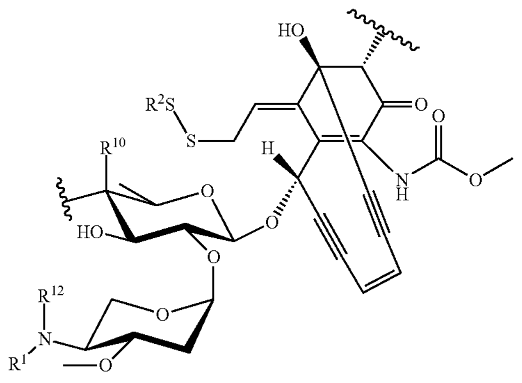

Herein, the wavy lines indicate the connection to the remainder of the cytotoxin, as known in the art, $R^{10}$ is H or $SCH_3$ and $R^{12}$ is ethyl or isopropyl, depending on the structure of the cytotoxin. $R^1$=-$(L^4)_q$-$(L^3)_p$-$(L^2)_o$-$(L^1)_n$-Q and $R^2$ is as defined below. Thus, in one embodiment, the compound according to the invention is represented by general structure (26), wherein the wavy line indicates the connection to the remainder of the cytotoxin.

Accordingly, the compound according to the invention is preferably represented by any one of structures (11), (12), (13), (14) and (15):

(11)

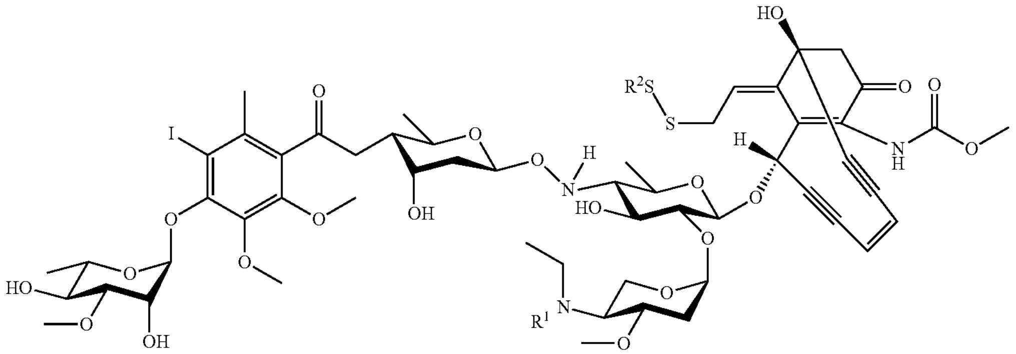

(12)

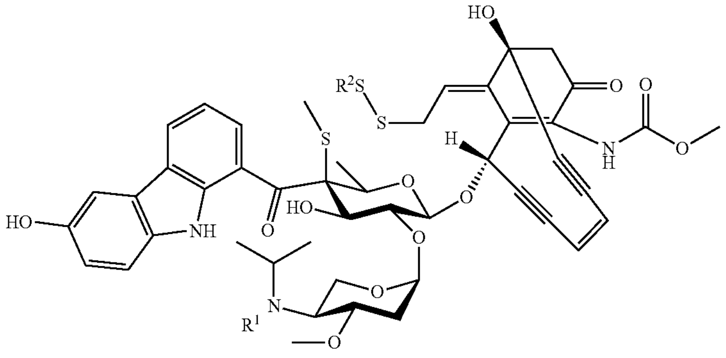

(13)

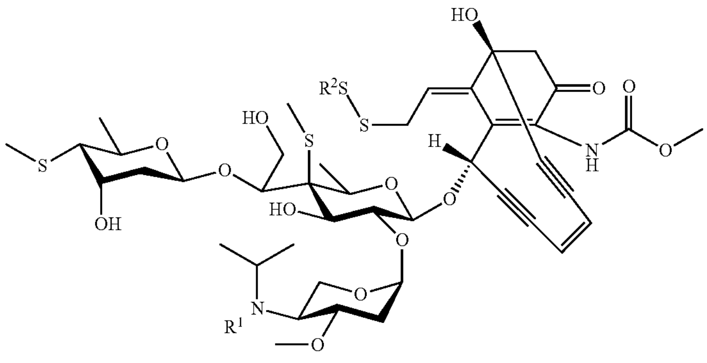

-continued (14)

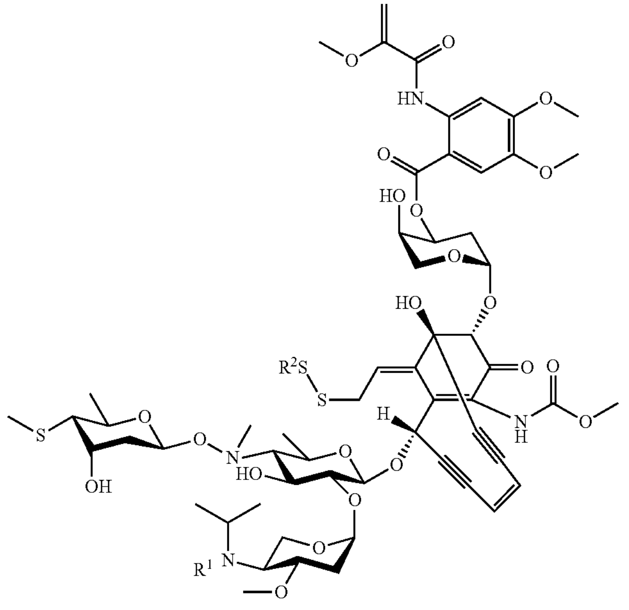

Herein, $R^1$=-$(L^4)_q$-$(L^3)_p$-$(L^2)_o$-$(L^1)_n$-Q and $R^2$ are as defined below.

In an especially preferred embodiment, the cytotoxin is calicheamicin, most preferably calicheamicin $\gamma_1$ or calicheamicin $\gamma_1^I$. According to this embodiment, the compounds according to the invention may be represented by structure (15):

Substituent $R^2$ $R^2$ is —S($C_1$-$C_{10}$ alkyl) or —C$(R^6)_2R^7$, preferably —$SCH_3$ or —C$(R^6)_2R^7$, wherein each $R^6$ is independently selected from H or optionally substituted $C_1$-$C_6$ alkyl and $R^7$ is selected from H, $C_1$-$C_{12}$ alkyl, -$L^5$-$OR^8$, $(CH_2)_s$O-$L^5$-$OR^8$ or $(CH_2)_s$C(O)$NR^{29}$-$L^5$-$OR^8$. Preferably, $R^7$ is selected from -$L^5$-$OR^8$, $(CH_2)_s$O-$L^5$-$OR^8$ or $(CH_2)_s$C(O)$NR^{29}$-$L^5$-$OR^8$, (15)

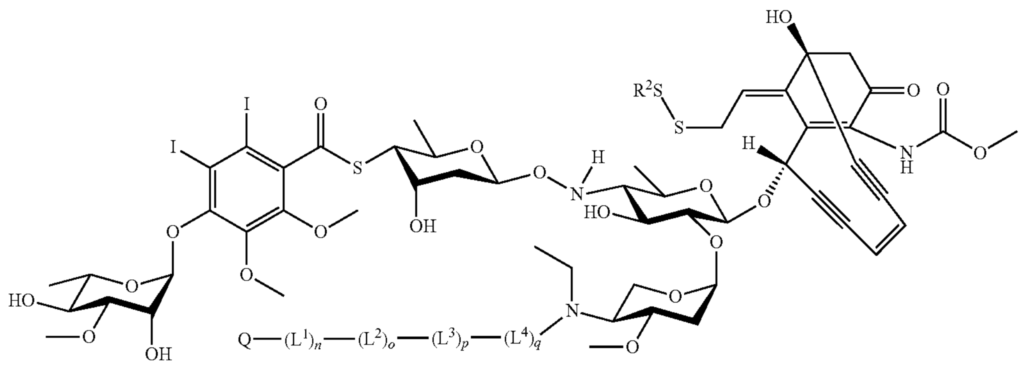

Herein, Q, $L^1$, $L^2$, $L^3$, $L^4$, $R^2$ n, o, p and q are as defined elsewhere.

The compound according to the invention may comprise more than one moiety D. When more than one cytotoxin D is present the cytotoxins D may be the same or different, typically they are the same. In a preferred embodiment, the compound according to the invention contains 1 or 2 occurrences of D, most preferably 1 occurrence of D. Typically, the second occurrence of D is present within $L^1$, which may contain a branching moiety, typically a nitrogen atom, that is connected to the second occurrence of D. Preferably, both occurrences of D are connected to the branching moiety via the same linker.

most preferably $R^7$=$(CH_2)_2$O-$L^5$-$OR^8$. Herein, $L^5$ is a polar linker having 1-100 optionally substituted backbone atoms selected from C, N, O and S, $R^8$ is H or methyl, s=1, 2 or 3, preferably s=3. and $R^{29}$ is selected from H and -$L^5$-$OR^8$, preferably $R^{29}$=H. In one preferred embodiment, $R^2$ is —$SCH_3$ or —C$(CH_3)_2(R^7)$. In case $R^2$ is —S($C_1$-$C_{10}$ alkyl), it is preferred that $R^2$ is —S($C_1$-$C_4$ alkyl), more preferably wherein the alkyl is selected from methyl, ethyl, propyl, isopropyl and butyl. Most preferably, the alkyl is methyl.

$L^5$ is a linker having 1-100 backbone atoms, preferably 1-50 backbone atoms, most preferably 3-40 backbone atoms, selected from C, N, O and S. Backbone atoms herein refer to the shortest chain of atoms between the nitrogen atom to which $R^7$ is connected and the $OR^8$ moiety. Each of the backbone atoms may be optionally be substituted, preferably with one or two substituents selected from oxo, $N(R^8)_2$, $OR^8$, $C(O)R^8$, $C(O)OR^8$, $C(O)N(R^8)_2$. An especially preferred substituent for a carbon or sulphur backbone atom is oxo. Preferably, 0-5, more preferably 0-2, of the backbone atoms is substituted. In one embodiment, 0 of the backbone atoms is substituted. In one embodiment, 2 of the backbone atoms is substituted. It is preferred that $L^5$ contains 1-40, preferably 2-30, more preferably 2, 4, 7, 8, 9, 13, 24 or 29 carbon backbone atoms; 0-20, preferably 0-15, more preferably 0, 1, 2, 3, 5, 11 or 13 oxygen backbone atoms, 0-3, preferably 0 or 2, nitrogen backbone atoms; and 0-2, preferably 0 or 1, sulphur backbone atoms.

Preferred linkers $L^5$ are —$(B')_hCH_2CH_2$— and —$(B')_i$—$(X)_j$—$(B')_hCH_2CH_2$—. Herein, B' is a —$CH_2$—$CH_2$—O— moiety. h is an integer in the range 0-24, preferably 0-15, more preferably 0-11, most preferably h=0, 1, 3 or 11. In one embodiment, h=0. In one embodiment, h=1. In one embodiment, h=3. In one embodiment, h=11. i is an integer in the range 0-4, preferably 1 or 2. In one embodiment, i=2. j is an integer in the range 0-6, preferably j=0, 1, 2, 3 or 4, most preferably j=2 or 4. In case j>1, it is preferred that two adjacent occurrences of X are not the same. X is selected from —O—, —NH—, —S(O)—, —$S(O)_2$—, —C(O)—, —NH—C(O)—, —C(O)—NH— and —NH—C(O)—NH—, preferably X is selected from —S(O)—, —$S(O)_2$—, —C(O)—, —NH—C(O)—, —C(O)—NH— and —NH—C(O)—NH—, more preferably X is selected from —$S(O)_2$— and —NH—C(O)—NH—. In an especially preferred embodiment, (X); =—$S(O)_2$—NH—C(O)—NH— or —C(O)—NH—$S(O)_2$—NH—. Further, in a preferred embodiment, $L^5$ contains a sulfamide moiety, preferably a sulfamide moiety according to structure (23) or (24) as further defined below. Most preferably, the sulfamide moiety is an acylsulfamide.

In one preferred embodiment, $R^2$ is —$SCH_3$, $C_1$-$C_8$ alkyl, $C(CH_3)_2CH_2CH_2OR^8$, $C(CH_3)_2CH_2CH_2C(O)OH$, $C(CH_3)_2CH_2CH_2C(O)NHR^{27}$, wherein $R^{27}$=$R^8$, $(B')_h$—H, —$(B')_i$—$S(O)_2NHC(O)NH$—$(B')_h$—H, wherein $R^8$, B', h and i are as defined above. Preferred $C_1$-$C_8$ alkyl groups include isopropyl, tert-butyl and adamantyl.

In an alternative preferred embodiment, $R^2$ is selected from the group consisting of:

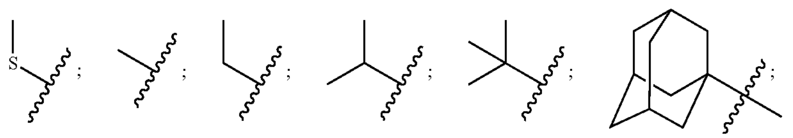

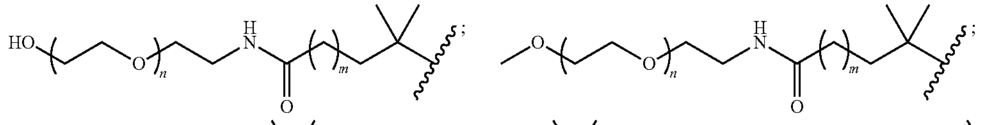

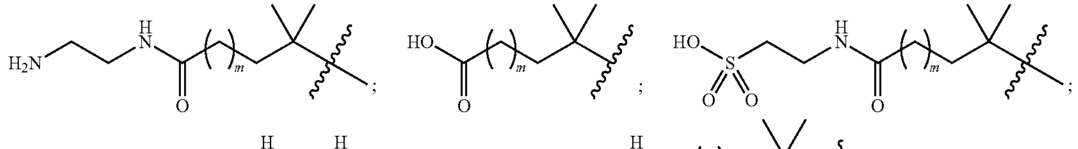

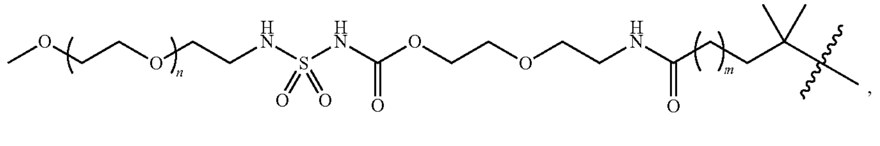

wherein n is an integer in the range 0-100, preferably in the range 1-100, and m is 1 or 2, preferably m is 1.

The inventors found that functionalizing the disulfide of the enediyne antibiotic with a hydrophilic group provides improved characteristics to the compound according to the invention, when compared to similar compounds wherein a probe Q is connected to the enediyne antibiotic via the disulfide. The inventors have made this possible by connecting Q to the enediyne antibiotic via structural motive (21), as defined above, and converting the methyltrisulfide as present in most unmodified enediyne antibiotics to a disulfide group functionalized with $R^2$. The improved characteristics that are imparted due to the presence of a hydrophilic group $R^2$ include higher solubility in aqueous solution, improved click conjugation efficiency, and, once incorporated into an antibody-drug conjugate: less aggregation, improved pharmacokinetics resulting in higher efficacy and in vivo tolerability.

Linkers $L^1$, $L^2$, $L^3$ and $L^4$ are linkers. Linkers (L), also referred to as linking units, are well known in the art. In a preferred embodiment, at least linkers $L^1$ and $L^2$ are present (i.e. n=1; o=1; p=0 or 1; q=0 or 1), more preferably linkers $L^1$, $L^2$ and $L^3$ are present and $L^4$ is either present or not (i.e. n=1; o=1; p=1; q=0 or 1). In one embodiment, linkers $L^1$, $L^2$, $L^3$ and $L^4$ are present (i.e. n=1; o=1; p=1; q=1). In one embodiment, linkers $L^1$, $L^2$ and $L^3$ are present and $L^4$ is not (i.e. n=1; o=1; p=1; q=0).

Linker $L^1$

Linker $L^1$ is either absent (n=0) or present (n=1). Preferably, linker $L^1$ is present and n=1. $L^1$ may for example be selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, $S(O)_y$ and $NR^{15}$, wherein y is 0, 1 or 2, preferably y=2, and $R^{15}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero) arylalkyl groups.

$L^1$ may contain (poly)ethylene glycoldiamines (e.g. 1,8-diamino-3,6-dioxaoctane or equivalents comprising longer ethylene glycol chains), polyethylene glycol or polyethylene oxide chains, polypropylene glycol or polypropylene oxide chains and 1,z-diaminoalkanes wherein z is the number of carbon atoms in the alkane.

In a preferred embodiment, Linker $L^1$ comprises a sulfamide group, preferably a sulfamide group according to structure (23):

(23)

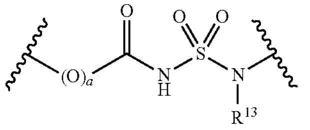

The wavy lines represent the connection to the remainder of the compound, typically to Q and $L^2$, $L^3$, $L^4$ or D, preferably to Q and $L^2$. Preferably, the $(O)_aC(O)$ moiety is connected to Q and the $NR^{13}$ moiety to $L^2$, $L^3$, $L^4$ or D, preferably to $L^2$.

In structure (23), a=0 or 1, preferably a=1, and $R^{13}$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero) arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^{14}$ wherein $R^{14}$ is independently selected from the group consisting of hydrogen and $C_1$-$C_4$ alkyl groups, or $R^{13}$ is D connected to N via a spacer moiety, preferably $Sp^2$ as defined below, in one embodiment D is connected to N via $—(B)_e-(A)_f-(B)_g—C(O)—$.

In a preferred embodiment, $R^{13}$ is hydrogen or a $C_1$-$C_{20}$ alkyl group, more preferably $R^{13}$ is hydrogen or a $C_1$-$C_{16}$ alkyl group, even more preferably $R^{13}$ is hydrogen or a $C_1$-$C_{10}$ alkyl group, wherein the alkyl group is optionally substituted and optionally interrupted by one or more heteroatoms selected from O, S and $NR^{14}$, preferably O, wherein $R^{14}$ is independently selected from the group consisting of hydrogen and $C_1$-$C_4$ alkyl groups. In a preferred embodiment, $R^{13}$ is hydrogen. In another preferred embodiment, $R^{13}$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^{13}$ is a (poly)ethylene glycol chain comprising a terminal —OH group. In another preferred embodiment, $R^{13}$ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably, $R^{13}$ is hydrogen or methyl, and most preferably $R^{13}$ is hydrogen.

In a preferred embodiment, $L^1$ is according to structure (24):

(24)

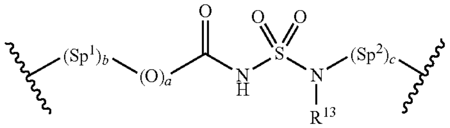

Herein, a and $R^{13}$ are as defined above, $Sp^1$ and $Sp^2$ are independently spacer moieties and b and c are independently 0 or 1. Preferably, b=0 or 1 and c=1, more preferably b=0 and c=1. In one embodiment, spacers $Sp^1$ and $Sp^2$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$ and $Sp^2$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_8$-$C_{100}$ cycloalkynylene groups, $C_7$-$C_{100}$ alkylarylene groups, $C_7$-$C_{100}$ arylalkylene groups, $C_8$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$ and $Sp^2$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$ and $Sp^2$, if present, are independently selected from the group consisting of linear or branched $C_1$-$C_{20}$ alkylene groups, $C_2$-$C_{20}$ alkenylene groups, $C_2$-$C_{20}$alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^{16}$, preferably O, wherein $R^{16}$ is independently selected from the group consisting of hydrogen and $C_1$-$C_4$ alkyl groups, preferably hydrogen or methyl.

Most preferably, spacer moieties $Sp^1$ and $Sp^2$, if present, are independently selected from the group consisting of linear or branched $C_1$-$C_{20}$ alkylene groups, the alkylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^{16}$, preferably O and/or or S—S, wherein $R^3$ is independently selected from the group consisting of hydrogen and $C_1$-$C_4$ alkyl groups, preferably hydrogen or methyl.

Preferred spacer moieties $Sp^1$ and $Sp^2$ thus include $—(CH_2)_r—$, $—(CH_2CH_2)_r—$, $—(CH_2CH_2O)_r$, $—(OCH_2CH_2)_r$, $—(CH_2CH_2O)_rCH_2CH_2—$, $—CH_2CH_2(OCH_2CH_2)_r$, $—(CH_2CH_2CH_2O)_r$, $—(OCH_2CH_2CH_2)_r$, $—(CH_2CH_2CH_2O)_rCH_2CH_2CH_2—$ and $—CH_2CH_2CH_2(OCH_2CH_2CH_2)_r—$, wherein r is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Alternatively, preferred linkers $L^1$ may be represented by $—(W)_k$-$(A)_d$-$(B)_e$-$(A)_f$-$(C(O))_g—$, wherein:

d=0 or 1, preferably d=1;

e=an integer in the range 0-10, preferably e=0, 1, 2, 3, 4, 5 or 6, preferably an integer in the range 1-10, most preferably e=1, 2, 3 or 4;

f=0 or 1, preferably f=0;

wherein d+e+f is at least 1, preferably in the range 1-5; and preferably wherein d+f is at least 1, preferably d+f=1.

g=0 or 1, preferably g=1;

k=0 or 1, preferably k=1;

A is a sulfamide group according to structure (23);

B is a $—CH_2—CH_2—O—$ or a $—O—CH_2—CH_2—$ moiety, or $(B)_e$ is a $—(CH_2—CH_2—O)_{e1}—CH_2—CH_2—$ moiety, wherein e1 is defined the same way as e;

W is —OC(O)—, —C(O)O—, —C(O)NH—, —NHC(O)—, —OC(O)NH—, —NHC(O)O—, $—C(O)(CH_2)_mC(O)—$, $—C(O)(CH_2)_mC(O)NH—$ or -(4-Ph)$CH_2NHC(O)(CH_2)_mC(O)NH—$, preferably wherein W is —OC(O)NH—, $—C(O)(CH_2)_mC(O)NH—$ or —C(O)NH—, and wherein m is an integer in the range 0-10, preferably m=0, 1, 2, 3, 4, 5 or 6, most preferably m=2 or 3;

preferably wherein $L^1$ is connected to Q via $(A)_d$-$(B)_e$ and to $L^2$, $L^3$, $L^4$ or D, preferably to $L^2$, via $(C(O))_g$, preferably via C(O).

In the context of the present embodiment, the wavy lines in structure (23) represent the connection to the adjacent groups such as $(W)_k$, $(B)_e$ and $(C(O))_g$. It is preferred that A is according to structure (23), wherein a=1 and $R^{13}$=H or a $C_1$-$C_{20}$ alkyl group, more preferably $R^{13}$=H or methyl, most preferably $R^{13}$=H.

Preferred linkers $L^1$ are as follows:

(a) k=0; d=1; g=1; f=0; B=$—CH_2—CH_2—O—$; e=1, 2, 3 or 4, preferably e=2.

(b) k=1; W=$—C(O)(CH_2)_mC(O)NH—$; m=2; d=0; $(B)_e$=$—(CH_2—CH_2$-$0)_{e1}—CH_2—CH_2—$; f=0; g=1; e1=1, 2, 3 or 4, preferably e=1.

(c) k=1; W=—OC(O)NH—; d=0; B=$—CH_2—CH_2—O—$; g=1; f=0; e=1, 2, 3 or 4, preferably e=2.

(d) k=1; W=$—C(O)(CH_2)_mC(O)NH—$; m=2; d=0; $(B)_e$=$—(CH_2—CH_2$-$0)_{e1}—CH_2—CH_2—$; f=0; g=1; e1=1, 2, 3 or 4, preferably e1=4.

(e) k=1; W=—OC(O)NH—; d=0; $(B)_e$=$—(CH_2—CH_2$-$0)_{e1}—CH_2—CH_2—$; g=1; f=0; e1=1, 2, 3 or 4, preferably e1=4.

(f) k=1; W=—(4-Ph)$CH_2NHC(O)(CH_2)_mC(O)NH—$, m=3; d=0; $(B)_e$=$—(CH_2—CH_2—O)_{e1}—CH_2—CH_2—$; g=1; f=0; e1=1, 2, 3 or 4, preferably e1=4.

(g) k=0; d=0; g=1; f=0; B=$—CH_2—CH_2—O—$; e=1, 2, 3 or 4, preferably e=2.

(h) k=1; W=—C(O)NH—; d=0; g=1; f=0; B=$—CH_2—CH_2—O—$; e=1, 2, 3 or 4, preferably e=2.

In one embodiment, linker $L^1$ comprises a branching nitrogen atom, which is located in the backbone between Q and $(L^2)_o$ and which contains a further moiety D as substituent, which is preferably linked to the branching nitrogen atom via a linker. An example of a branching nitrogen atom is the nitrogen atom $NR^{13}$ in structure (23), wherein $R^{13}$ is connected to a second occurrence of D via a spacer moiety. Alternatively, a branching nitrogen atoms may be located within $L^1$ according to structure $—(W)_k$-$(A)_d$-$(B)_e$-$(A)_f$-$(C(O))_g—$. In one embodiment, $L^1$ is represented by $—(W)_k$-$(A)_d$-$(B)_e$-$(A)_f$-$(C(O))_g—N^*[$-$(A)_d$-$(B)_e$-$(A)_f$-$(C(O))_g$-$]_2$, wherein A, B, W, d, e, f, g and k are as defined above and individually selected for each occurrence, and N* is the branching nitrogen atoms, to which two instances of $-(A)_d-(B)_e-(A)_f-(C(O))_g-$ are connected. Herein, both $(C(O))_g$ moieties are connected to $-(L^2)_o-(L^3)_p-(L^4)_q-D$, wherein $L^2$, $L^3$, $L^4$, o, p, q and D are as defined above and are each selected individually.

Linker $L^2$

Linker $L^2$ is either absent (o=0) or present (o=1). Preferably, linker $L^2$ is present and o=1. Linker $L^2$ is a peptide spacer as known in the art, preferably a dipeptide or tripeptide spacer as known in the art, preferably a dipeptide spacer. Although any dipeptide or tripeptide spacer may be used, preferably linker $L^2$ is selected from Val-Cit, Val-Ala, Val-Lys, Val-Arg, Phe-Cit, Phe-Ala, Phe-Lys, Phe-Arg, Ala-Lys, Leu-Cit, Ile-Cit, Trp-Cit, Ala-Ala-Asn, Ala-Asn, more preferably Val-Cit, Val-Ala, Val-Lys, Phe-Cit, Phe-Ala, Phe-Lys, Ala-Ala-Asn, more preferably Val-Cit, Val-Ala, Ala-Ala-Asn. In one embodiment, $L^2$=Val-Cit. In one embodiment, $L^2$=Val-Ala.

In a preferred embodiment, $L^2$ is represented by general structure (27):

(27)

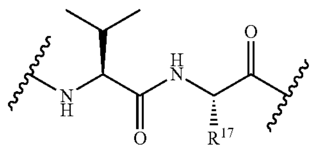

Herein, $R^{17}=CH_3$ or $CH_2CH_2CH_2NHC(O)NH_2$. The wavy lines indicate the connection to $(L^1)_n$ and $(L^3)_p$, preferably $L^2$ according to structure (27) is connected to $(L^1)_n$ via NH and to $(L^3)_p$ via C(O).

Linker $L^3$

Linker $L^3$ is either absent (p=0) or present (p=1). Preferably, linker $L^3$ is present and p=1. Linker $L^3$ is a self-cleavable spacer, also referred to as self-immolative spacer. Preferably, $L^3$ is para-aminobenzyloxycarbonyl (PABC) derivative, more preferably a PABC derivative according to structure (25).

(25)

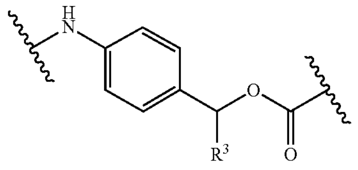

Herein, the wavy lines indicate the connection to Q, $L^1$ or $L^2$, and to $L^4$ or D. Typically, the PABC derivative is connected via NH to Q, $L^1$ or $L^2$, preferably to $L^2$, and via O to $L^4$ or D.

$R^3$ is H, $R^4$ or $C(O)R^4$, wherein $R^4$ is $C_1$-$C_{24}$ (hetero)alkyl groups, $C_3$-$C_{10}$ (hetero)cycloalkyl groups, $C_2$-$C_{10}$ (hetero) aryl groups, $C_3$-$C_{10}$ alkyl(hetero)aryl groups and $C_3$-$C_{10}$ (hetero)arylalkyl groups, which optionally substituted and optionally interrupted by one or more heteroatoms selected from O, S and $NR^5$ wherein $R^5$ is independently selected from the group consisting of hydrogen and $C_1$-$C_4$ alkyl groups. Preferably, $R^4$ is $C_3$-$C_{10}$ (hetero)cycloalkyl or polyalkylene glycol. The polyalkylene glycol is preferably a polyethylene glycol or a polypropylene glycol, more preferably $-(CH_2CH_2O)_sH$ or $-(CH_2CH_2CH_2O)_sH$. The polyalkylene glycol is most preferably a polyethylene glycol, preferably $-(CH_2CH_2O)_sH$, wherein s is an integer in the range 1-10, preferably 1-5, most preferably s=1, 2, 3 or 4. More preferably, $R^3$ is H or $C(O)R^4$, wherein $R^4$=4-methyl-piperazine or morpholine. Most preferably, $R^3$ is H.

Linker $L^4$

Linker $L^4$ is either absent (q=0) or present (q=1). Preferably, linker $L^4$ is present and q=1. Linker $L^4$ is an aminoalkanoic acid spacer, i.e. $-N-(C_x\text{-alkylene})-C(O)-$, wherein x is an integer in the range 1 to 20, preferably 1-10, most preferably 1-6. Herein, the aminoalkanoic acid spacer is typically connected to $L^3$ via the nitrogen atom and to D via the carbonyl moiety. Preferred linkers $L^4$ are selected from 6-aminohexanoic acid (Ahx, x=6), β-alanine (x=2) and glycine (Gly, x=1), even more preferably 6-aminohexanoic acid or glycine. In one embodiment, $L^4$=6-aminohexanoic acid. In one embodiment, $L^4$=glycine. Or linker $L^4$ is a an ethyleneglycol spacer according to the structure $-N-(CH_2-CH_2-O)_{e6}-(CH_2)_{e7}-(C(O)-$, wherein e6 is an integer in the range 1-10 and e7 is an integer in the range 1-3.

Preferred Compounds

Preferred compounds according to the first aspect are selected from the group consisting of compounds (I)-(III). More preferred compounds are selected from (X)-(XXII). In one especially preferred embodiment, the compound is selected from (X), (XII), (XIII), (XIV), (XV) and (XXIV). In one especially preferred embodiment, the compound is selected from (X)-(XX). The structures of these compounds are defined here below.

Compound (I) has the following structure:

$$Q-(L^1)_n-(L^2)_o-(L^3)_p-(L^4)_q-D \qquad (I)$$

wherein:

Q is a click probe, comprising a reactive group selected from (hetero)cycloalkyne and azide;

D is a cytotoxin containing an enediyne moiety as further defined above;

$L^1$ is a linker represented by $-(A)_d-(B)_e-(A)_f-(C(O))_g-$, as defined above;

$L^2$ is Val-Cit or Val-Ala;

$L^3$ is the PABC derivative according to structure (25);

$L^4$ is $-N-(C_x\text{-alkylene})-C(O)-$, wherein x is an integer in the range 1 to 20;

q=0 or 1.

In the context of compound (I), it is preferred that D is according to structure (11), i.e. the compound is according to structure (15), with n=o=p=1. In the context of compound (I), it is preferred that Q comprises a (hetero)cyclooctyne, more preferably a group according to structure (9f), most preferably wherein $V=CH_2$ (i.e. I=1). In the context of compound (I), it is preferred that for $L^1$, d=1 (and for A according to structure (23), it is preferred that a=1 and $R^{13}$=H), e=2, f=0 and g=1. In the context of compound (I), it is preferred that $L^2$=Val-Cit. In the context of compound (I), it is preferred that for $L^3$, $R^3$=H. In the context of compound (I), it is preferred that in case q=1, then x=1 or 6.

Compound (II) has the following structure:

$$Q—(L^1)—(L^2)—(L^3)—D \qquad (II)$$

wherein:

Q is a click probe, comprising a (hetero)cyclooctyne reactive group;

D is a cytotoxin containing an enediyne moiety as further defined above;

$L^1$ is a linker represented by -(A)-(B)$_e$—(C(O))—, as defined above;

$L^2$ is Val-Cit or Val-Ala;

$L^3$ is the PABC derivative according to structure (25), wherein $R^3$=H.

In the context of compound (II), it is preferred that D is according to structure (11), i.e. the compound is according to structure (15), with n=o=p=1 and q=0. In the context of compound (II), it is preferred that Q is according to structure (9f), preferably wherein V=$CH_2$ (i.e. I=1). In the context of compound (II), it is preferred that for $L^1$, e=2, and for A according to structure (23), it is preferred that a=1 and $R^{13}$=H. In the context of compound (II), it is preferred that $L^2$=Val-Cit.

Compound (III) has the following structure:

$$Q—(L^1)—(L^2)—(L^3)—(L^4)—D \qquad (III)$$

wherein:

Q is a click probe, comprising a (hetero)cyclooctyne reactive group;

D is a cytotoxin containing an enediyne moiety as further defined above;

$L^1$ is a linker represented by -(A)-(B)$_e$—(C(O))—, as defined above;

$L^2$ is Val-Cit or Val-Ala;

$L^3$ is the PABC derivative according to structure (25), wherein $R^3$=H;

$L^4$ is —N—($C_x$-alkylene)-C(O)—, wherein x is an integer in the range 1 to 6.

In the context of compound (III), it is preferred that D is according to structure (11), i.e. the compound is according to structure (15), with n=o=p=1 and q=0. In the context of compound (III), it is preferred that Q is according to structure (9f), preferably wherein V=$CH_2$ (i.e. I=1). In the context of compound (III), it is preferred that for $L^1$, e=2, and with a=1 and $R^{13}$=H. In the context of compound (III), it is preferred that $L^2$=Val-Cit. In the context of compound (III), it is preferred that x=1 or 6.

Compound (X) has the following structure:

(X)

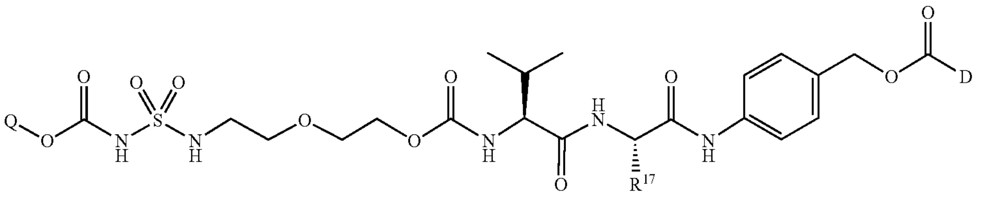

Herein Q, D and $R^{17}$ are as defined above. In the context of compounds (X), it is preferred that D is calicheamicin according to structure (11), wherein $R^2$=—$SCH_3$ or —$C(R^6)_2$ $R^7$, wherein each $R^6$ and $R^7$ are defined as above, more preferably $R^2$=—$C(R^6)_2R^7$.

For preferred compound (Xa), Q is BCN according to structure (9f), with V=$CH_2$; D is calicheamicin according to structure (11), wherein $R^2$=—$C(R^6)_2R^7$, wherein each $R^6$ and $R^7$ are defined as above; and $R^{17}$ is $CH_3$. For preferred compound (Xb), Q is BCN according to structure (9f), with V=$CH_2$; D is calicheamicin according to structure (11), wherein $R^2$=—$C(R^6)_2R^7$, wherein each $R^6$ and $R^7$ are defined as above; and $R^{17}$ is $CH_2CH_2CH_2NHC(O)NH_2$.

For preferred compound (Xc), Q is BCN according to structure (9f), with V=$CH_2$; D is calicheamicin according to structure (11), wherein $R^2$=—$SCH_3$; and $R^{17}$ is $CH_3$. For preferred compound (Xb), Q is BCN according to structure (9f), with V=$CH_2$; D is calicheamicin according to structure (11), wherein $R^2$=—$SCH_3$; and $R^{17}$ is $CH_2CH_2CH_2NHC(O)NH_2$.

Compound (XI) has the following structure:

(XI)

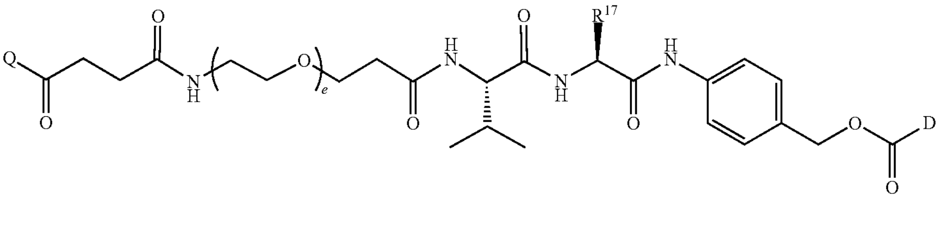

Herein Q, D, e and $R^{17}$ are as defined above. In the context of compounds (XI), it is preferred that D is calicheamicin according to structure (11), wherein $R^2$=—$SCH_3$ or —$C(R^6)_2$ $R^7$, wherein each $R^6$ and $R^7$ are defined as above, more preferably $R^2$=—$C(R^6)_2R^7$.

For preferred compound (XIa), Q is DIBAC according to structure (9e), wherein the carbonyl (C(O)) moiety is absent; D is calicheamicin according to structure (11), wherein $R^2$=—$C(R^6)_2R^7$, wherein each $R^6$ and $R^7$ are defined as above; e is 4; and $R^{17}$ is $CH_3$. For preferred compound (XIb), Q is DIBAC according to structure (9e), wherein the carbonyl (C(O)) moiety is absent; D is calicheamicin according to structure (11), wherein $R^2$=—$C(R^6)_2R^7$, wherein each $R^6$ and $R^7$ are defined as above; e is 4; and $R^{17}$ is $CH_2CH_2CH_2NHC(O)NH_2$.

For preferred compound (XIc), Q is DIBAC according to structure (9e), wherein the carbonyl (C(O)) moiety is absent; D is calicheamicin according to structure (11), wherein $R^2$=—$SCH_3$; e is 4; and $R^{17}$ is $CH_3$. For preferred compound (XId), Q is DIBAC according to structure (9e), wherein the carbonyl (C(O)) moiety is absent; D is calicheamicin according to structure (11), wherein $R^2$=—$SCH_3$; e is 4; and $R^{17}$ is $CH_2CH_2CH_2NHC(O)NH_2$.

Compound (XII) has the following structure:

(XII)

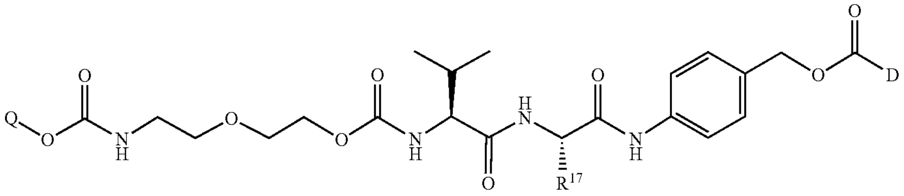

Herein Q, D and $R^{17}$ are as defined above. In the context of compounds (XII), it is preferred that D is calicheamicin according to structure (11), wherein $R^2$=—$SCH_3$ or —$C(R^6)_2$ $R^7$, wherein each $R^6$ and $R^7$ are defined as above, more preferably $R^2$=—$C(R^6)_2R^7$.

For preferred compound (XIIa), Q is BCN according to structure (9f), with V=$CH_2$; D is calicheamicin according to structure (11), wherein $R^2$=—$C(R^6)_2R^7$, wherein each $R^6$ and $R^7$ are defined as above; and $R^{17}$ is $CH_3$. For preferred compound (XIIb), Q is BCN according to structure (9f), with V=$CH_2$; D is calicheamicin according to structure (11), wherein $R^2$=—$C(R^6)_2R^7$, wherein each $R^6$ and $R^7$ are defined as above; and $R^{17}$ is $CH_2CH_2CH_2NHC(O)NH_2$.

For preferred compound (XIIc), Q is DIBO according to structure (9c); D is calicheamicin according to structure (11), wherein $R^2$=—$C(R^6)_2R^7$, wherein each $R^6$ and $R^7$ are defined as above; and $R^{17}$ is $CH_3$. For preferred compound (XIId), Q is DIBO according to structure (9f); D is calicheamicin according to structure (11), wherein $R^2$=—$C(R^6)_2$ $R^7$, wherein each $R^6$ and $R^7$ are defined as above; and $R^{17}$ is $CH_2CH_2CH_2NHC(O)NH_2$.

For preferred compound (XIId), Q is BCN according to structure (9f), with V=$CH_2$; D is calicheamicin according to structure (11), wherein $R^2$=—$SCH_3$; and $R^{17}$ is $CH_3$. For preferred compound (XIIe), Q is BCN according to structure (9f), with V=$CH_2$; D is calicheamicin according to structure (11), wherein $R^2$=—$SCH_3$; and $R^{17}$ is $CH_2CH_2CH_2NHC(O)NH_2$.

For preferred compound (XIIf), Q is DIBO according to structure (9c); D is calicheamicin according to structure (11), wherein $R^2$=—$SCH_3$; and $R^{17}$ is $CH_3$. For preferred compound (XIIg), Q is DIBO according to structure (9f); D is calicheamicin according to structure (11), wherein $R^2$=—$C(R^6)_2R^7$; and $R^{17}$ is $CH_2CH_2CH_2NHC(O)NH_2$.

Compound (XIII) has the following structure:

(XIII)

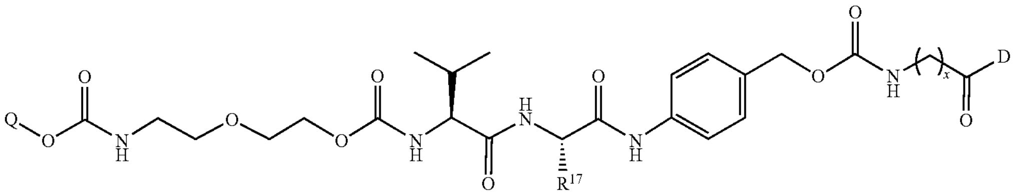

Herein Q, D, x and $R^{17}$ are as defined above. In the context of compounds (XIII), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XIIIa), Q is BCN according to structure (9f), with V=$CH_2$; D is calicheamicin according to structure (11), wherein $R^2$=—$C(R^6)_2R^7$, wherein each $R^6$ and $R^7$ are defined as above; x=1; and $R^{17}$ is $CH_3$. For preferred compound (XIIIb), Q is BCN according to structure (9f), with V=$CH_2$; D is calicheamicin according to structure (11), wherein $R^2$=—$C(R^6)_2R^7$, wherein each $R^6$ and $R^7$ are defined as above; x=6; and $R^{17}$ is $CH_3$. For preferred compound (XIIIc), Q is BCN according to structure (9f), with V=$CH_2$; D is calicheamicin according to structure (11), wherein $R^2$=—$C(R^6)_2R^7$, wherein each $R^6$ and $R^7$ are defined as above; x=1; 9f $R^{17}$ is $CH_2CH_2CH_2NHC(O)NH_2$. For preferred compound (XIIId), Q is BCN according to structure (9f), with V=$CH_2$; D is calicheamicin according to structure (11), wherein $R^2$=—$C(R^6)_2R^7$, wherein each $R^6$ and $R^7$ are defined as above; x=6; and $R^{17}$ is $CH_2CH_2CH_2NHC(O)NH_2$.

For preferred compound (XIIIe), Q is DIBO according to structure (9e); D is calicheamicin according to structure (11), wherein $R^2$=—$C(R^6)_2R^7$; x=1; and $R^{17}$ is $CH_3$. For preferred compound (XIIIf), Q is DIBO according to structure (9e); D is calicheamicin according to structure (11), wherein $R^2$=—$C(R^6)_2R^7$; x=1; 9f $R^{17}$ is $CH_2CH_2CH_2NHC(O)NH_2$.

For preferred compound (XIIIg), Q is BCN according to structure (9f), with V=$CH_2$; D is calicheamicin according to structure (11), wherein $R^2$=—$SCH_3$; x=1; and $R^{17}$ is $CH_3$. For preferred compound (XIIIh), Q is BCN according to structure (9f), with V=$CH_2$; D is calicheamicin according to structure (11), wherein $R^2$=—$SCH_3$; x=6; and $R^{17}$ is $CH_3$. For preferred compound (XIIIi), Q is BCN according to structure (9f), with V=$CH_2$; D is calicheamicin according to structure (11), wherein $R^2$=—$SCH_3$; x=1; 9f $R^{17}$ is $CH_2CH_2CH_2NHC(O)NH_2$. For preferred compound (XIIIj), Q is BCN according to structure (9f), with V=$CH_2$; D is calicheamicin according to structure (11), wherein $R^2$=—$SCH_3$; x=6; and $R^{17}$ is $CH_2CH_2CH_2NHC(O)NH_2$.

For preferred compound (XIIIk), Q is DIBO according to structure (9e); D is calicheamicin according to structure (11), wherein $R^2$=—$SCH_3$; x=1; and $R^{17}$ is $CH_3$. For preferred compound (XIIIl), Q is DIBO according to structure (9e); D is calicheamicin according to structure (11), wherein $R^2$=—$SCH_3$; x=1; 9f $R^{17}$ is $CH_2CH_2CH_2NHC(O)NH_2$.

Compound (XIV) has the following structure:

For preferred compound (XIVa), Q is BCN according to structure (9f), with V=$CH_2$; D is calicheamicin according to structure (11), wherein $R^2$=—$C(R^6)_2R^7$, wherein each $R^6$ and $R^7$ are defined as above; x=1; and $R^{17}$ is $CH_3$. For preferred compound (XIVb), Q is BCN according to structure (9f), with V=$CH_2$; D is calicheamicin according to structure (11), wherein $R^2$=—$C(R^6)_2R^7$, wherein each $R^6$ and $R^7$ are defined as above; x=6; and $R^{17}$ is $CH_3$.

For preferred compound (XIVc), Q is BCN according to structure (9f), with V=$CH_2$; D is calicheamicin according to structure (11), wherein $R^2$=—$C(R^6)_2R^7$, wherein each $R^6$ and $R^7$ are defined as above; x=1; and $R^{17}$ is $CH_2CH_2CH_2NHC(O)NH_2$. For preferred compound (XIVd), Q is BCN according to structure (9f), with V=$CH_2$; D is calicheamicin according to structure (11), wherein $R^2$=—$C(R^6)_2R^7$, wherein each $R^6$ and $R^7$ are defined as above; x=6; and $R^{17}$ is $CH_2CH_2CH_2NHC(O)NH_2$.

For preferred compound (XIVe), Q is BCN according to structure (9f), with V=$CH_2$; D is calicheamicin according to structure (11), wherein $R^2$=isopropyl; x=1; and $R^{17}$ is $CH_3$. For preferred compound (XIVf), Q is BCN according to structure (9f), with V=$CH_2$; D is calicheamicin according to structure (11), wherein $R^2$=isopropyl; x=1; and $R^{17}$ is $CH_2CH_2CH_2NHC(O)NH_2$.

For preferred compound (XIVg), Q is BCN according to structure (9f), with V=$CH_2$; D is calicheamicin according to structure (11), wherein $R^2$=tert-butyl; x=1; and $R^{17}$ is $CH_3$. For preferred compound (XIVh), Q is BCN according to structure (9f), with V=$CH_2$; D is calicheamicin according to structure (11), wherein $R^2$=tert-butyl; x=1; and $R^{17}$ is $CH_2CH_2CH_2NHC(O)NH_2$.

For preferred compound (XIVi), Q is BCN according to structure (9f), with V=$CH_2$; D is calicheamicin according to structure (11), wherein $R^2$=$C(CH_3)_2CH_2CH_2OH$; x=1; and $R^{17}$ is $CH_3$. For preferred compound (XIVj), Q is BCN according to structure (9f), with V=$CH_2$; D is calicheamicin according to structure (11), wherein $R^2$=$C(CH_3)_2CH_2CH_2OH$; x=1; and $R^{17}$ is $CH_2CH_2CH_2NHC(O)NH_2$.

For preferred compound (XIVk), Q is BCN according to structure (9f), with V=$CH_2$; D is calicheamicin according to structure (11), wherein $R^2$=$C(CH_3)_2CH_2CH_2OCH_3$; x=1; and $R^{17}$ is $CH_3$. For preferred compound (XIVl), Q is BCN according to structure (9f), with V=$CH_2$; D is calicheamicin according to structure (11), wherein $R^2$=$C(CH_3)_2CH_2CH_2OCH_3$; x=1; and $R^{17}$ is $CH_2CH_2CH_2NHC(O)NH_2$.

For preferred compound (XIVm), Q is BCN according to structure (9f), with V=$CH_2$; D is calicheamicin according to structure (11), wherein $R^2$=$C(CH_3)_2CH_2CH_2C(O)OH$; x=1; and $R^{17}$ is $CH_3$. For preferred compound (XIVn), Q is BCN (XIV)

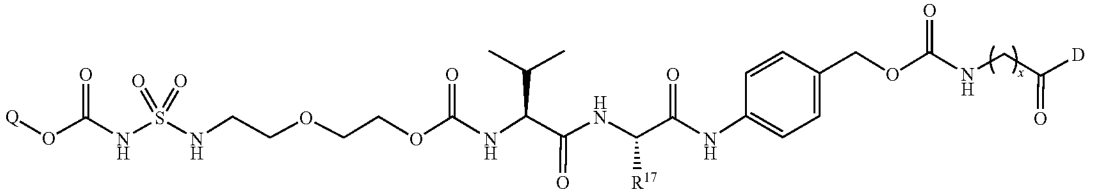

Herein Q, D, x and $R^{17}$ are as defined above. In the context of compounds (XIV), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

according to structure (9f), with V=$CH_2$; D is calicheamicin according to structure (11), wherein $R^2$=$C(CH_3)_2CH_2CH_2C(O)OH$; x=1; and $R^{17}$ is $CH_2CH_2CH_2NHC(O)NH_2$.

For preferred compound (XIVo), Q is BCN according to structure (9f), with V=$CH_2$; D is calicheamicin according to structure (11), wherein $R^2$=1-adamantyl; x=1; and $R^{17}$ is $CH_3$. For preferred compound (XIVp), Q is BCN according to structure (9f), with $V{=}CH_2$; D is calicheamicin according to structure (11), wherein $R^2$=1-adamantyl; x=1; and $R^{17}$ is $CH_2CH_2CH_2NHC(O)NH_2$.

For preferred compound (XIVq), Q is BCN according to structure (9f), with $V{=}CH_2$; D is calicheamicin according to structure (11), wherein $R^2{=}C(CH_3)_2CH_2CH_2C(O)NH(CH_2CH_2O)_2H$; x=1; and $R^{17}$ is $CH_3$. For preferred compound (XIVr), Q is BCN according to structure (9f), with $V{=}CH_2$; D is calicheamicin according to structure (11), wherein $R^2{=}C(CH_3)_2CH_2CH_2C(O)NH—(CH_2CH_2O)_2H$; x=1; and $R^{17}$ is $CH_2CH_2CH_2NHC(O)NH_2$.

For preferred compound (XIVs), Q is BCN according to structure (9f), with $V{=}CH_2$; D is calicheamicin according to structure (11), wherein $R^2{=}C(CH_3)_2CH_2CH_2C(O)NH(CH_2CH_2O)_4H$; x=1; and $R^{17}$ is $CH_3$. For preferred compound (XIVt), Q is BCN according to structure (9f), with $V{=}CH_2$; D is calicheamicin according to structure (11), wherein $R^2{=}C(CH_3)_2CH_2CH_2C(O)NH—(CH_2CH_2O)_4H$; x=1; and $R^{17}$ is $CH_2CH_2CH_2NHC(O)NH_2$.

For preferred compound (XIVu), Q is BCN according to structure (9f), with $V{=}CH_2$; D is calicheamicin according to structure (11), wherein $R^2{=}C(CH_3)_2CH_2CH_2C(O)NH(CH_2CH_2O)_{13}H$; x=1; and $R^{17}$ is $CH_3$. For preferred compound (XIVv), Q is BCN according to structure (9f), with $V{=}CH_2$; D is calicheamicin according to structure (11), wherein $R^2{=}C(CH_3)_2CH_2CH_2C(O)NH—(CH_2CH_2O)_{13}H$; x=1; and $R^{17}$ is $CH_2CH_2CH_2NHC(O)NH_2$.

For preferred compound (XIVw), Q is BCN according to structure (9f), with $V{=}CH_2$; D is calicheamicin according to structure (11), wherein $R^2{=}C(CH_3)_2CH_2CH_2C(O)NH(CH_2CH_2O)_2—S(O)_2NHC(O)NH(CH_2CH_2O)_2H$; x=1; and $R^{17}$ is $CH_3$. For preferred compound (XIVx), Q is BCN according to structure (9f), with $V{=}CH_2$; D is calicheamicin according to structure (11), wherein $R^2{=}C(CH_3)_2CH_2CH_2C(O)NH(CH_2CH_2O)_2S(O)_2NHC(O)NH(CH_2CH_2O)_2H$; x=1; and $R^{17}$ is $CH_2CH_2CH_2NHC(O)NH_2$.

For preferred compound (XIVy), Q is BCN according to structure (9f), with $V{=}CH_2$; D is calicheamicin according to structure (11), wherein $R^2{=}—SCH_3$; x=1; and $R^{17}$ is $CH_3$. For preferred compound (XIVz), Q is BCN according to structure (9f), with $V{=}CH_2$; D is calicheamicin according to structure (11), wherein $R^2{=}—SCH_3$; x=6; and $R^{17}$ is $CH_3$.

For preferred compound (XIVaa), Q is BCN according to structure (9f), with $V{=}CH_2$; D is calicheamicin according to structure (11), wherein $R^2{=}—SCH_3$; x=1; and $R^{17}$ is $CH_2CH_2CH_2NHC(O)NH_2$. For preferred compound (XIVab), Q is BCN according to structure (9f), with $V{=}CH_2$; D is calicheamicin according to structure (11), wherein $R^2{=}—SCH_3$; x=6; and $R^{17}$ is $CH_2CH_2CH_2NHC(O)NH_2$.

Compound (XV) has the following structure:

(XV)

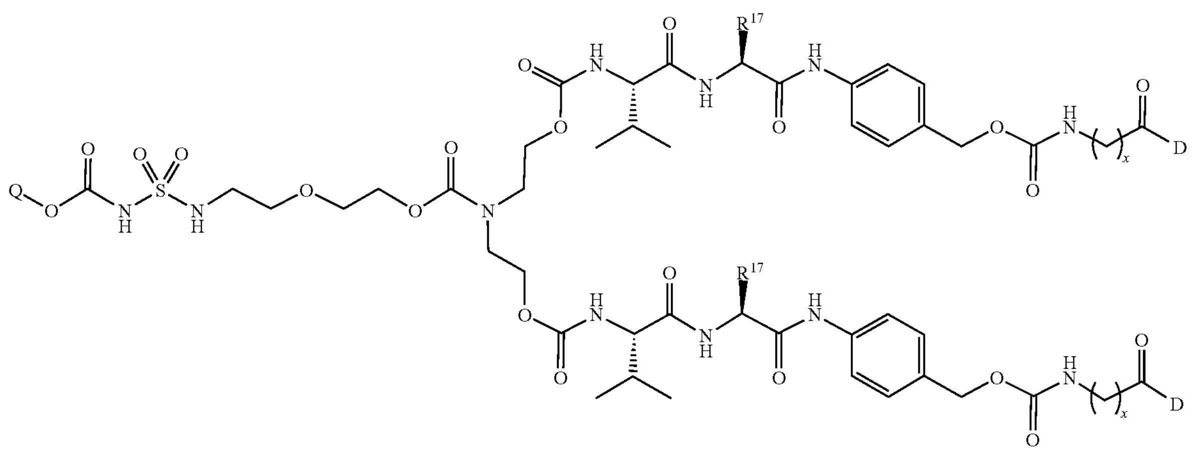

Herein Q, D, x and $R^{17}$ are as defined above. In the context of compounds (XV), it is preferred that D is calicheamicin according to structure (11), wherein $R^2{=}—SCH_3$ or $—C(R^6)_2R^7$, wherein each $R^6$ and $R^7$ are defined as above, more preferably $R^2{=}—C(R^6)_2R^7$.

For preferred compound (XVa), Q is BCN according to structure (9f), with $V{=}CH_2$; D is calicheamicin according to structure (11), wherein $R^2{=}—C(R^6)_2R^7$, wherein each $R^6$ and $R^7$ are defined as above; each x=1; and each $R^{17}{=}CH_3$. For preferred compound (XVb), Q is BCN according to structure (9f), with $V{=}CH_2$; D is calicheamicin according to structure (11), wherein $R^2{=}—C(R^6)_2R^7$, wherein each $R^6$ and $R^7$ are defined as above; each x=6; and each $R^{17}{=}CH_3$. For preferred compound (XVc), Q is BCN according to structure (9f), with $V{=}CH_2$; D is calicheamicin according to structure (11), wherein $R^2{=}—C(R^6)_2R^7$, wherein each $R^6$ and $R^7$ are defined as above; each x=1; and each $R^{17}{=}CH_2CH_2CH_2NHC(O)NH_2$. For preferred compound (XVd), Q is BCN according to structure (9f), with $V{=}CH_2$; D is calicheamicin according to structure (11), wherein $R^2{=}—C(R^6)_2R^7$, wherein each $R^6$ and $R^7$ are defined as above; each x=6; and each $R^{17}{=}CH_2CH_2CH_2NHC(O)NH_2$.

For preferred compound (XVe), Q is BCN according to structure (9f), with $V{=}CH_2$; D is calicheamicin according to structure (11), wherein $R^2{=}—SCH_3$; each x=1; and each $R^{17}{=}CH_3$. For preferred compound (XVf), Q is BCN according to structure (9f), with $V{=}CH_2$; D is calicheamicin according to structure (11), wherein $R^2{=}—SCH_3$; each x=6; and each $R^{17}{=}CH_3$. For preferred compound (XVg), Q is BCN according to structure (9f), with $V{=}CH_2$; D is calicheamicin according to structure (11), wherein $R^2{=}—SCH_3$; each x=1; and each $R^{17}{=}CH_2CH_2CH_2NHC(O)NH_2$. For preferred compound (XVh), Q is BCN according to structure (9f), with $V{=}CH_2$; D is calicheamicin according to structure (11), wherein $R^2{=}—SCH_3$; each x=6; and each $R^{17}{=}CH_2CH_2CH_2NHC(O)NH_2$.

Compound (XVI) has the following structure:

(XVI)

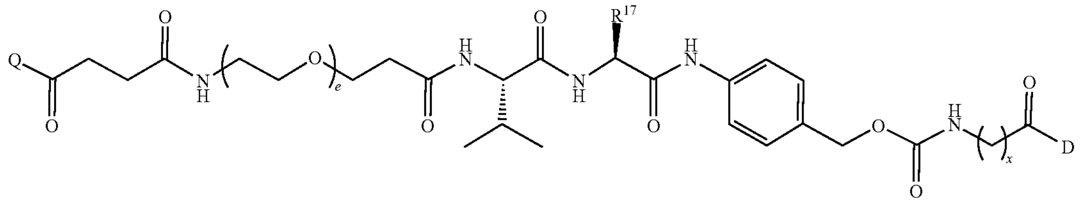

Herein Q, D, e, x and $R^{17}$ are as defined above. In the context of compounds (XVI), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XVIa), Q is DIBAC according to structure (9e), wherein the carbonyl (C(O)) moiety is absent; D is calicheamicin according to structure (11), wherein $R^2$=—$C(R^6)_2R^7$, wherein each $R^6$ and $R^7$ are defined as above; e=4; x=1; and $R^{17}$=$CH_3$. For preferred compound (XVIb), Q is DIBAC according to structure (9e), wherein the carbonyl (C(O)) moiety is absent; D is calicheamicin according to structure (11), wherein $R^2$=—$C(R^6)_2$ $R^7$, wherein each $R^6$ and $R^7$ are defined as above; e=4; x=1; and $R^{17}$=$CH_2CH_2CH_2NHC(O)NH_2$.

For preferred compound (XVIc), Q is DIBAC according to structure (9e), wherein the carbonyl (C(O)) moiety is absent; D is calicheamicin according to structure (11), wherein $R^2$=—$SCH_3$; e=4; x=1; and $R^{17}$=$CH_3$. For preferred compound (XVId), Q is DIBAC according to structure (9e), wherein the carbonyl (C(O)) moiety is absent; D is calicheamicin according to structure (11), wherein $R^2$=—$SCH_3$; e=4; x=1; and $R^{17}$=$CH_2CH_2CH_2NHC(O)NH_2$.

Compound (XVII) has the following structure:

(XVII)

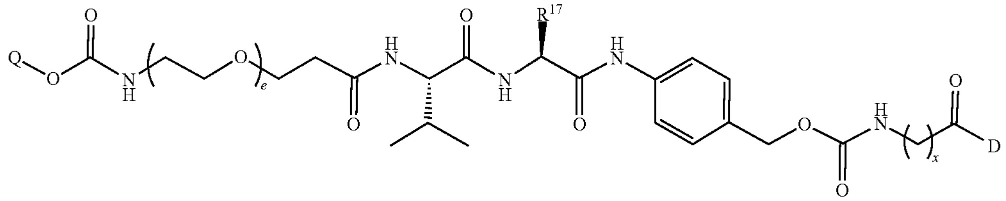

Herein Q, D, e, x and $R^{17}$ are as defined above. In the context of compounds (XVII), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XVIIa), Q is trans-cyclooctene according to structure (9h); D is calicheamicin according to structure (11), wherein $R^2$=—$C(R^6)_2R^7$, wherein each $R^6$ and $R^7$ are defined as above; e=4; x=1; and $R^{17}$=$CH_3$. For preferred compound (XVIIb), Q is trans-cyclooctene according to structure (9h); D is calicheamicin according to structure (11), wherein $R^2$=—$C(R^6)_2R^7$, wherein each $R^6$ and $R^7$ are defined as above; e=4; x=1; and $R^{17}$=$CH_2CH_2CH_2NHC(O)NH_2$. For preferred compound (XVIIc), Q is trans-cyclooctene according to structure (9i); D is calicheamicin according to structure (11), wherein $R^2$=—$C(R^6)_2R^7$, wherein each $R^6$ and $R^7$ are defined as above; e=4; x=1; and $R^{17}$=$CH_3$. For preferred compound (XVIId), Q is trans-cyclooctene according to structure (9i); D is calicheamicin according to structure (11), wherein $R^2$=—$C(R^6)_2R^7$, wherein each $R^6$ and $R^7$ are defined as above; e=4; x=1; and $R^{17}$=$CH_2CH_2CH_2NHC(O)NH_2$.

For preferred compound (XVIIe), Q is trans-cyclooctene according to structure (9h); D is calicheamicin according to structure (11), wherein $R^2$=—$SCH_3$; e=4; x=1; and $R^{17}$=$CH_3$. For preferred compound (XVIIf), Q is trans-cyclooctene according to structure (9h); D is calicheamicin according to structure (11), wherein $R^2$=—$SCH_3$; e=4; x=1; and $R^{17}$=$CH_2CH_2CH_2NHC(O)NH_2$. For preferred compound (XVIIg), Q is trans-cyclooctene according to structure (9i); D is calicheamicin according to structure (11), wherein $R^2$=—$SCH_3$; e=4; x=1; and $R^{17}$=$CH_3$. For preferred compound (XVIIh), Q is trans-cyclooctene according to structure (9i); D is calicheamicin according to structure (11), wherein $R^2$=—$SCH_3$; e=4; x=1; and $R^{17}$=$CH_2$ $CH_2CH_2NHC(O)NH_2$.

Compound (XVIII) has the following structure:

(XVIII)

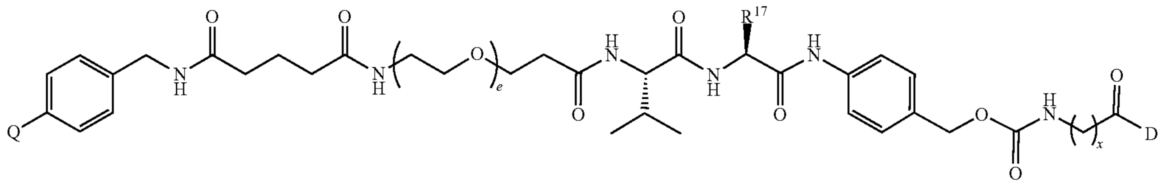

Herein Q, D, e, x and $R^{17}$ are as defined above. In the context of compounds (XVIII), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XVIIIa), Q is a tetrazine according to structure (9g), wherein $R^{18}$=H; D is calicheamicin according to structure (11), wherein $R^2$=—$C(R^6)_2R^7$, wherein each $R^6$ and $R^7$ are defined as above; e=4; x=1; and $R^{17}$=$CH_3$. For preferred compound (XVIIIb), Q is tetrazine according to structure (9g), wherein $R^{18}$=H; D is calicheamicin according to structure (11), wherein $R^2$=—C $(R^6)_2$ $R^7$, wherein each $R^6$ and $R^7$ are defined as above; e=4; x=1; and $R^{17}$=$CH_2CH_2CH_2NHC(O)NH_2$. For preferred compound (XVIIIc), Q is a tetrazine according to structure (9g), wherein $R^{18}$=Me; D is calicheamicin according to structure (11), wherein $R^2$=—$C(R^6)_2R^7$, wherein each $R^6$ and $R^7$ are defined as above; e=4; x=1; and $R^{17}$=$CH_3$. For preferred compound (XVIIId), Q is tetrazine according to structure (9g), wherein $R^{18}$=Me; D is calicheamicin according to structure (11), wherein $R^2$=—$C(R^6)_2R^7$, wherein each $R^6$ and $R^7$ are defined as above; e=4; x=1; and $R^{17}$=$CH_2CH_2CH_2NHC(O)NH_2$.

For preferred compound (XVIIIe), Q is a tetrazine according to structure (9g), wherein $R^{18}$=H; D is calicheamicin according to structure (11), wherein $R^2$=—$SCH_3$; e=4; x=1; and $R^{17}$=$CH_3$. For preferred compound (XVIIIf), Q is tetrazine according to structure (9g), wherein $R^{18}$=H; D is calicheamicin according to structure (11), wherein $R^2$=—$SCH_3$; e=4; x=1; and $R^{17}$=$CH_2CH_2CH_2NHC(O)NH_2$. For preferred compound (XVIIIg), Q is a tetrazine according to structure (9g), wherein $R^{18}$=Me; D is calicheamicin according to structure (11), wherein $R^2$=—$SCH_3$; e=4; x=1; and $R^{17}$=$CH_3$. For preferred compound (XVIIIh), Q is tetrazine according to structure (9g), wherein $R^{18}$=Me; D is calicheamicin according to structure (11), wherein $R^2$=—$SCH_3$; e=4; x=1; and $R^{17}$=$CH_2CH_2CH_2NHC(O)NH_2$.

Compound (XIX) has the following structure:

(XIX)

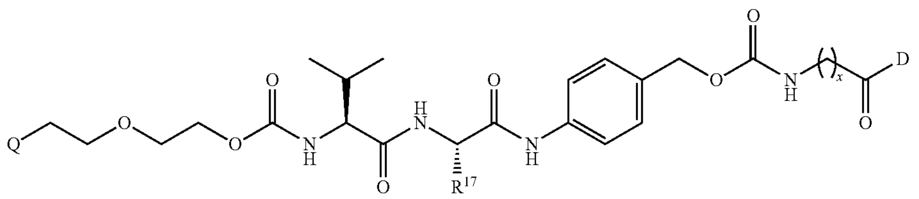

Herein Q, D, x and $R^{17}$ are as defined above. In the context of compounds (XIX), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XIXa), Q is an azido group; D is calicheamicin according to structure (11), wherein $R^2$=—$C(R^6)_2R^7$, wherein each $R^6$ and $R^7$ are defined as above; x=1; and $R^{17}$=$CH_3$. For preferred compound (XIXb), Q is an azido group; D is calicheamicin according to structure (11), wherein $R^2$=—$C(R^6)_2R^7$, wherein each $R^6$ and $R^7$ are defined as above; x=1; and $R^{17}$=$CH_2CH_2CH_2NHC(O)NH_2$.

For preferred compound (XIXc), Q is an azido group; D is calicheamicin according to structure (11), wherein $R^2$=—$SCH_3$; x=1; and $R^{17}$=$CH_3$. For preferred compound (XIXd), Q is an azido group; D is calicheamicin according to structure (11), wherein $R^2$=—$SCH_3$; x=1; and $R^{17}$=$CH_2CH_2CH_2NHC(O)NH_2$.

Compound (XX) has the following structure:

(XX)

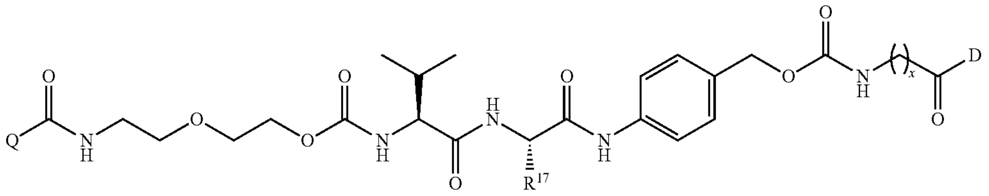

Herein Q, D, x and $R^{17}$ are as defined above. In the context of compounds (XX), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XXa), Q is the terminal alkyne group according to the structure —$(CH_2)_l$—C≡CH, wherein l=2; D is calicheamicin according to structure (11), wherein $R^2$=—$C(R^6)_2R^7$, wherein each $R^6$ and $R^7$ are defined as above; x=1; and $R^{17}$=$CH_3$. For preferred compound (XXb), Q is the terminal alkyne group according to the structure —$(CH_2)_l$—C≡CH, wherein l=2; D is calicheamicin according to structure (11), wherein $R^2$=—$C(R^6)_2R^7$, wherein each $R^6$ and $R^7$ are defined as above; x=1; and $R^{17}$=$CH_2CH_2CH_2NHC(O)NH_2$.

For preferred compound (XXc), Q is the terminal alkyne group according to the structure —$(CH_2)_l$—C≡CH, wherein l=2; D is calicheamicin according to structure (11), wherein $R^2$=—$SCH_3$; x=1; and $R^{17}$=$CH_3$. For preferred compound (XXd), Q is the terminal alkyne group according to the structure —$(CH_2)$—C≡CH, wherein I=2; D is calicheamicin according to structure (11), wherein $R^2$=—$SCH_3$; x=1; and $R^{17}$=$CH_2CH_2CH_2NHC(O)NH_2$.

Compound (XXI) has the following structure:

(XXI)

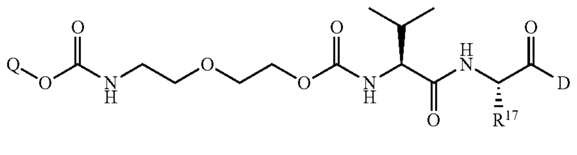

Herein Q, D and $R^{17}$ are as defined above. In the context of compounds (XXI), it is preferred that D is calicheamicin according to structure (11), wherein $R^2$=—$SCH_3$ or —$C(R^6)_2$ $R^7$, wherein each $R^6$ and $R^7$ are defined as above, more preferably $R^2$=—$C(R^6)_2R^7$.

For preferred compound (XXIa), Q is BCN according to structure (9f), with V=$CH_2$; D is calicheamicin according to structure (11), wherein $R^2$=—$C(R^6)_2R^7$, wherein each $R^6$ and $R^7$ are defined as above; and $R^{17}$ is $CH_3$. For preferred compound (XXIb), Q is BCN according to structure (9f), with V=$CH_2$; D is calicheamicin according to structure (11), wherein $R^2$=—$C(R^6)_2R^7$, wherein each $R^6$ and $R^7$ are defined as above; and $R^{17}$ is $CH_2CH_2CH_2NHC(O)NH_2$.

For preferred compound (XXIc), Q is DIBO according to structure (9c); D is calicheamicin according to structure (11), wherein $R^2$=—$C(R^6)_2R^7$, wherein each $R^6$ and $R^7$ are defined as above; and $R^{17}$ is $CH_3$. For preferred compound (XXId), Q is DIBO according to structure (9f); D is calicheamicin according to structure (11), wherein $R^2$=—$C(R^6)_2$ $R^7$, wherein each $R^6$ and $R^7$ are defined as above; and $R^{17}$ is $CH_2CH_2CH_2NHC(O)NH_2$.

For preferred compound (XXIe), Q is BCN according to structure (9f), with V=$CH_2$; D is calicheamicin according to structure (11), wherein $R^2$=—$SCH_3$; and $R^{17}$ is $CH_3$. For preferred compound (XXIf), Q is BCN according to structure (9f), with V=$CH_2$; D is calicheamicin according to structure (11), wherein $R^2$=—$SCH_3$; and $R^{17}$ is $CH_2CH_2CH_2NHC(O)NH_2$.

For preferred compound (XXIg), Q is DIBO according to structure (9c); D is calicheamicin according to structure (11), wherein $R^2$=—$SCH_3$; and $R^{17}$ is $CH_3$. For preferred compound (XXIh), Q is DIBO according to structure (9f); D is calicheamicin according to structure (11), wherein $R^2$=—$C(R^6)_2R^7$; and $R^{17}$ is $CH_2CH_2CH_2NHC(O)NH_2$.

Compound (XXII) has the following structure:

(XXII)

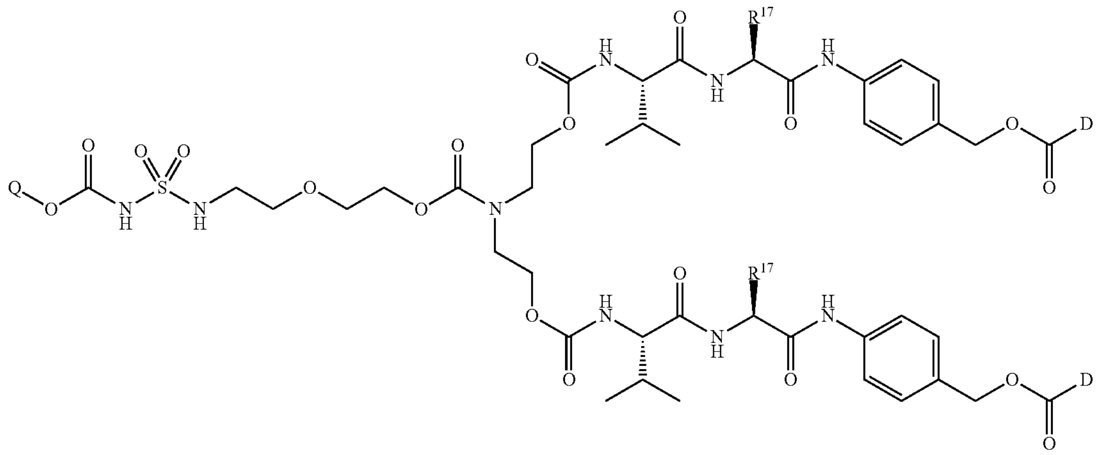

Herein Q, D, x and $R^{17}$ are as defined above. In the context of compounds (XXII), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XXIIa), Q is BCN according to structure (9f), with V=$CH_2$; D is calicheamicin according to structure (11), wherein $R^2$=—$C(R^6)_2R^7$, wherein each $R^6$ and $R^7$ are defined as above; each x=1; and each $R^{17}$=$CH_3$. For preferred compound (XXIIb), Q is BCN according to structure (9f), with V=$CH_2$; D is calicheamicin according to structure (11), wherein $R^2$=—$C(R^6)_2R^7$, wherein each $R^6$ and $R^7$ are defined as above; each x=6; and each $R^{17}$=$CH_3$. For preferred compound (XXIIc), Q is BCN according to structure (9f), with V=$CH_2$; D is calicheamicin according to structure (11), wherein $R^2$=—$C(R^6)_2R^7$, wherein each $R^6$ and $R^7$ are defined as above; each x=1; and each $R^{17}$=$CH_2CH_2CH_2NHC(O)NH_2$. For preferred compound (XXIId), Q is BCN according to structure (9f), with V=$CH_2$; D is calicheamicin according to structure (11), wherein $R^2$=—$C(R^6)_2R^7$, wherein each $R^6$ and $R^7$ are defined as above; each x=6; and each $R^{17}$=$CH_2CH_2CH_2NHC(O)NH_2$.

For preferred compound (XXIIe), Q is BCN according to structure (9f), with V=$CH_2$; D is calicheamicin according to structure (11), wherein $R^2$=—$SCH_3$; each x=1; and each $R^{17}$=$CH_3$. For preferred compound (XXIIf), Q is BCN according to structure (9f), with V=$CH_2$; D is calicheamicin according to structure (11), wherein $R^2$=—$SCH_3$; each x=6; and each $R^{17}$=$CH_3$. For preferred compound (XXIIg), Q is BCN according to structure (9f), with V=$CH_2$; D is calicheamicin according to structure (11), wherein $R^2$=—$SCH_3$; each x=1; and each $R^{17}$=$CH_2CH_2CH_2NHC(O)NH_2$. For preferred compound (XXIIh), Q is BCN according to structure (9f), with V=$CH_2$; D is calicheamicin according to structure (11), wherein $R^2$=—$SCH_3$; each x=6; and each $R^{17}$=$CH_2CH_2CH_2NHC(O)NH_2$.

Compound (XXIII) has the following structure:

(XXIII)

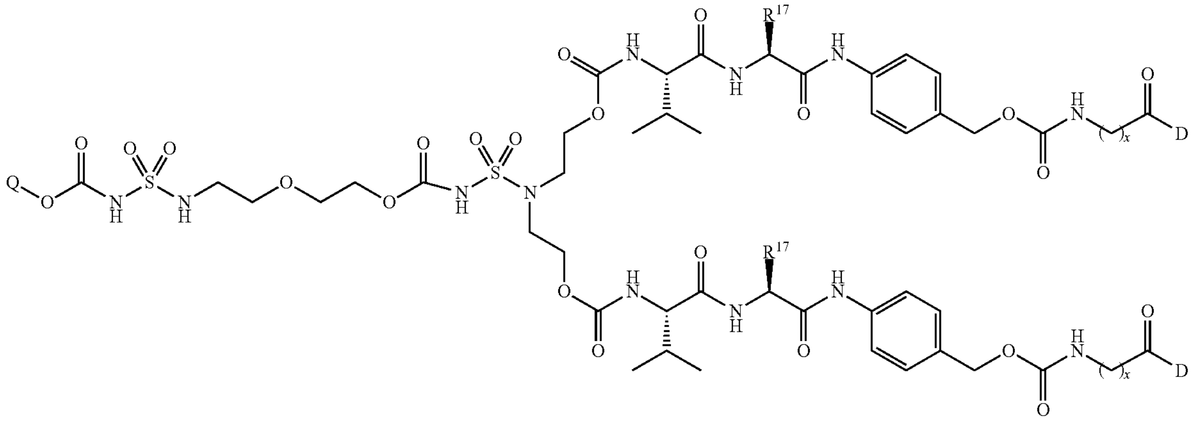

Herein Q, D, x and $R^{17}$ are as defined above. In the context of compounds (XXIII), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XXIIIa), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=1; and each $R^{17}=CH_3$. For preferred compound (XXIIIb), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=6; and each $R^{17}=CH_3$. For preferred compound (XXIIIc), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=1; and each $R^{17}=CH_2CH_2CH_2NHC(O)NH_2$. For preferred compound (XXIIId), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=6; and each $R^{17}=CH_2CH_2CH_2NHC(O)NH_2$.

For preferred compound (XXIIIe), Q is BCN according to structure (9f), with $V=CH_2$; D is calicheamicin according to structure (11), wherein $R^2$=—$SCH_3$; each x=1; and each $R^{17}=CH_3$. For preferred compound (XXIIIf), Q is BCN according to structure (9f), with $V=CH_2$; D is calicheamicin according to structure (11), wherein $R^2$=—$SCH_3$; each x=6; and each $R^{17}=CH_3$. For preferred compound (XXIIIg), Q is BCN according to structure (9f), with $V=CH_2$; D is calicheamicin according to structure (11), wherein $R^2$=—$SCH_3$; each x=1; and each $R^{17}=CH_2CH_2CH_2NHC(O)NH_2$. For preferred compound (XXIIIh), Q is BCN according to structure (9f), with $V=CH_2$; D is calicheamicin according to structure (11), wherein $R^2$=—$SCH_3$; each x=6; and each $R^{17}=CH_2CH_2CH_2NHC(O)NH_2$.

Compound (XXIV) has the following structure:

and $R^7$ are defined as above; each x=6; and each $R^{17}=CH_3$. For preferred compound (XXIVc), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=1; and each $R^{17}=CH_2CH_2CH_2NHC(O)NH_2$. For preferred compound (XXIVd), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=6; and each $R^{17}=CH_2CH_2CH_2NHC(O)NH_2$.

For preferred compound (XXIVe), Q is BCN according to structure (9f), with $V=CH_2$; D is calicheamicin according to structure (11), wherein $R^2$=—$SCH_3$; each x=1; and each $R^{17}=CH_3$. For preferred compound (XXIVf), Q is BCN according to structure (9f), with $V=CH_2$; D is calicheamicin according to structure (11), wherein $R^2$=—$SCH_3$; each x=6; and each $R^{17}=CH_3$. For preferred compound (XXIVg), Q is BCN according to structure (9f), with $V=CH_2$; D is calicheamicin according to structure (11), wherein $R^2$=—$SCH_3$; each x=1; and each $R^{17}=CH_2CH_2CH_2NHC(O)NH_2$. For preferred compound (XXIVh), Q is BCN according to structure (9f), with $V=CH_2$; D is calicheamicin according to structure (11), wherein $R^2$=—$SCH_3$; each x=6; and each $R^{17}=CH_2CH_2CH_2NHC(O)NH_2$.

In a preferred embodiment, the compound according to the invention has general structure (1), wherein D=calicheamicin according to structure (11), preferably wherein $R^2$=—$C(R^6)_2R^7$, wherein each $R^6$ and $R^7$ are defined as above. In a preferred embodiment, the compound according to the invention has general structure (1), wherein Q comprises a cyclooctyne moiety, preferably Q is according to general structure (10a), more preferably Q is accord- (XXIV)

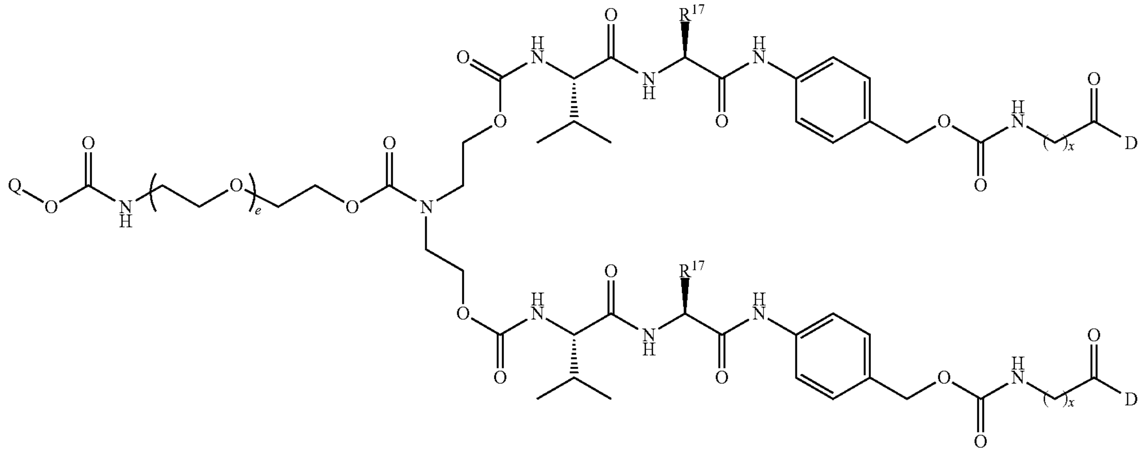

Herein Q, D, x and $R^{17}$ are as defined above. In the context of compounds (XXIV), it is preferred that D is calicheamicin according to structure (11), wherein $R^2$=—$SCH_3$ or —$C(R^6)_2R^7$, wherein each $R^6$ and $R^7$ are defined as above, more preferably $R^2$=—$C(R^6)_2R^7$.

For preferred compound (XXIVa), Q is BCN according to structure (9f), with $V=CH_2$; D is calicheamicin according to structure (11), wherein $R^2$=—$C(R^6)_2R^7$, wherein each $R^6$ and $R^7$ are defined as above; each x=1; and each $R^{17}=CH_3$. For preferred compound (XXIVb), Q is BCN according to structure (9f), with $V=CH_2$; D is calicheamicin according to structure (11), wherein $R^2$=—$C(R^6)_2R^7$, wherein each $R^6$ ing to structure (9c), (9e) or (9f), most preferably Q is according to structure (9f). In a preferred embodiment, the compound according to the invention has general structure (1), wherein D=calicheamicin according to structure (11), preferable wherein $R^2$=—$C(R^6)_2R^7$, wherein each $R^6$ and $R^7$ are defined as above, and Q comprises a cyclooctyne moiety, preferably Q is according to general structure (10a), more preferably Q is according to structure (9c), (9e) or (9f), most preferably Q is according to structure (9f).

In a preferred embodiment, the compound according to the invention has general structure (15), wherein $R^2$=—$C(R^6)_2R^7$, wherein each $R^6$ and $R^7$ are defined as above. In a preferred embodiment, the compound according to the invention has general structure (15), wherein Q comprises a cyclooctyne moiety, preferably Q is according to general structure (10a), more preferably Q is according to structure (9c), (9e) or (9f), most preferably Q is according to structure (9f). In a preferred embodiment, the compound according to the invention has general structure (15), wherein $R^2$=—C$(R^6)_2R^7$, wherein each $R^6$ and $R^7$ are defined as above, and Q comprises a cyclooctyne moiety, preferably Q is according to general structure (10a), more preferably Q is according to structure (9c), (9e) or (9f), most preferably Q is according to structure (9f).

In a preferred embodiment, the compound according to the invention is selected from the group consisting of compounds (I)-(III). Within this embodiment, it is preferred that D=calicheamicin according to structure (11), more preferable wherein $R^2$=—C$(R^6)_2R^7$, wherein each $R^6$ and $R^7$ are defined as above. Within this embodiment, it is preferred that Q comprises a cyclooctyne moiety, preferably Q is according to general structure (10a), more preferably Q is according to structure (9c), (9e) or (9f), most preferably Q is according to structure (9f). Within this embodiment, it is most preferred that the preferred options for Q and D, as defined here, both apply.

In a preferred embodiment, the compound according to the invention is selected from the group consisting of compounds (II) and (III). Within this embodiment, it is preferred that D=calicheamicin according to structure (11), more preferable wherein $R^2$=—C$(R^6)_2R^7$, wherein each $R^6$ and $R^7$ are defined as above. Within this embodiment, it is preferred that Q comprises a cyclooctyne moiety, preferably Q is according to general structure (10a), more preferably Q is according to structure (9c), (9e) or (9f), most preferably Q is according to structure (9f). Within this embodiment, it is most preferred that the preferred options for Q and D, as defined here, both apply.

In a preferred embodiment, the compound according to the invention is selected from the group consisting of compounds (X)-(XXIV). Within this embodiment, it is preferred that D=calicheamicin according to structure (11), more preferable wherein $R^2$=—C$(R^6)_2R^7$, wherein each $R^6$ and $R^7$ are defined as above. Within this embodiment, it is preferred that Q comprises a cyclooctyne moiety, preferably Q is according to general structure (10a), more preferably Q is according to structure (9c), (9e) or (9f), most preferably Q is according to structure (9f). Within this embodiment, it is most preferred that the preferred options for Q and D, as defined here, both apply.

In a preferred embodiment, the compound according to the invention is selected from the group consisting of compounds (X)-(XX). Within this embodiment, it is preferred that D=calicheamicin according to structure (11), more preferable wherein $R^2$=—C$(R^6)_2R^7$, wherein each $R^6$ and $R^7$ are defined as above. Within this embodiment, it is preferred that Q comprises a cyclooctyne moiety, preferably Q is according to general structure (10a), more preferably Q is according to structure (9c), (9e) or (9f), most preferably Q is according to structure (9f). Within this embodiment, it is most preferred that the preferred options for Q and D, as defined here, both apply.

In a preferred embodiment, the compound according to the invention is selected from the group consisting of compounds (X), (XII), (XIII), (XIV), (XV) and (XXIV). Within this embodiment, it is preferred that D=calicheamicin according to structure (11), more preferable wherein $R^2$=—C$(R^6)_2R^7$, wherein each $R^6$ and $R^7$ are defined as above. Within this embodiment, it is preferred that Q comprises a cyclooctyne moiety, preferably Q is according to general structure (10a), more preferably Q is according to structure (9c), (9e) or (9f), most preferably Q is according to structure (9f). Within this embodiment, it is most preferred that the preferred options for Q and D, as defined here, both apply.

Especially preferred compounds according to the present invention are compounds (Xb), (XIIb), (XIIIb), (XIVb), (XIVd), (XIVf), (XIVh), (XIVj), (XIVl), (XIVn), (XIVp), (XIVr), (XIVv), (XIVx), (XVa), (XXIb) and (XXIIa).

Process for Synthesising the Compound According to General Structure (1)

In one aspect, the invention concerns a process for synthesising a compound according to general structure (1), comprising acylation of D (according to structure (21)) through its N-alkylaminosugar (—$NHR^{12}$) with an activated carbonate form of Q-$(L^1)_n$-$(L^2)_o$-$(L^3)_p$, such as a p-nitrophenylcarbonate or N-hydroxysuccinimidyl carbonate derivative. Alternatively, the process comprises acylation of D through its N-alkylaminosugar with an activated ester form of Q-$(L^1)_n$-$(L^2)_o$-$(L^3)_p$-$(L^4)_q$ such as a chloro, a p-nitrophenylcarbonate or N-hydroxysuccinimidyl ester derivative. Alternatively, the process comprises acylation of D through its N-alkylaminosugar with an N-protected and activated ester form of $(L^4)_q$ followed by N-deprotection and acylation with an activated carbonate form of Q-$(L^1)_n$-$(L^2)_o$-$(L^3)_p$ such as a p-nitrophenylcarbonate or N-hydroxysuccinimidyl carbonate derivative. The process according to the present aspect occurs under conditions that enable the acylation of D.

The process according to this aspect is a great improvement over prior art processes for conjugating enediyne antibiotics to further moieties, since the present process requires a single chemical modification of the cytotoxin. In view of its extremely high toxicity, special measures are required to handle enediyne antibiotics, and every synthetic step wherein the enediyne antibiotics or a derivative thereof is present, these measures need to be taken. In the present process, the Q-$(L^1)_n$-$(L^2)_o$-$(L^3)_p$ construct is synthesized and only in the very last step connected to D.

Bioconjugate

In one aspect, the invention concerns a bioconjugate, wherein the compound according to the invention is conjugated to a biomolecule. In the context of the present invention, the biomolecule is a protein, which may be modified in order to be capable in reacting with the compound according to the invention. The protein is preferably a glycoprotein, more preferably the protein is an antibody. The bioconjugate according to the invention may also be referred to as "protein-conjugate", "glycoprotein-conjugate", "antibody-conjugate" or just "conjugate". The bioconjugate according to the invention is according to general structure (2):

$$Pr—[(L^6—Z—(L^1)_n—(L^2)_o—(L^3)_p—(L^4)_q—D]_{xx} \quad (2)$$

Herein, $L^1$, $L^2$, $L^3$, $L^4$, D, n, o, p and q are as defined above for the compound according to the invention. These structural features remain unchanged when the compound according to the invention reacts with the modified protein to form the conjugate according to the invention. Further, Z is a connecting group that is formed when Q on the compound according to the invention reacts with F on the modified protein. Since this reaction is a click reaction, Z contains a moiety that is obtained in a click reaction between Q and F, preferably Z contains a triazole. Further, $L^6$ is a linker that links Z to Pr. Further, Pr is a protein, preferably a glycoprotein, most preferably an antibody and xx is an integer in the range 1-8, preferably in the range 2-8, more preferably in the range 2-4, most preferably x=2.

In one embodiment, $L^6$ is GlcNAc(Fuc)$_w$-S-($L^7$)$_{w'}$—, wherein Pr is a glycoprotein, S is a sugar or a sugar derivative, GlcNAc is N-acetylglucosamine and Fuc is fucose, w is 0 or 1, w' is 0 or 1 and $L^7$ is —N(H)C(O)$CH_2$—, —N(H)C(O)$CF_2$— or —$CH_2$—. The GlcNAc(Fuc)$_w$ is preferably a core-GlcNAc(Fuc)$_w$ moiety, meaning that GlcNAc is the core-sugar moiety in the glycan of a glycoprotein that is directly attached to the peptide chain of the glycoprotein. S is preferably a galactose derivative. w' is preferably 0.

The bioconjugates according to the present invention exhibit improved (i.e. reduced) aggregation, compared to prior art bioconjugates. For example, the bioconjugates according to invention exhibit an extent of aggregation below 5%, preferably below 3%, most preferably below 1%, wherein the extent of aggregation is determined after 21 days in a 1 mg/mL solution at pH 5.0 and 40° C. Even more preferably, the same or lower extent of aggregation is obtained after 21 days in a 1 mg/mL solution at pH 7.4 and 37° C. Typically, PBS solutions are used to determine the extent of aggregation, which may optionally be acidified with 0.1 M sodium citrate. The extent of aggregation may be determined by any means known in the art, e.g. using a XBridge Protein BEH SEC 200 Å column (Waters) on an Agilent 1100 HPLC. Such improved extent of aggregation ensures that the bioconjugates according to the invention are more stable in solution and thus have an improved shelf-life compared to conventional bioconjugates.

The bioconjugates according to the present invention exhibit improved (i.e. reduced) relative retention times as determined by hydrophobic interaction chromatography. For example, the bioconjugates according to invention exhibit a relative retention time of at most 1.3, preferably at most 1.2, more preferably in the range of 1-1.1, based on the retention time of the unmodified Pr. Herein, it is preferred that Pr is an antibody and the relative retention time is determined based on the retention time of the unmodified antibody. Such improved relative retention times imply that the bioconjugates according to the invention exhibit improved pharmacokinetics.

Process for Synthesising the Bioconjugate According to General Structure (2)

In a further aspect, the present invention relates to a process for the preparation of the bioconjugate according to the invention, the process comprising the step of click probe Q of the compound according to the invention with a functional group F of a biomolecule. The compound according to the invention, and preferred embodiments thereof, are described in more detail above. The present process occurs under conditions such that click probe Q of the compound is reacted with the functional group F of the biomolecule to covalently link the biomolecule to the compound. In the process according to the invention, Q reacts with F, forming a covalent connection between the biomolecule and the compound. Complementary reactive groups Q and functional groups F are described in more detail below.

The process according to the present aspect concerns a click reaction, preferably a 1,3-dipolar cycloaddition, most preferably an alkyne/azide cycloaddition. Most preferably, Q is or comprises an alkyne group and F is an azido group. Click reactions, such as 1,3-dipolar cycloadditions, are known in the art, and the skilled person knows how to perform them.

In the process according to the present aspect, more than one functional group F may be present in the biomolecule. When two or more functional groups are present, said groups may be the same or different. For example a biomolecule comprising two functional groups F, i.e. $F^1$ and $F^2$, may react with two compounds comprising a functional group $Q^1$, which may be the same or different, to form a bioconjugate. The functional group in the biomolecule may be naturally present or may be placed in the biomolecule by a specific technique, for example a (bio)chemical or a genetic technique. The functional group that is placed in the biomolecule is prepared by chemical synthesis, for example an azide or a terminal alkyne. F is group capable of reacting in a click reaction, such as a diene, a dienophile, a 1,3-dipole or a dipolarophile, preferably F is selected from the group of 1,3-dipoles (typically an azido group or diazo group) or a dipolarophile (typically an alkenyl or alkynyl group). Herein, F is a 1,3-dipole when Q is a dipolarophile and F is a dipolarophile when Q is a 1,3-dipole, or F is a diene when Q is a dienophile and F is a dienophile when Q is a diene. Most preferably, $F^1$ is a 1,3-dipole, preferably $F^1$ is or comprises an azido group.

Methods of preparing modified glycoproteins are known in the art, e.g. from WO 2014/065661, WO 2016/170186 and WO 2016/053107, which are incorporated herein by reference. From the same documents, the conjugation reaction between the modified glycoprotein and a compound comprising a cytotoxin and a click probe is known to the skilled person.

Uses

The invention further concerns the use of the compound according to the invention for preparing a conjugate according to the invention.

The invention further concerns a method for the treatment of a subject in need thereof, comprising the administration of the bioconjugate according to the invention as defined above. The subject in need thereof is most preferably a cancer patient. The use of bioconjugates, such as antibody-drug conjugates, is well-known in the field of cancer treatment, and the bioconjugates according to the invention are especially suited in this respect. The method as described is typically suited for the treatment of cancer. In the method according to this aspect, the bioconjugate is typically administered in a therapeutically effective dose. The present aspect of the invention can also be worded as a bioconjugate according to the invention for use in the treatment of a subject in need thereof, preferably for the treatment of cancer. In other words, this aspect concerns the use of a bioconjugate according to the invention for the preparation of a medicament or pharmaceutical composition for use in the treatment of a subject in need thereof, preferably for use in the treatment of cancer. The invention thus also concerns a pharmaceutical composition comprising the bioconjugate according to the invention and a pharmaceutically acceptable carrier.

EXAMPLES

Example 1-1: Synthesis of Activated Carbonate Derivative of BCN-Val-Ala-PAB-OPNP

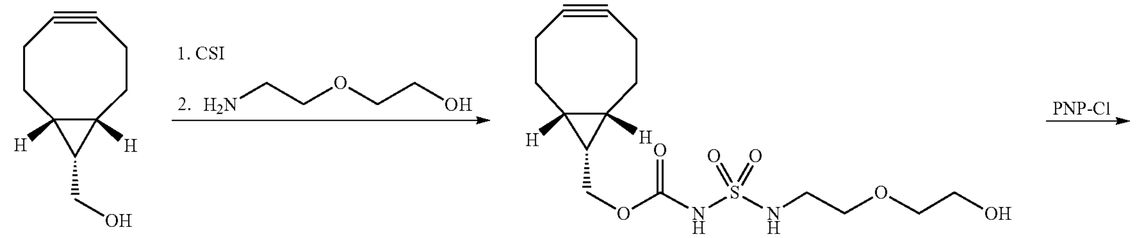

1

2

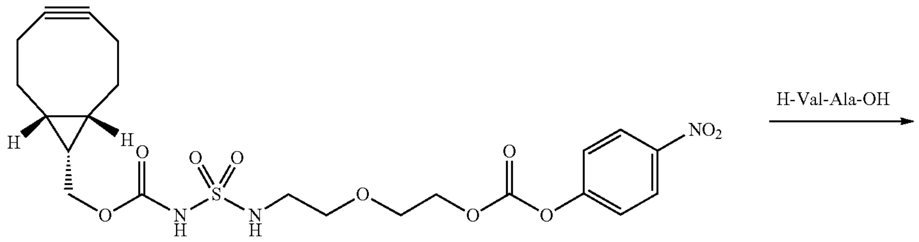

3

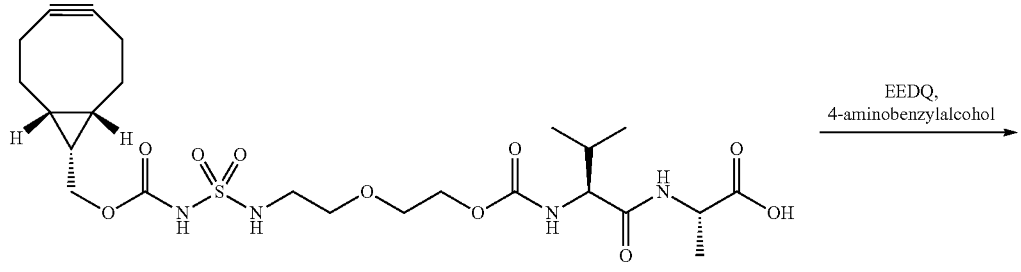

4

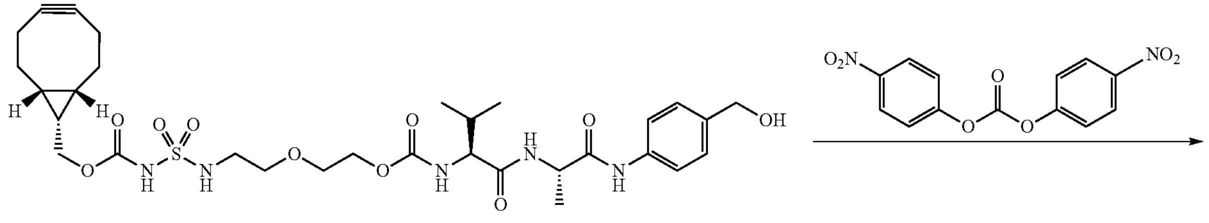

5

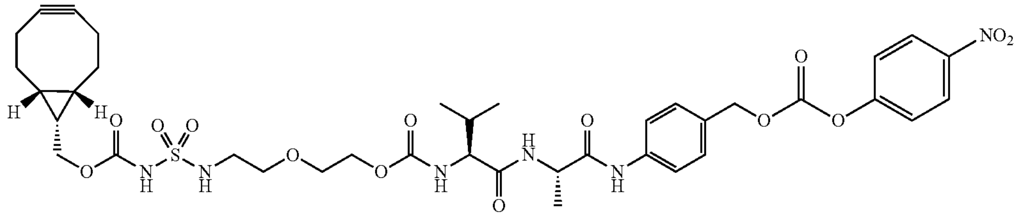

6

To a solution of 1 (1.5 g, 10 mmol) in DCM (150 mL), under a $N_2$ atmosphere, was added CSI (0.87 mL, 1.4 g, 10 mmol), $Et_3N$ (2.8 mL, 2.0 g, 20 mmol) and 2-(2-aminoethoxy)ethanol (1.2 mL, 1.26 g, 12 mmol). The mixture was stirred for 10 min and quenched through addition of aqueous $NH_4Cl$ (sat., 150 mL). After separation, the aqueous layers were extracted with DCM (150 mL). The combined organic layers were dried ($Na_2SO_4$) and concentrated. The residue was purified with column chromatography. Product alcohol 2 was obtained as slightly yellow thick oil (2.06 g, 5.72 mmol, 57%). $^1H$ NMR (400 MHz, $CDCl_3$) δ (ppm) 6.0 (bs, 1H), 4.28 (d, J=8.2 Hz, 2H), 3.78-3.73 (m, 2H), 3.66-3.61 (m, 2H), 3.61-3.55 (m, 2H), 3.34 (t, J=4.9 Hz, 2H), 2.37-2.15 (m, 6H), 1.64-1.48 (m, 2H), 1.40 (quintet, J=8.7 Hz, 1H), 1.05-0.92 (m, 2H).

To a solution of 2 (229 mg, 0.64 mmol) in DCM (20 mL) were added p-nitrophenyl chloroformate (128 mg, 0.64 mmol) and $Et_3N$ (268 mL, 194 mg, 1.92 mmol). The mixture was stirred overnight at rt and subsequently concentrated under reduced pressure. The residue was purified via gradient column chromatography (20→70% EtOAc in heptane (1% AcOH) to afford the PNP carbonate 3 as a white solid (206 mg, 0.39 mmol, 61%). $^1H$ NMR (400 MHz, $CDCl_3$) δ (ppm) 8.31-8.26 (m, 2H), 7.45-7.40 (m, 2H), 5.56 (t, J=6.0 Hz, 1H), 4.48-4.40 (m, 2H), 4.27 (d, J=8.2 Hz, 2H), 3.81-3.75 (m, 2H), 3.68 (t, J=5.0 Hz, 2H), 3.38-3.30 (m, 2H), 2.36-2.14 (m, 6H), 1.61-1.45 (m, 2H), 1.38 (quintet, J=8.7 Hz, 1H), 1.04-0.94 (m, 2H).

To a suspension of H-Val-Ala-OH (98 mg, 0.52 mmol) in DMF (2 mL) were added a solution of 3 (137 mg, 0.261 mmol) in DMF (2 mL) and $Et_3N$ (182 μL, 132 mg, 1.31 mmol). The resulting mixture was stirred for 18.5 h. DCM (20 mL) and $H_2O$ (20 mL) were added and the pH of the aqueous layer was adjusted to pH 4 with an aqueous solution of HCl (1N). After separation, the aqueous layer was extracted with DCM (20 mL). The combined organic layers were dried ($Na_2SO_4$) and concentrated. The residue was purified with silica gel chromatography (MeOH in DCM 0 to 0%). The product 4 was obtained as a colorless oil (113 mg, 0.20 mmol, 75%) $^1H$ NMR (400 MHz, $CDCl_3$) δ (ppm) 4.58-4.38 (m, 1H), 4.28 (d, 2H, J=8.5 Hz), 4.12-3.98 (m, 2H), 3.75-3.60 (m, 4H), 3.40-3.25 (m, 2H), 2.36-2.16 (m, 6H), 1.63-1.49 (m, 2H), 1.47-1.35 (m, 4H), 1.06-0.84 (m, 8H).

To a solution of 4 (70 mg, 0.12 mmol) in DMF (1 mL) were added EEDQ (36 mg, 0.15 mmol and 4-aminobenzyl alcohol (18 mg, 0.15 mmol). The mixture was stirred for 22 h, diluted with DCM (5 mL) and concentrated. The residue was purified with silica gel chromatography (MeOH in DCM 0 to 20%). The combined column fractions were concentrated, and the residue was diluted with EtOAc (6 mL) and concentrated (2×). The product 5 was obtained as a white solid (32 mg, 0.047 mmol, 39%). $^1H$ NMR (400 MHz, $CDCl_3$) δ (ppm) 8.84 (s, 0.3H), 8.79 (s, 0.7H), 7.58-7.42 (m, 2H), 7.28-7.16 (m, 2H), 6.40-6.32 (m, 0.3H), 6.24-6.14 (m, 0.7H)$^+$, 6.09 (d, J=7.4 Hz, 0.3H), 5.94 (d, J=7.2 Hz, 0.7H), 4.74-4.63 (m, 1H), 4.59 (s, 2H), 4.40-3.90 (m, 5H), 3.70-3.45 (m, 4H), 3.29-3.14 (m, 2H), 2.34-2.06 (m, 6H), 1.57-1.30 (m, 6H), 1.01-0.88 (m, 8H).

To a solution of 5 (32 mg, 0.047 mmol) in DMF (0.5 mL) were added bis(4-nitrophenyl) carbonate (14 mg, 0.047 mmol) and $Et_3N$ (20 μL, 14 mg, 0.141 mmol). The mixture was stirred for 17.5 h, diluted with DCM (5 mL) and concentrated. The residue was purified with silica gel chromatography (MeOH in DCM 0 to 20%). The product was obtained as a colorless oil (22 mg, 0.026 mmol, 55%) $^1H$ NMR (400 MHz, $CDCl_3$) δ (ppm) 8.89 (s, 0.3H), 8.80 (s, 0.7H), 8.29-8.23 (m, 2H), 7.71-7.61 (m, 2H), 7.40-7.32 (m, 4H), 7.12-7.01 (m, 1H), 6.40-6.30 (m, 0.3H), 6.22-6.11 (m, 0.7H), 5.95-5.82 (m, 1H), 5.23 (s, 2H), 4.76-4.65 (m, 1H), 4.45-3.90 (m, 5H), 3.71-3.56 (m, 4H), 3.31-3.21 (m, 2H), 2.34-2.12 (m, 6H), 1.57-1.30 (m, 6H), 1.02-0.90 (m, 8H).

Example 1-2: Synthesis of BCN-Activated Carbonate Derivatives 31-33 with Cleavable Linker

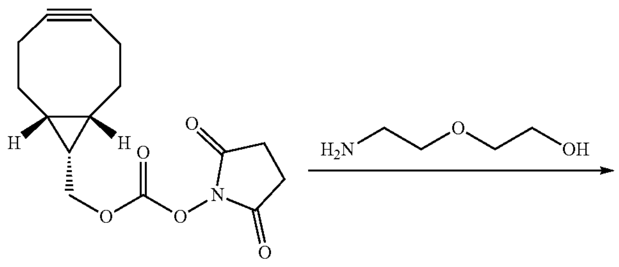

29-1

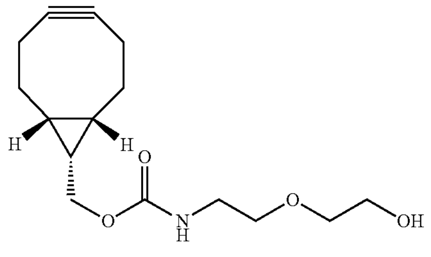

29-2

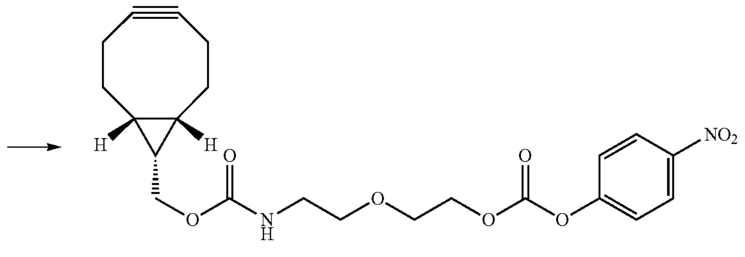

30

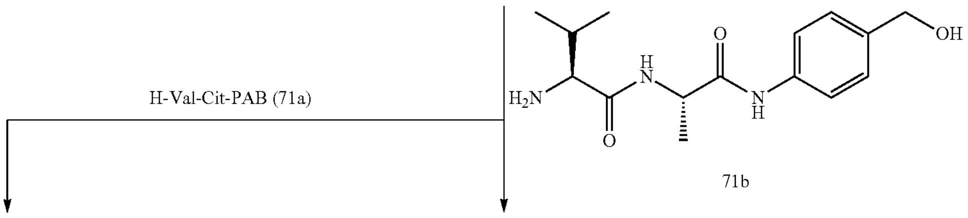

71b

-continued

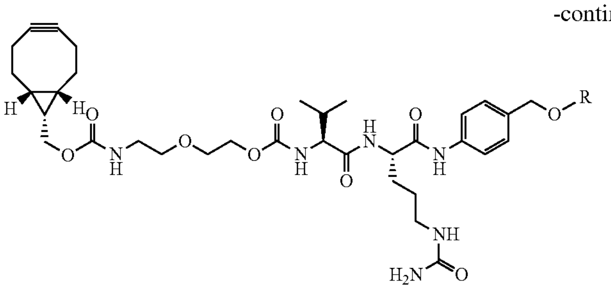

72 R = H

31 R = 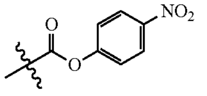

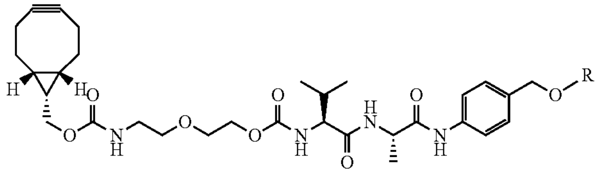

73 R = H

32 R = 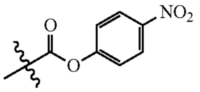

33 R = 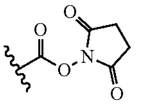

(1R,8S,9s)-bicyclo[6.1.0]non-4-yn-9-ylmethyl N-succinimidyl carbonate (29-1, 16.35 g, 56.13 mmol, 1 eq.) was dissolved in DCM (400 ml). 2-(2-aminoethoxy)ethanol (6.76 ml, 67.35 mmol, 1.2 eq.) was then added followed by triethylamine (23.47 ml, 168.39 mmol, 3 eq.). The resulting pale yellow solution was stirred at rt for 90 min. The reaction mixture was concentrated in vacuo and the residue was co-evaporated once with acetonitrile (400 mL). The resulting oil was dissolved in EtOAc (400 mL) and washed three times with water (200 mL). The organic layer was concentrated in vacuo and the residue was purified by flash column chromatography over silica (50%→88% EtOAc in heptane) to give the product as a pale yellow oil (11.2 g, 39.81 mmol, 71%). 1H-NMR (400 MHz, $CDCl_3$) δ 5.14-4.89 (bs, 1H). 4.17 (d, J=8.0 Hz, 2H,), 3.79-3.68 (m, 2H), 3.64-3.50 (m, 4H), 3.47-3.30 (m, 2H), 2.36-2.14 (m, 6H), 2.03-1.84 (bs, 1H), 1.68-1.49 (m, 2H), 1.37 (quintet, J=8.0 Hz, 1H), 1.01-0.89 (m, 2H).

To a solution of N-(1R,8S,9s)-bicyclo[6.1.0]non-4-yn-9-ylmethyloxycarbonyl 1-amino-3-oxapentan-5-ol (29-2, 533 mg, 1.92 mmol) in DCM (30 mL) were added 4-nitrophenyl chloroformate (594 mg, 2.95 mmol) and $Et_3N$ (1.13 mL, 824 mg, 5.91 mmol). The resulting mixture was stirred for 2 h and concentrated. The residue was purified by silica chromatography (20%→50% EtOAc in heptane). The desired product was obtained as slightly yellow oil (723 mg, 1.62 mmol, 82%). 1H NMR (400 MHz, $CDCl_3$) δ (ppm) 8.32-8.25 (m, 2H), 7.43-7.37 (m, 2H), 5.05 (bs, 1H), 4.46-4.41 (m, 2H), 4.15 (d, J=8.0 Hz, 2H), 3.80-3.75 (m, 2H), 3.60 (t, J=5.1 Hz, 2H), 3.41 (q, J=5.3 Hz, 2H), 2.35-2.15 (m, 6H), 1.65-1.47 (m, 2H), 1.35 (quintet, J=8.3 Hz, 1H), 1.01-0.88 (m, 2H).

To a solution of 30 (0.24 g, 0.53 mmol) in DMF (5 mL) were added $NH_2$-Val-Cit-PAB-OH (181 mg, 0.48 mmol) and $Et_3N$ (222 μL, 161 mg, 1.59 mmol). The resulting mixture was stirred for 18 h and concentrated. The residue was purified by silica chromatography (DCM→20% MeOH in DCM) and the desired product was obtained as a white solid (288 mg, 0.42 mmol, 88%). 1H NMR (400 MHz, $CDCl_3$) δ (ppm) 9.98-9.93 (bs, 1H), 8.06 (d, J=7.4 Hz, 1H), 7.58-7.50 (m, 2H), 7.29-7.20 (m, 3H), 7.12 (t, J=5.5 Hz, 1H), 5.98 (t, 1H, J=5.9 Hz), 5.41 (s, 2H), 5.10 (t, 1H, 5.8 Hz), 4.42 (d, 2H, J=5.5 Hz), 4.44-4.36 (m, 1H), 4.08-4.00 (m, 4H), 3.93-3.85 (m, 1H), 3.62-3.50 (m, 2H), 3.47-3.37 (m, 2H), 3.14-2.88 (m, 2H), 2.29-2.07 (m, 6H), 2.03-1.90 (m, 1H), 1.76-1.20 (m, 6H), 1.26 (quintet, J=8.7 Hz, 1H), 0.87 (d, J=6.8 Hz, 3H), 0.83 (d, J=6.8 Hz, 3H).

To a solution of 72 (100 mg, 0.15 mmol) in DMF (5 mL) were added bis(4-nitrophenyl) carbonate (53 mg, 0.17 mmol) and $Et_3N$ (63 μL, 46 mg, 0.45 mmol). The mixture was stirred for 41 h, concentrated and purified by silica gel chromatography (DCM→20% MeOH in DCM). The desired product was obtained as a colorless film (9.1 mg, 10.7 μmol, 7.1%). LCMS (ESI+) calculated for $C_{41}H_{54}N_7O_{13}^+$ (M+$H^+$) 852.38 found 852.70.

To a colourless solution of 10 (502 mg, 973 μmol) in DMF (5.2 mL) was added piperidine (260 μL, 2.63 mmol). The reaction mixture was stirred at room temperature for 75 minutes and then conc. in vacuo. The residue was purified by silica chromatography (1→20% MeOH in DCM) affording the product 71b (88% pure by NMR, 333 mg, quant.) as a colorless oil. 1H NMR (400 MHz, $CDCl_3$) δ (ppm) 7.42 (d, J=8.6 Hz, 2H), 7.19 (d, J=8.6 Hz, 2H), 4.45 (s, 2H), 4.40 (q, J=7.0 Hz, 1H), 3.05 (d, J=5.6 Hz, 1H), 1.94-1.80 (m, 1H), 1.33 (d, J=7.2 Hz, 3H), 0.87 (d, J=6.9 Hz, 3H), 0.81 (d, J=6.8 Hz, 3H).

To a solution of 30 (138 mg, 0.31 mmol) in DMF (2 mL) were added a solution of $NH_2$—Val-Ala-PAB-OH (71b) (91 mg, 0.31 mmol) in DMF (1 mL) and $Et_3N$ (130 μL, 94 mg, 0.93 mmol). The mixture was left standing for 19 h and concentrated. The residue was purified by silica chromatograph (DCM followed by DCM→15% MeOH in DCM). The desired product was obtained as a white solid (146 mg, 0.24 mmol, 77%). 1H NMR (400 MHz, $CDCl_3$) δ (ppm) 8.80-8.45 (m, 1H), 7.58-7.42 (m, 2H), 7.34-7.20 (m, 2H), 6.92-6.83 (m, 1H), 5.85-5.10 (m, 2H), 4.67 (quintet, J=7.2 Hz, 1H), 4.64-4.60 (m, 2H), 4.32-3.98 (m, 5H), 3.80-3.20 (m, 6H), 2.45-2.10 (m, 6H), 1.63-1.49 (m, 2H), 1.46 (d, J=7.0 Hz, 3H) 1.42-1.29 (m, 1H), 0.98 (d, J=6.8 Hz, 3H), 0.94 (d, J=6.5 Hz, 3H), 1.08-0.86 (m, 2H).

To a solution of 73 (146 mg, 0.243 mmol) in DMF (4.4 mL) were added bis(4-nitrophenyl) carbonate (81 mg, 0.27 mmol) and $Et_3N$ (102 μL, 74 mg, 0.73 mmol). The resulting mixture was stirred for 3.5 h., diluted with DMF (1 mL) and concentrated. The residue was purified by flash column chromatography (DCM→10% MeOH in DCM). The desired product was obtained as a colorless oil (216 mg, 0.28 mmol). The product still contained residual DMF and DCM, 1H NMR (400 MHz, $CDCl_3$) δ (ppm) 8.95-8.67 (m, 1H), 8.30-8.23 (m, 2H), 7.66-7.58 (m, 2H), 7.42-7.33 (m, 4H), 6.89-6.79 (m, 1H), 5.80-5.05 (m, 2H), 5.26-5.20 (s, 2H), 4.66 (quintet, J=7.3 Hz, 1H), 4.48-3.96 (m, 3H), 4.15 (d, J=8.0 Hz, 2H), 3.75-3.25 (m, 6H), 2.35-2.13 (m, 6H), 1.65-1.50 (m, 2H), 1.47 (d, J=7.1 Hz, 3H), 1.41-1.29 (m, 1H), 0.99 (d, J=6.8 Hz, 3H), 0.94 (d, J=6.8 Hz, 3H), 1.03-0.88 (m, 2H).

To a solution of 73 (86.5% pure by qNMR, 65.2 mg, 94 μmol, 1.00 equiv.) in mixture of dry DCM/MeCN (1:1, 3 mL) was added DSC (48.1 mg, 188 μmol, 2.00 equiv.), followed by DiPEA (32.6 μL, 197 μmol, 2.1 equiv.). The resulting colorless solution was stirred at rt for 3.5 hours and then additional DSC (24.3 mg) was added. The reaction mixture was stirred for an additional 1.5 hours and was then diluted with DCM (30 mL) and washed with $H_2O$ (10 mL). The aqueous layer was extracted with DCM (15 mL) and the combined organic layers were dried over $Na_2SO_4$ and conc. in vacuo. The residue was purified by silica chromatography (0→10% MeOH in DCM). The desired product was obtained as a white foam ((~75% pure, 56.5 mg, 57.1 μmol, 61% yield). LCMS (ESI+) calculated for $C_{36}H_{48}N_5O_{12}^+$ ($M+H^+$) 742.33, found 742.22.

Example 1-3: Synthesis of BCN-Activated Carbonate Derivative 34 with Cleavable Linker 32
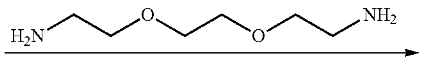
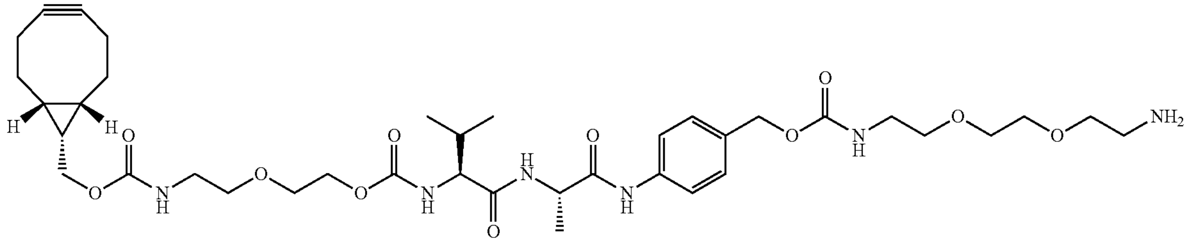
34

To a solution of 32 (9.0 mg, 12 μmol) in DMF (200 μL) was added 2,2'-(ethylenedioxy)bis(ethylamine) (8.6 μL, 8.7 mg, 59 μmol). The mixture was left for 19 h and purified by RP-HPLC (C18, 5%→90% MeCN (0.1% formic acid) in H2O (0.1% formic acid). The combined fractions were passed through an SPE ($HCO_3$—) column and concentrated. The residue was purified in DMF (300 μL) and purified by RP-HPLC (C18, 5%→90% MeCN in $H_2O$). The desired product was obtained as a colorless film (3.9 mg, 5.0 μmol). LCMS (ESI+) calculated for $C_{38}H_{59}N_6O_{11}^+$ ($M+H^+$) 775.42, found 775.55.

Example 1-4: Synthesis of Activated Carbonate Derivative 35 with Cleavable Linker

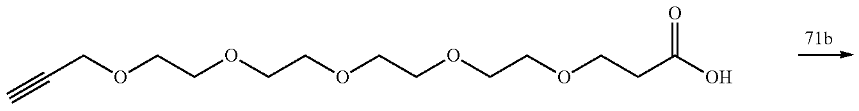

74
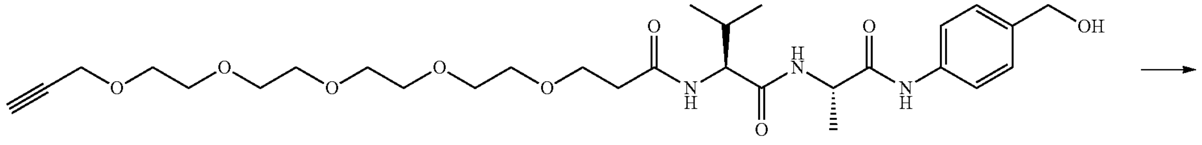
75
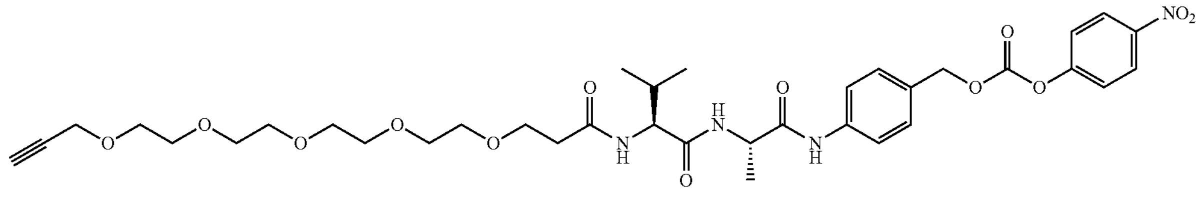
35

To a solution of alkyne-$PEG_4$-NHS ester (52 mg, 130 μmol) in DMF (2 mL) were added 71b (46 mg, 155 μmol) and $Et_3N$ (54 μL, 39 mg, 390 μmol). The resulting mixture was stirred for 3.5 h, diluted with DMF (0.5 mL) and concentrated. The residue was purified by silica chromatography (DCM→15% MeOH in DCM). The desired product was obtained as a white solid (57 mg, 76%). 1H NMR (400 MHz, $CDCl_3$) δ (ppm) 8.66 (bs, 1H), 7.73-6.65 (m, 2H), 7.33-7.25 (m, 2H), 7.20 (d, J=7.9 Hz, 1H), 7.16 (d, J=6.8 Hz, 1H), 4.68 (quintet, J=7.5 Hz, 1H), 4.62 (s, 2H), 4.22 (dd, J=5.7 Hz, 6.8 Hz, 1H), 4.18 (d, J=2.4 Hz, 2H), 3.82 (dt, J=9.7 Hz, 3.2 Hz, 1H), 3.72-3.50 (m, 17H), 2.71-2.61 (m, 1H), 2.51-2.41 (m, 1H), 2.43 (t, J=2.4 Hz, 1H), 2.31-2.21 (m, 1H), 1.44 (d, J=7.2 Hz, 3H), 1.01 (d, J=6.9 Hz, 3H), 0.98 (d, J=6.9 Hz, 3H).

To a solution of 75 in DMF (1.5 mL) was added bis(4-nitrophenyl) carbonate (45 mg, 0.147 mmol). The mixture was stirred for 15 min, $Et_3N$ (41 μL, 30 mg, 0.294 mmol) was added and the mixture was stirred for 4 h. After dilution with DMF (0.5 mL), the mixture was concentrated. The residue was purified by silica gel chromatography (DCM→15% MeOH in DCM). The desired compound was obtained as a white solid (57 mg, 0.077 mmol, 78%) 1H NMR (400 MHz, $CDCl_3$) δ (ppm) 8.90 (bs, 1H), 8.27-8.21 (m, 2H), 7.76-7.70 (m, 2H), 7.38-7.32 (m, 5H), 7.23 (d, J=6.8 Hz, 1H), 5.21 (s, 2H), 4.69 (quintet, J=7.4 Hz, 1H), 4.27 (dd, J=5.9 Hz, 6.6 Hz, 1H), 3.70-3.55 (m, 17), 2.66 (ddd, J=13.4 Hz, J=9.0 Hz, J=4.2 Hz, 1H), 2.48 (ddd, J=14.6 Hz, J=5.6 Hz, J=3.6 Hz, 1H), 2.42 (t, J=2.4 Hz, 1H), 2.29-2.16 (m, 1H), 1.43 (d, J=7.2 Hz, 3H), 0.99 (d, J=7.1 Hz, 3H), 0.97 (d, J=7.2 Hz, 3H).

Example 1-5: Synthesis of Activated Carbonate Derivative 36 with Cleavable Linker

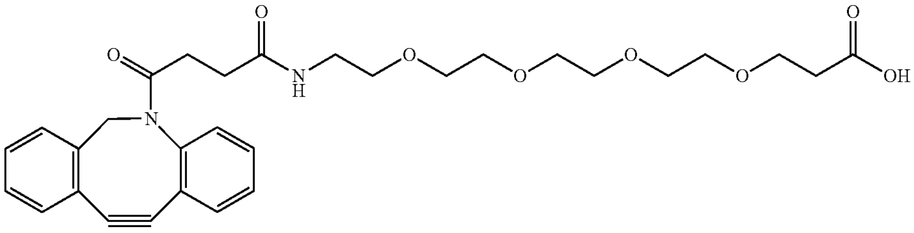

76

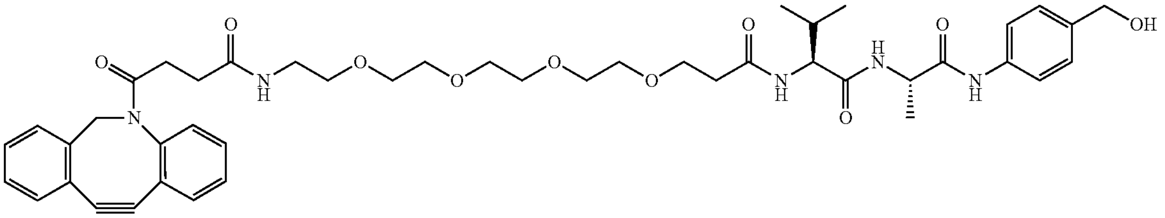

77

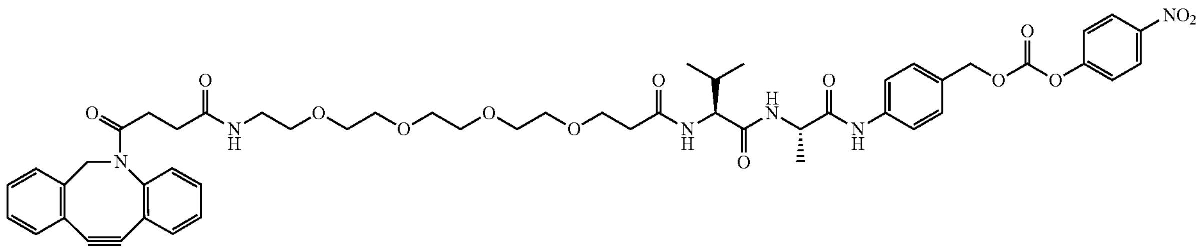

36

To a solution of DBCO-$PEG_4$-OSu (63 mg, 97 μmol) in DMF (2 mL) were added a solution of $NH_2$-Val-Ala-PAB-OH (30 mg, 0.10 mmol) in DMF (0.5 mL) and $Et_3N$ (41 μL, 29 mg, 0.29 mmol). The mixture was stirred for 100 min and a solution of $NH_2$—Val-Ala-PAB-OH (7.8 mg, 27 μmol) in DMF (0.15 mL) was added. The mixture was stirred for 45 min, diluted with DMF (0.5 mL) and concentrated. The residue was purified by silica gel column chromatography (DCM→15% MeOH in DCM). The desired product was obtained as a colorless film (94 mg, 0.11 mmol, quant.) 1H NMR (400 MHz, $CDCl_3$) δ (ppm) 8.79-8.76 (bs, 1H), 7.71-7.62 (m, 3H), 7.42-7.21 (m, 9H), 6.70 (t, J=5.8 Hz, ½H), 6.94 (t, J=6.3 Hz, ½H), 5.12 (d, J=14 Hz, 1H), 4.73-4.62 (m, 1H), 4.62-4.59 (m, 2H), 4.22-4.16 (m, 1H), 3.85-3.15 (m, 16H), 2.65-1.90 (m, 9H), 1.46-1.39 (m, 3H), 1.02-0.94 (m, 6H).

To a solution of 77 (94 mg, 0.11 mmol) in DMF (1.5 mL) was added bis(4-nitrophenyl) carbonate (38 mg, 0.12 mmol). The resulting mixture was stirred for 20 min and $Et_3N$ (46 μL, 33 mg, 0.33 mmol) was added. The mixture was stirred for 105 min and bis(4-nitrophenyl) carbonate was added (10 mg, 33 μmol) was added. The resulting mixture was stirred for 1 h and concentrated. The residue was purified by silica column chromatography (DCM and then DCM→10% MeOH in DCM). The desired product was obtained as a colorless thick oil (79 mg, 80 μmol, 72%). LCMS (ESI+) calculated for $C_{52}H_{61}N_6O_{14}^+$ ($M+H^+$) 993.42, found 993.71.

Example 1-6: Synthesis of BCN-Activated Carbonate Derivative 41 and BCN-$PEG_3$-Gly 42 with Non-Cleavable Linker 29-1

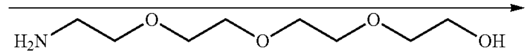

78

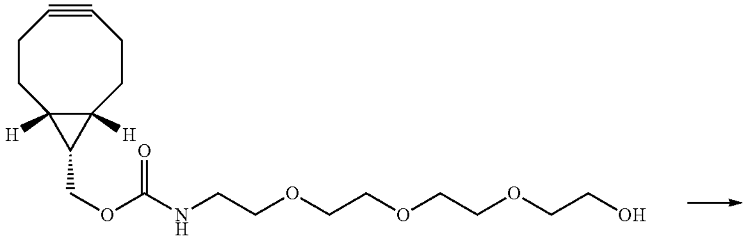

79

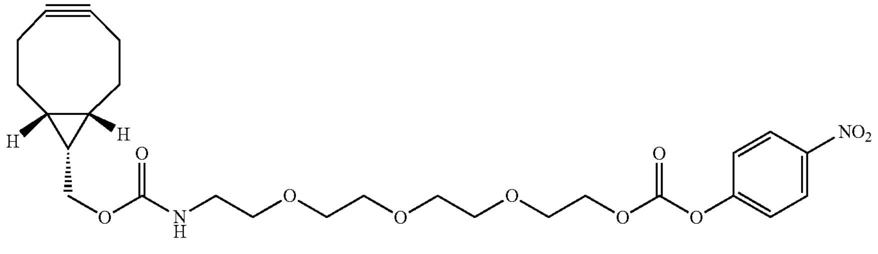

41

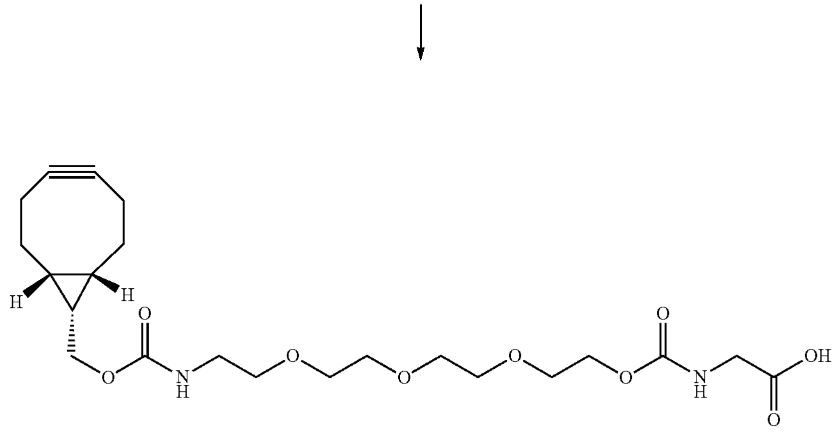

42

To a solution of 2-(2-(2-(2-aminoethoxy)ethoxy)ethoxy) ethanol (0.50 g, 2.6 mmol) was added BCN-OSu (29-1, 0.69 g, 2.3 mmol) and $Et_3N$ (0.97 mL, 0.70 g, 7.0 mmol). The resulting mixture was mixture was stirred for 80 min and saturated aqueous $NH_4Cl$ (60 mL) was added. After separation, the aqueous phase was extracted with DCM (60 mL). The combined organic layers were dried ($Na_2SO_4$) and concentrated. The residue was purified with silica gel chromatography (DCM→10% MeOH in DCM), which yielded 578 mg (1.56 mmol, 67%) of the desired product. 1H NMR (400 MHz, $CDCl_3$) δ (ppm) 5.98-5.85 (bs, 1H), 4.14 (d, J=8.0 Hz, 2H), 3.78-3.59 (m, 12H), 3.58-3.52 (m, 2H), 3.42-3.32 (m, 2H), 3.19-3.06 (bs, 1H), 2.35-2.16 (m, 6H), 1.70-1.50 (m, 2H), 1.36 (quintet, J=8.6 Hz, 1H), 0.99-0.87 (m, 2H).

To a solution of 79 (0.58 g, 1.6 mmol) in DCM (100 mL) were added 4-nitrophenyl chloroformate (0.35 g, 1.7 mmol) and $Et_3N$ (0.66 mL, 0.48 g, 4.7 mmol). The resulting mixture was stirred for 18 h and concentrated. The residue was purified by silica chromatography (20%→70% EtOAc in heptane). The product was obtained as a colorless thick oil (563 mg, 1.05 mmol, 67%). 1H NMR (400 MHz, $CDCl_3$) δ (ppm) 8.31-8.25 (m, 2H), 7.42-7.36 (m, 2H), 5.25-5.16 (m, 1H), 4.47-4.42 (m, 2H), 4.15 (d, J=8.1 Hz, 2H), 3.84-3.80 (m, 2H), 3.74-3.61 (m, 8H), 3.59-3.53 (m, 2H), 3.42-3.32 (m, 2H), 2.35-2.16 (m, 6H), 1.66-1.51 (m, 2H), 1.35 (quintet, J=8.8 Hz, 1H), 1.00-0.98 (m, 2H).

To a solution of 41 (106 mg, 0.20 mmol) in MeCN (5 mL) were added a solution of glycine (22 mg, 0.30 mmol) in $H_2O$ (0.22 mL) and $Et_3N$ (61 mg, 84 μL). The mixture was stirred for 67 h and concentrated. The residue was purified by silica chromatography (0%→20% MeOH in DCM). The desired product was obtained as a colorless oil (93 mg, 0.20 mmol, 100%). 1H NMR (400 MHz, $CDCl_3$) δ (ppm) 5.56-5.40 (m, 1H), 4.30-4.12 (m, 2H), 4.14 (d, J=7.9 Hz, 2H), 3.92-3.48 (m, 14H), 3.42-3.30 (m, 2H), 2.35-2.15 (m, 6H), 1.65-1.50 (m, 2H), 1.40-1.30 (m, 1H), 1.00-0.86 (m, 2H).

Example 1-7: Synthesis of BCN-Activated Carbonate Derivative 43 with Non-Cleavable Linker

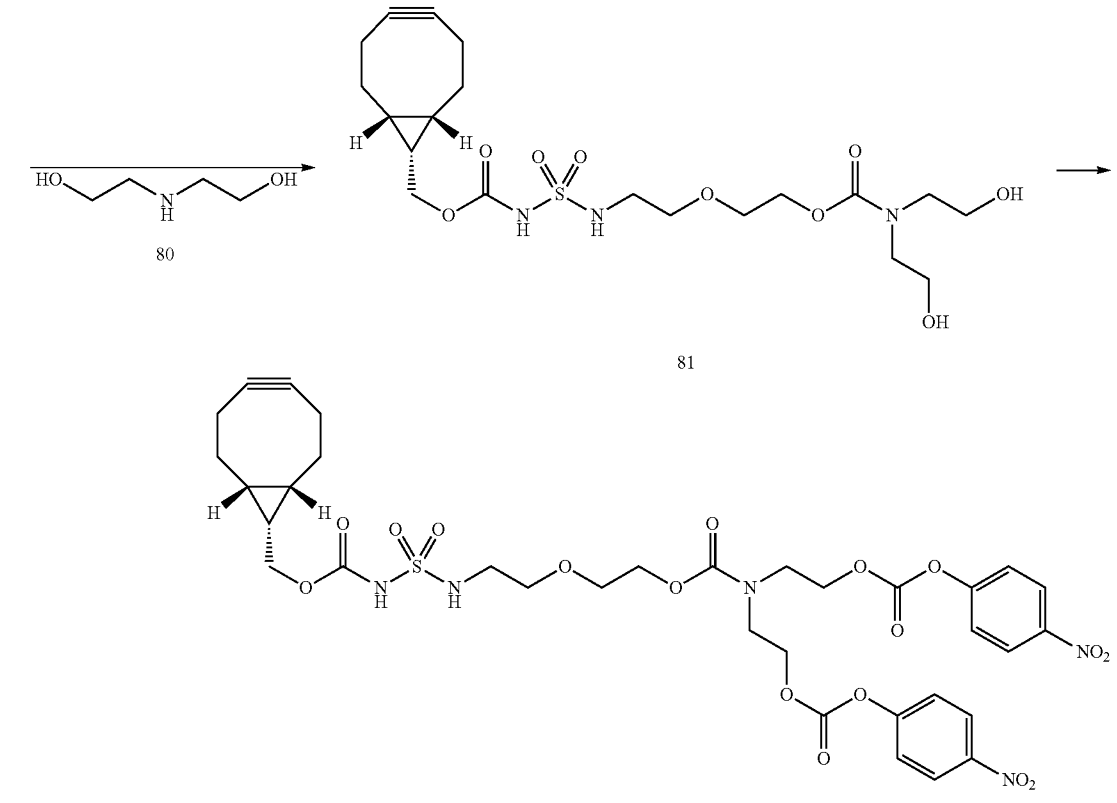

3

80

81

43

To a solution of 3 (3.28 g, 6.24 mmol) in DCM (150 mL) were added a solution of diethanolamine (0.78 g, 7.49 mmol, 1.2 equiv.) in DMF (6 mL) and $Et_3N$ (2.61 mL, 1.89 g, 18.72 mmol, 3 equiv.). The mixture was stirred for 25 h and saturated aqueous $NH_4Cl$ (~240 mL) was added. The pH of the water layer (~7.7) was adjusted to pH 5.8 with 1M aq. HCl, while stirring the biphasic system vigorously until the pH remained stable at pH 5.8. The biphasic system was then separated, and the water layer was extracted with DCM (100 mL, 2×50 mL). The combined organic layers were dried ($Na_2SO_4$) and conc. in vacuo. The residue was purified by silica chromatography (120 g SiO2, 0→15% MeOH in DCM). The fractions which contained the desired product were combined and concentrated, affording intermediate 81 as a colorless oil (2.63 g, (2.28 g, 4.64 mmol, 74% yield when corrected for remaining solvent (DCM))). LCMS (ESI+) calculated for $C_{20}H_{33}N_3NaO_9S^+$ (M+$Na^+$) 514.18, found 513.97.

To a solution of 81 (2.27 g, 4.62 mmol) in DCM (80 mL) were added 4-nitrophenyl chloroformate (2.14 g, 10.6 mmol, 2.30 equiv.) and $Et_3N$ (3.70 mL, 26.5 mmol, 5.7 equiv.). The mixture was stirred for 4.5 h and concentrated. The residue was purified by silica chromatography (120 g SiO2, 50%→100% EtOAc in heptane with 1% AcOH in the eluent) followed by a second column (50%→100% EtOAc in heptane with 1% AcOH in the eluent). The fractions containing pure product were combined and conc. in vacuo. The residue was taken up in DCM, followed by the addition of some heptane and the resulting mixture was conc. in vacuo. Note: care was taken to prevent uncontrolled foaming during the concentration step by gradually decreasing the pressure. Upon complete concentration the product 43 was obtained as a white solid (2.1 g, 88% pure, 49% yield). LCMS (ESI+) calculated for $C_{34}H_{39}N_5NaO_{17}S^+$ (M+Na$^+$) 844.20, found 844.11. 1H NMR (400 MHz, $CDCl_3$) δ (ppm) 8.28 (d, J=9.2 Hz, 4H), 7.40 (d, J=9.0 Hz, 4H), 5.71 (t, J=5.8 Hz, 1H), 4.54-4.44 (m, 4H, 4.33 (m, 2H), 4.26 (d, J=8.3 Hz, 2H), 3.80-3.70 (m, 4H), 3.70-3.64 (m, 2H), 3.60 (t, J=4.8 Hz, 2H), 3.32-3.26 (m, 2H), 2.35-2.15 (m, 6H), 1.57-1.47 (m, 2H), 1.37 (p, J=8.7 Hz, 1H), 1.05-0.93 (m, 2H).

Example 2. Synthesis of Fmoc-Glycine Anhydride 7 and Glycine Derivative 8 of Calicheamicin

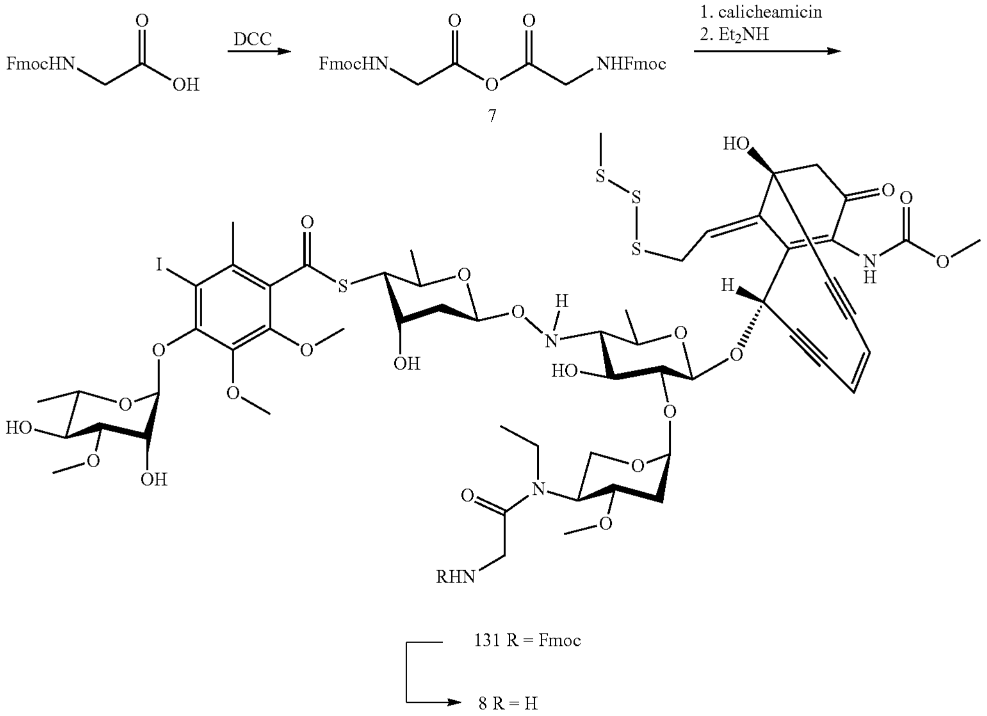

7

131 R = Fmoc

8 R = H

To a suspension of Fmoc-Gly-OH (100 mg, 0.34 mmol) in DCM (10 mL) were added DMF (0.5 mL) and N,N'-dicyclohexylcarbodiimide (35 mg, 0.17 mmol). The mixture was stirred for 15 min. and concentrated until DCM was evaporated. DMF (1.0 mL) was added to the residue and the resulting suspension contained the anhydride of Fmoc-Gly (7) was used in the next step without purification.

To a solution of calicheamicin $\gamma_1^I$ (5.0 mg, 3.7 μmol) in DMF (200 μL) was added 0.33 mL of the solution of 7. The mixture was left for 4 h and cooled to −20° C. After 2.5 days, a 10% solution of $Et_2NH$ in THF/$H_2O$ (25:1) was added (380 μL). After 1.5 h, the reaction mixture was diluted with a 1:1 mixture of $Et_2O$ and DCM (5 mL), dried ($Na_2SO_4$) and concentrated. The residue was purified by RP HPLC (Column 1: C18, 5%→90% MeCN (1% AcOH) in water (1% AcOH)) (Column 2: C18, 30%→90% MeCN (1% AcOH) in water (1% AcOH)). The product 8 was obtained as a slightly orange film (3.5 mg, 2.5 μmol, 68%). LCMS (ESI+) calculated for $C_{57}H_{78}IN_4O_{22}S_4^+$ (M+H$^+$) 1425.30 found 1425.51.

Example 3. Synthesis of BCN-Val-Cit-PABC-Gly-Calicheamicin

8

6

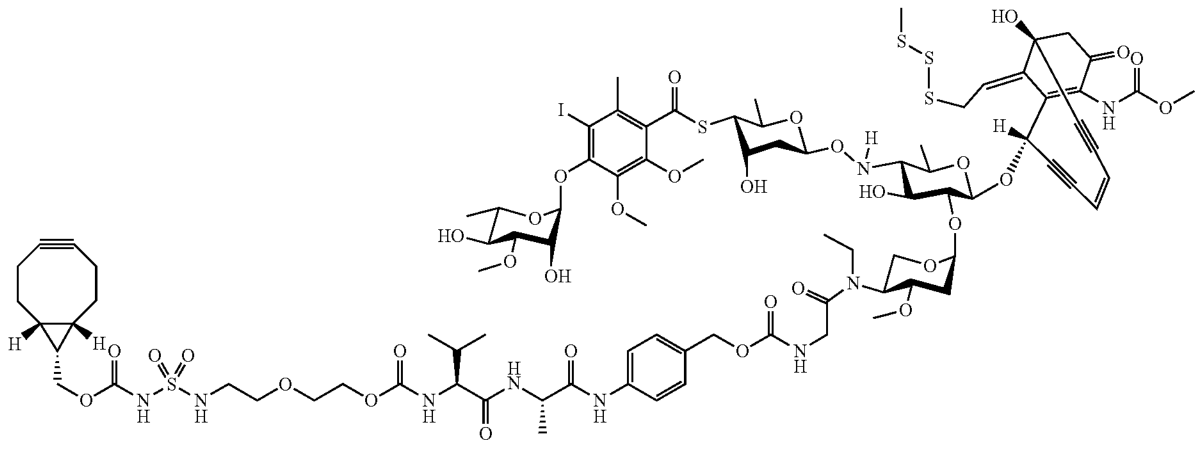

9

To a solution of 8 (3.4 mg, 2.4 μmol) in DMF (0.24 mL) were added a solution of 6 (2.0 mg, 2.4 μmol) in DMF (23 μL) and $Et_3N$. After 1 h. 2,2'-(ethylenedioxy)bis(ethylamine) (1.4 μL, 1.4 mg. 9.6 μmol) was added. After 1h. the mixture was diluted with DMF (100 μL) and purified by RP HPLC (C18, 30%→90% MeCN (1% AcOH) in water (1% AcOH)). The desired product 9 was obtained as a colorless film (2.2 mg, 1.0 μmol, 42%). LCMS ($ESI^+$) calculated for $C_{89}H_{121}IN_9O_{33}S_5^+$ ($M+H^+$) 2130.57. Calculated for fragments $C_{42}H_{62}N_7O_{14}S^+$ 920.41 found 920.64 and for $C_{47}H_{60}IN_2O_{19}S_4^+$1211.17 found 1211.29.

Example 4-1. Synthesis of BCN-Val-Ala-PABC-calicheamicin 101

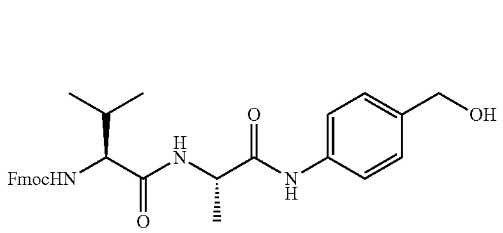

10

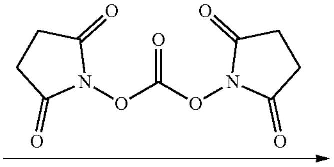

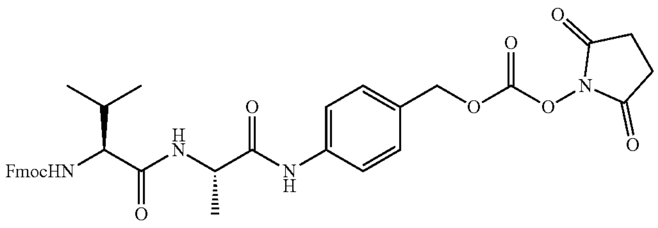

11

11 calicheamicin

-continued

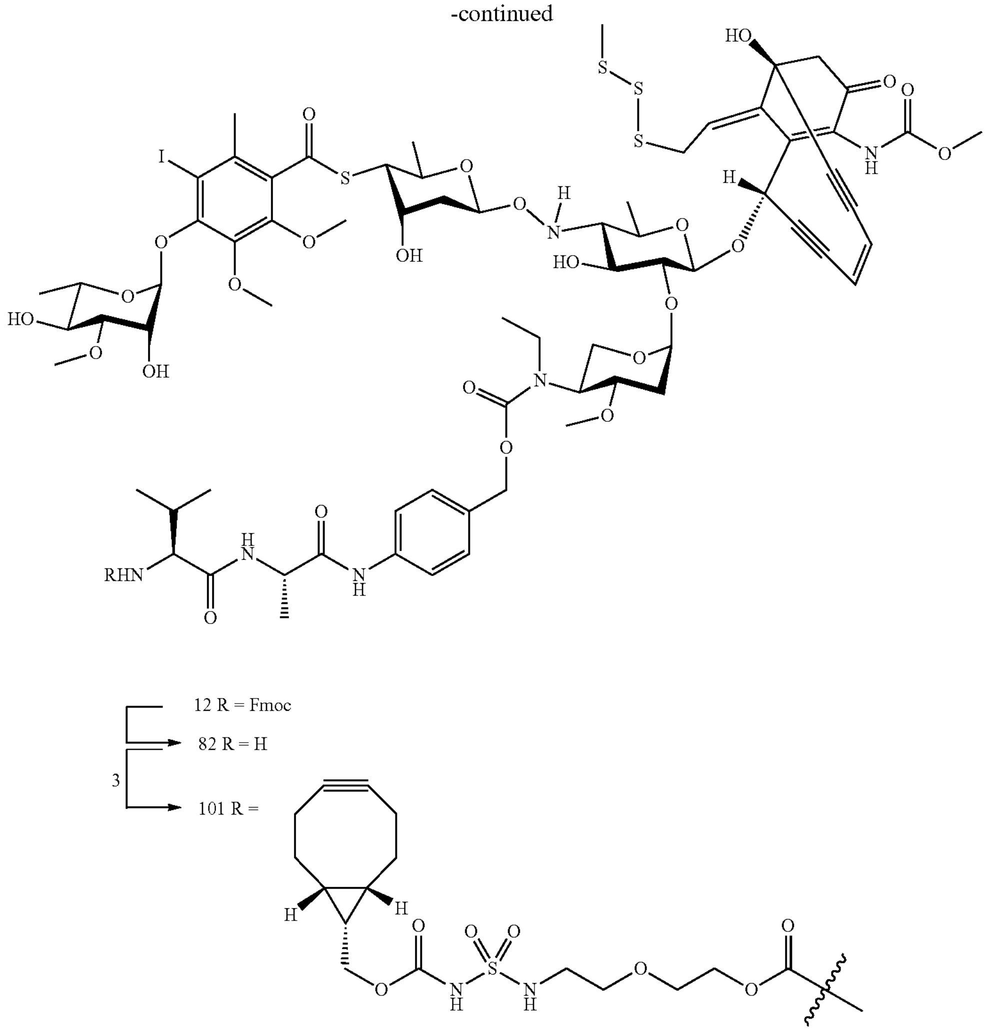

To a solution of Fmoc-Val-Ala-PAB-OH 10 (106 mg, 0.205 mmole) in DMF (1.0 mL) was added DSC (52.7 mg, 0.205 mmole) and DMAP (12.2 mg, 99.9 μmole) and the mixture was stirred for 2 h showing ~66% conversion by LC-MS analysis. Additional DSC (32.0 mg, 0.125 mmole) was added and the reaction mixture was stirred for another 20 min. and then conc. in vacuo. The resulting oil was dissolved in 1 mL of a mixture of DMF:DCM (1:9) and purified by silica gel column chromatography by elution with 50→80% EtOAc in heptane, yielding the desired carbonate 11 (32.7 mg, 49.8 μmole, 24%) as a white solid. LCMS ($ESI^+$) calculated for $C_{35}H_{36}N_4O_9Na^+$ ($M+Na^+$) 679.24 found 679.04.

To a solution of calicheamicin $\gamma_1^I$ (1.2 mg, 0.87 μmole) in DMF (24.0 μL) was added a solution of 11 (1.73 mg, 2.63 μmole) in DMF (6.0 μL) and the reaction was stirred at 37° C. for 24 h showing ~82% conversion by LC-MS analysis. The reaction mixture was diluted with DMF to ~170 μL and purified by RP HPLC (018, 30%→100% MeCN (1% AcOH) in water (1% AcOH)) to yield the desired product 12 as a white residue (1.0 mg, 0.52 μmole, 60%). LCMS ($ESI^+$) calculated for $C_{86}H_{106}IN_6O_{27}S_4^+$ ($M+H^+$) 1909.50 found 1909.54.

To a solution of 12 (23.6 mg, 11.6 μmol) in a mixture of THF:$H_2O$ (25:1, 5.5 mL) was added diethylamine (1.1 mL). The resulting reaction mixture was left at room temperature for 65 minutes and then conc. in vacuo and purified by silica chromatography (0→30% MeOH in DCM). The desired product was obtained as a reddish film (10.6 mg, 6.28 μmol, 51%) LCMS ($ESI^+$) calculated for $C_1H_{96}IN_6O_{25}S_4^+$ ($M+H^+$) 1687.43, found 1687.70.

To a solution of 82 (7.29 mg, 4.31 μmol, 1.0 equiv.) in DMF (185 μL) were added a solution of 3 (3.75 mg, 7.13 μmol, 1.65 equiv.) in DMF (16.4 μL) and $Et_3N$ (1.81 μL, 13.0 μmol, 3.0 equiv.). The mixture was mixed thoroughly and left standing for 0.5 h and then additional 3 (2.28 mg, 4.34 μmol, 1.0 equiv.) in DMF (10.0 μL) was added. The mixture was left standing for 18 hours and diluted with DCM to a total volume of 2.0 mL. This mixture was purified by silica chromatography (0→10% MeOH in DCM). The desired product 101 was obtained as a white residue (4.3 mg, 2.1 μmol, 48%). LCMS ($ESI^+$) calculated for $C_{96}H_{136}IN_9O_{35}S_4^{2+}$ ($M+2H^+$)/2 1037.28, found 1037.53.

Example 4-2: Synthesis of Fmoc-Val-Ala-PABC-OPFP 52 and Acylation of Calicheamicin to Give Carbamate 12

10

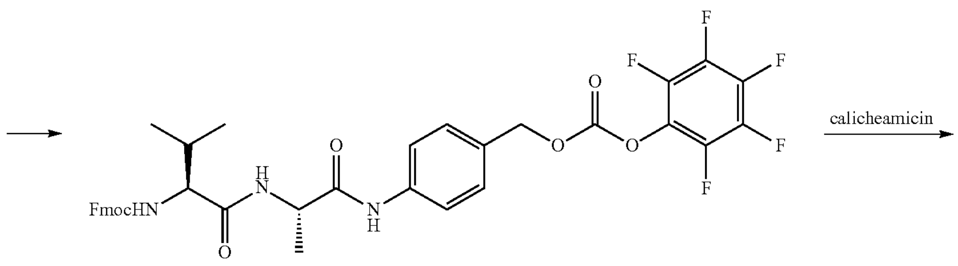

52

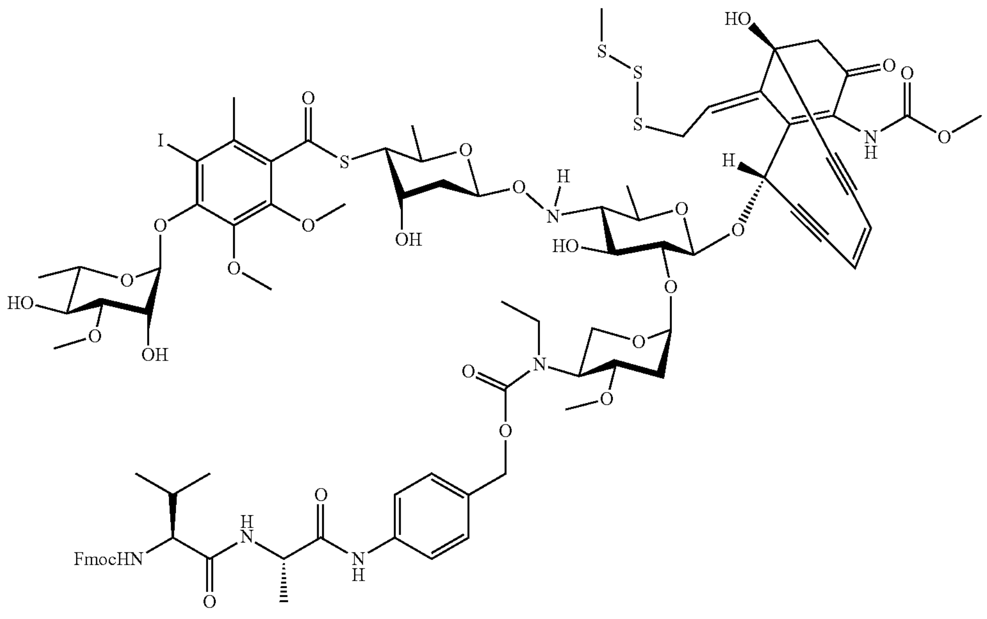

12

To a cooled (0° C.) solution of Fmoc-Val-Ala-PAB-OH (0.10 g, 0.19 mmol) in anhydrous DMF (1.0 mL) were added bis(pentafluorophenyl) carbonate (0.21 g, 0.53 mmol) and DiPEA (50 μL, 37 mg, 0.29 mmol). The mixture was stirred for 1 h, poured out in a mixture of $Et_2O$ (10 mL) and heptane (10 mL), cooled to 0° C., stirred for 1h and filtered. The product was obtained as a white solid (95 mg, 0.13 mmol, 69%). 1H NMR (400 MHz, DMSO-$d_6$) δ (ppm) 10.15-10.10 (bs, 1H), 8.27-8.18 (m, 1H), 7.93-7.84 (m, 2H), 7.79-7.60 (m, 4H), 7.50-7.26 (m, 6H), 5.34 (s, 2H), 4.48-4.38 (m, 1H), 4.36-4.16 (m, 3H), 3.98-3.86 (m, 1H), 2.07-1.92 (m, 1H), 1.32 (d, J=7.0 Hz, 3H), 0.90 (d, J=6.7 Hz, 3H), 0.86 (d, J=6.8 Hz, 3H). 19F NMR (400 MHz, DMSO-$d_6$) δ (ppm) −154.19 (d, J=20 Hz, 2F), −157.34 (t, J=23 Hz, 1F), −162.21 (dd, J=20 Hz, 23 Hz, 2F).

To a vial containing 52 (~76% pure, 69.3 mg, 80.2 μmol) was added a solution of calicheamicin $\gamma^1$ (23.8 mg, 17.4 μmol) in DMF (380 μL). The resulting solution was heated to 37° C. for 20 hours and then allowed to cool to room temperature. The reaction mixture was then diluted with DCM (4 mL) and purified by silica chromatography (0→8% MeOH in DCM). The fraction containing pure product were pooled, while the impure fractions were purified by a second silica gel chromatography purification (0→8% MeOH in DCM). The combination and concentration of the pure fractions from the first and second purification afforded the product as a white residue (23.6 mg, 12.4 μmol, 71%) LCMS ($ESI^+$) calculated for $C_{86}H_{106}IN_6O_{27}S_4^+$ ($M+H^+$) 1909.50, found 1909.65.

Example 4-3: Synthesis of BCN-(calicheamicin)$_2$ with Cleavable Linker 102
43
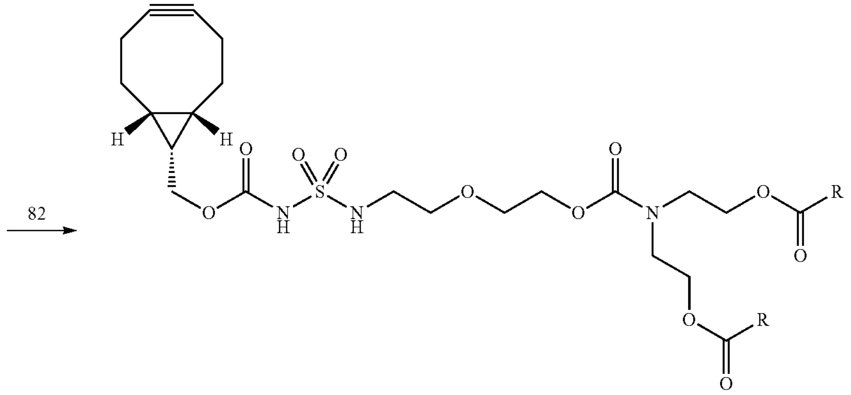
102
JH0392
R =
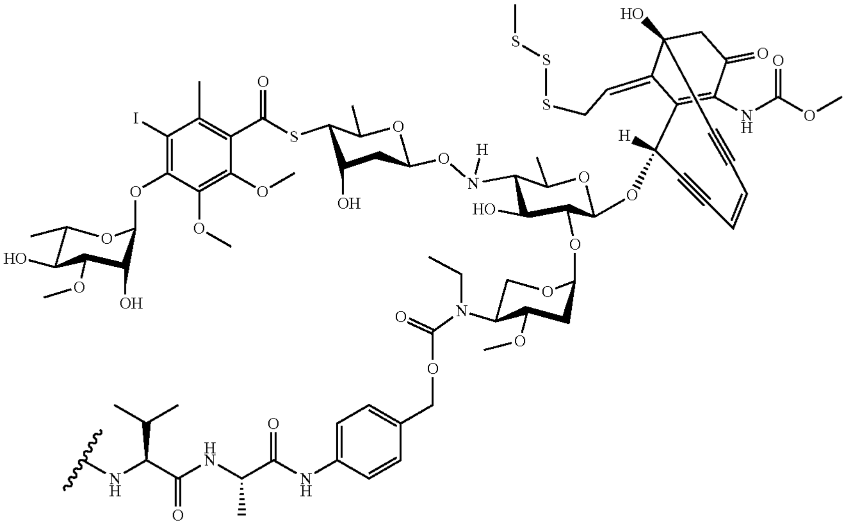

To a solution of 82 (0.81 mg, 0.48 μmol, 1.0 equiv.) in DMF (15 μL) was added a solution of 43 (197 μg, 240 nmol, 0.50 equiv.) in DMF (0.691 μL), followed by $Et_3N$ (0.20 μL, 3.0 equiv.). The resulting mixture was mixed thoroughly and left at rt for 2 days to give compound 102. LCMS ($ESI^+$) calculated for $C_{164}H_{221}I_2N_{15}O_{61}S_9^{2+}$ ($M+2H^+$)/2 1960.01, found 1959.99.

Example 4-5: Direct Acylation of Calicheamicin to Give BCN-Calicheamicin with Cleavable Linker 103

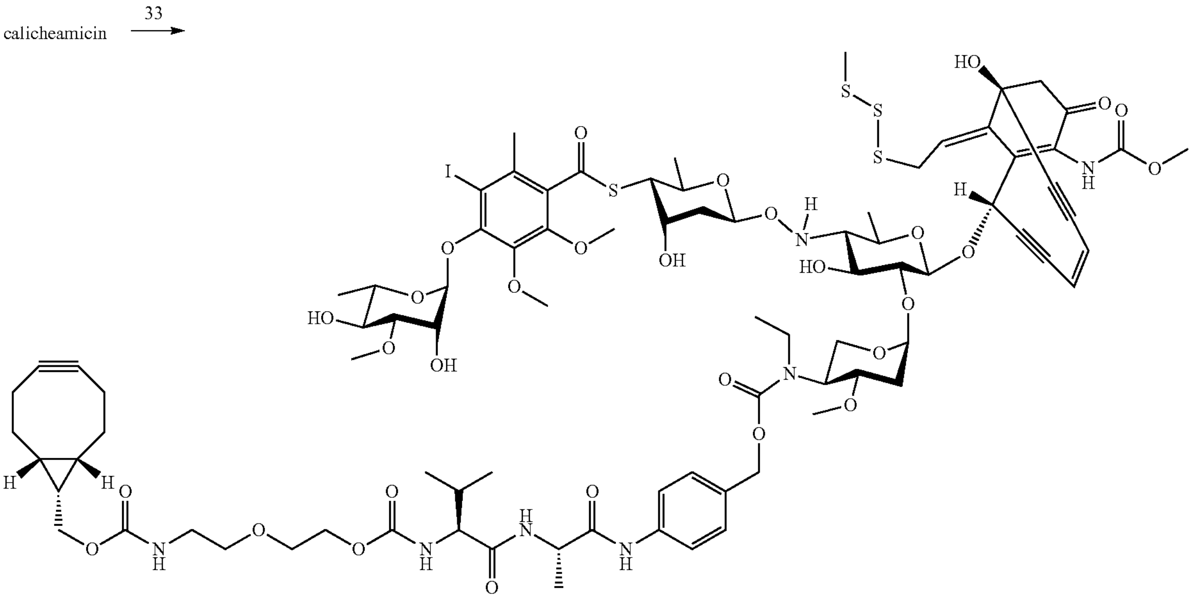

103

To a vial containing a solution of calicheamicin $\gamma^1$ (6.0 mg, 4.38 μmol) in DMF (120 μL) was added 33 (~75% pure, 10.8 mg, 14.6 μmol, 3.33 equiv.). The resulting solution was heated to 37° C. for 22 hours and then purified by silica chromatography (0→10% MeOH in DCM). The desired product was obtained as a white residue (2.3 mg, 1.2 μmol, 27% yield). LCMS (ESI+) calculated for $C_{87}H_{117}IN_7O_{30}S_4^+$ ($M+H^+$) 1994.58, found 1994.86.

Example 5: Trisulfide to Disulfide Exchange of Calicheamicin

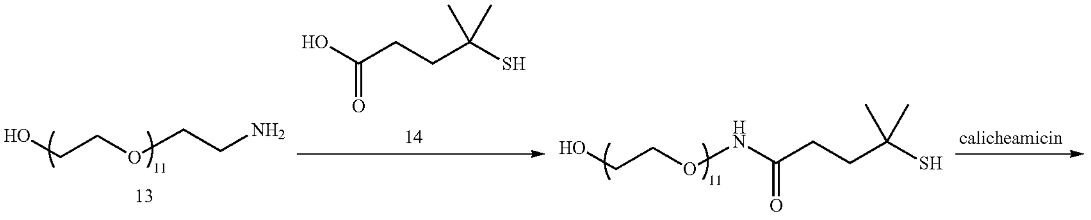

13

15

-continued

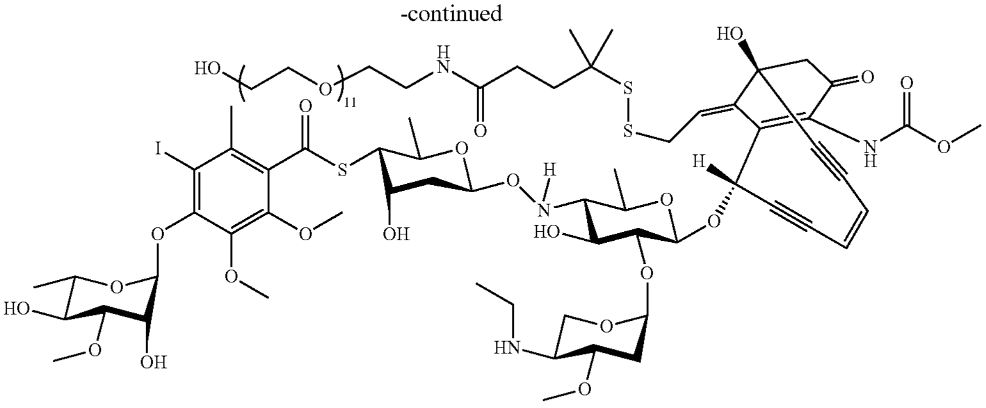

16

To a solution of 4-mercapto-4-dimethylpentanoic acid (14) (113 mg, 0.71 mmole) in dry DCM (2 mL) was added EDC·HCl (150 mg, 0.78 mmole) and the reaction mixture was stirred for 55 minutes before the addition of amine 13 (0.42 g, 0.78 mmole). The reaction mixture was stirred overnight, concentrated and purified by RP silica gel column chromatography (C18, 10→50% $H_2O$ in $CH_3CN$, with 0.1% formic acid), to give 15 (40.6 mg) as a yellow oil. LCMS ($ESI^+$) calculated for $C_{30}H_{62}NO_{13}S^+$ ($M+H^+$) 676.39 found 676.36.

A solution of calicheamicin $\gamma_1^I$ (4.6 mg, 3.36 μmole) in a mixture of MeCN (300 μL) and $H_2O$ (120 μL) was cooled to −15° C. and then added to a suspension of 15 (24.5 mg, 36.3 mole) in MeCN (200 μL) at −15° C. To the resulting mixture was added $Et_3N$ (5.1 μL, 36.6 μmole). The reaction mixture was left at −15° C. for 100 min and then allowed to warm to rt for ~15 min and then partially conc. in vacuo to remove MeCN. The residue was diluted with $H_2O$ (400 μL) and purified by RP HPLC (C18, 5%→90% MeCN (1% AcOH) in water (1% AcOH)), followed by a purification via gradient column chromatography (0→12% MeOH in DCM) to afford 16 as a colorless oil (3.2 mg, 1.63 μmol, 49%). LCMS ($ESI^+$) calculated for $C_{84}H_{132}IN_4O_{34}S_3^+$ ($M+H^+$) 1963.69 found 1963.94.

Example 5-2: Synthesis of Mercaptans 61-68

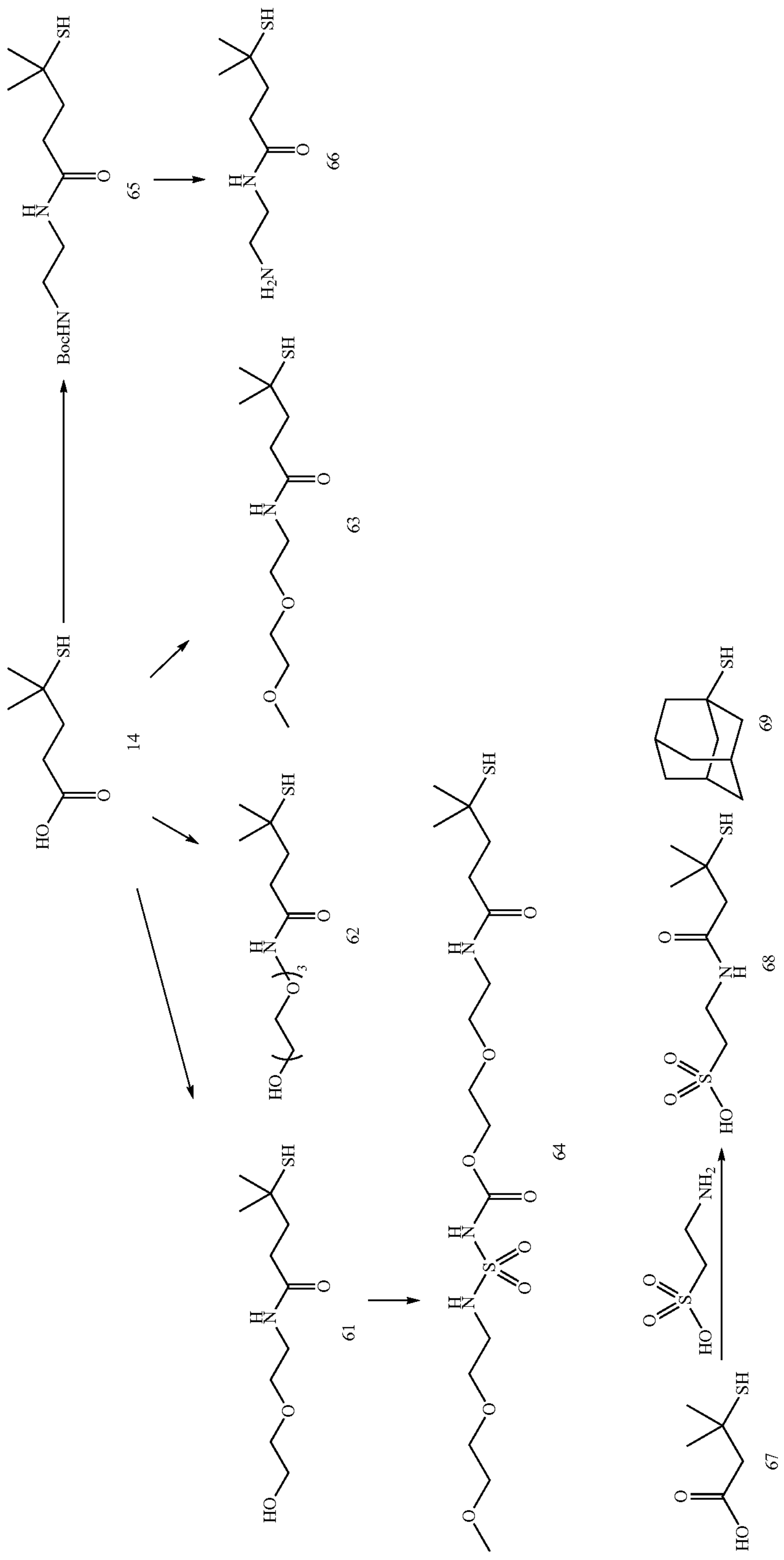
14
65
66
63
62
61
64
67
68
69

To a solution of 4-mercapto-4-methylpentanoic acid (539 mg, 3.64 mmol) in MeCN (3.2 mL) were added $Ac_2O$ (562 μL, 408 mg, 4.00 mmol), $Et_3N$ (1.0 mL, 737 mg, 7.28 mmol) and DMAP (4.0 mg, 0.033 mmol). The mixture was stirred for 30 min and a solution of 2-(2-aminoethoxy)ethanol (548 μL, 574 mg, 5.46 mmol) in MeCN (0.65 mL) was added. The mixture was stirred for 20 h and concentrated. The residue was purified by silica chromatography (DCM→10% MeOH in DCM). The desired product was obtained as a colorless oil (594 mg, 2.52 mmol, 69%). 1H NMR (400 MHz, $CDCl_3$) δ (ppm) 6.10 (bs, 1H), 3.79-3.73 (m, 2H), 3.62-3.54 (m, 4H), 3.51-3.44 (m, 2H), 2.41-2.34 (m, 2H), 1.95-1.89 (m, 2H), 1.64 (s, 1H), 1.38 (s, 6H).

To a solution of 4-mercapto-4-methylpentanoic acid (163 mg, 1.10 mmol) in MeCN (2.0 mL) were added sequentially acetic anhydride (114 μL, 1.21 mmol, 1.10 equiv.), $Et_3N$ (307 μL, 2.20 mmol, 2.00 equiv.) and DMAP (1.34 mg, 11.0 μmol). The mixture was stirred for 32 minutes, followed by the addition 2-(2-(2-(2-aminoethoxy)ethoxy)ethoxy)ethanol (319 mg, 1.65 mmol, 1.50 equiv.). The resulting reaction mixture was stirred for 18 hours at rt and then conc. in vacuo. The residue was purified by silica chromatography (1→10% MeOH in DCM). The desired product was obtained as a yellow oil (342 mg, 1.05 mmol, 96%). 1H NMR (400 MHz, $CDCl_3$) δ (ppm) 7.22 (bs, 1H), 3.79-3.71 (m, 4H), 3.71-3.59 (m, 8H), 3.57-3.51 (m, 2H), 3.50-3.41 (m, 2H), 2.43-2.34 (m, 2H), 1.98-1.89 (m, 2H), 1.65 (bs, 1H), 1.40 (s, 6H). LCMS ($ESI^+$) calculated for $C_{14}H_{30}NO_5S^+$ ($M+H^+$) 324.18, found 324.36.

To a solution of 4-mercapto-4-methylpentanoic acid (226 μL, 251 mg, 1.69 mmol) in $CHCl_3$ were added 2-(2-methoxyethoxy)ethanamine (249 μL, 242 mg, 2.03 mmol) and N-ethyl-N'-(3-dimethylaminopropyl)carbodiimide hydrochloride (0.35 g, 1.82 mmol). The mixture was stirred for 1.5h, heated to 60° C. for 2h and subsequently stirred at rt for 3d. The reaction mixture was then purified by silica chromatography (50% EtOAc in heptane→EtOAc). The desired product was obtained as a colorless oil (0.23 g, 0.29 mmol, 54%). 1H NMR (400 MHz, $CDCl_3$) δ (ppm) 6.20-6.00 (bs, 1H), 3.65-3.60 (m, 2H), 3.59-3.53 (m, 4fH), 3.49-3.44 (m, 2H), 3.40 (s, 3H), 2.40-2.33 (m, 2H), 1.96-1.88 (m, 2H), 1.63 (bs, 1H), 1.38 (d, J=0.5 Hz, 6H).

To a solution of 61 (165 mg, 0.70 mmol) in DCM (10 mL) were added CSI (61 μL, 99 mg, 0.70 mmol), $Et_3N$ (293 μL, 213 mg, 2.1 mmol) and 2-(2-methoxyethoxy)ethanamine (100 mg, 0.84 mmol). The mixture was stirred for 2 h and aqueous saturated $NH_4Cl$ (20 mL) was added, followed by DCM (10 mL). The layers were separated, and the organic phase was dried (Na2SO4) and concentrated. The residue was purified by silica chromatography (DCM→10% MeOH in DCM). The product was obtained as a colorless liquid (110 mg, 0.24 mmol, 34%). 1H NMR (400 MHz, $CDCl_3$) δ (ppm) 6.26-6.16 (m, 1H), 4.36-4.31 (m, 2H), 3.80-3.24 (m, 16H), 3.40 (s, 3H), 2.43-2.35 (m, 2H), 1.96-1.90 (m, 2H), 1.70 (s, 1H), 1.39 (s, 6H).

To a solution of 4-mercapto-4-methylpentanoic acid (99 mg, 0.62 mmol, 1.0 equiv.) in dry DCM (3.0 mL) was added N-ethyl-N'-(3-dimethylaminopropyl)carbodiimide hydrochloride (141 mg, 736 μmol, 1.18 equiv.), followed by DiPEA (226 μL, 1.37 mmol, 2.20 equiv.). The resulting solution was stirred at rt for 10 min, followed by the addition of N-Boc-ethylenediamine (132 mg, 821 μL, 1.32 equiv.). The reaction mixture was stirred for 1 day and then diluted with DCM (30 mL). The resulting solution was washed with sat. aq. $NH_4Cl$ (10 mL), sat. aq. $NaHCO_3$ (10 mL), brine (10 mL), dried with $Na_2SO_4$ and then conc. in vacuo. The residue was purified by silica gel chromatography (0→5% MeOH in DCM). The product was obtained a colorless oil (120 mg, 413 μmol, 67%), which was used without further purification in the next step. LCMS (ESI+) calculated for $C_{13}H_{26}N_2NaO_3S^+$ ($M+Na^+$) 313.16, found 313.11.

To a solution of 65 (101 mg, 348 μmol) in DCM (10.0 mL) was added TFA (240 μL). The reaction mixture was stirred at rt for 1 hour, followed by the addition of additional TFA (1.0 mL). The mixture was stirred for another hour and then conc. in vacuo. The residue was co-evaporated with toluene twice, affording 130 mg of a light yellow oil, which was used crude in the next step.

To a solution of 3-methyl-3-sulfanylbutanoic acid (56 mg, 0.41 mmol) in DMF (1.0 mL) were added HATU (158 mg, 0.41 mmol), DiPEA (214 μL, 159 μL, 1.23 mmol) and taurine (56 mg, 0.45 mmol). The mixture was placed on a tube roller. After 25 min, the mixture was sonicated. The mixture was then stirred, heated to 80° C. for 135 min and allowed to come to rt. The mixture was then stirred for 3d at room temperature and filtered. The filtrate was purified by RP-HPLC (C18, 5%→90% MeCN (1% AcOH) in $H_2O$ (1% AcOH)). The product (357 mg) could not be obtained in pure form but was used as-is in the next step. LCMS (ESI−) calculated for $C_7H_{14}NO_4S_2^-$ ($M-H^+$) 240.04 found 240.22.

Example 5-3: Trisulfide to Disulfide Exchange Reaction of Calicheamicin with Mercaptans 61, 63, 64, and 66

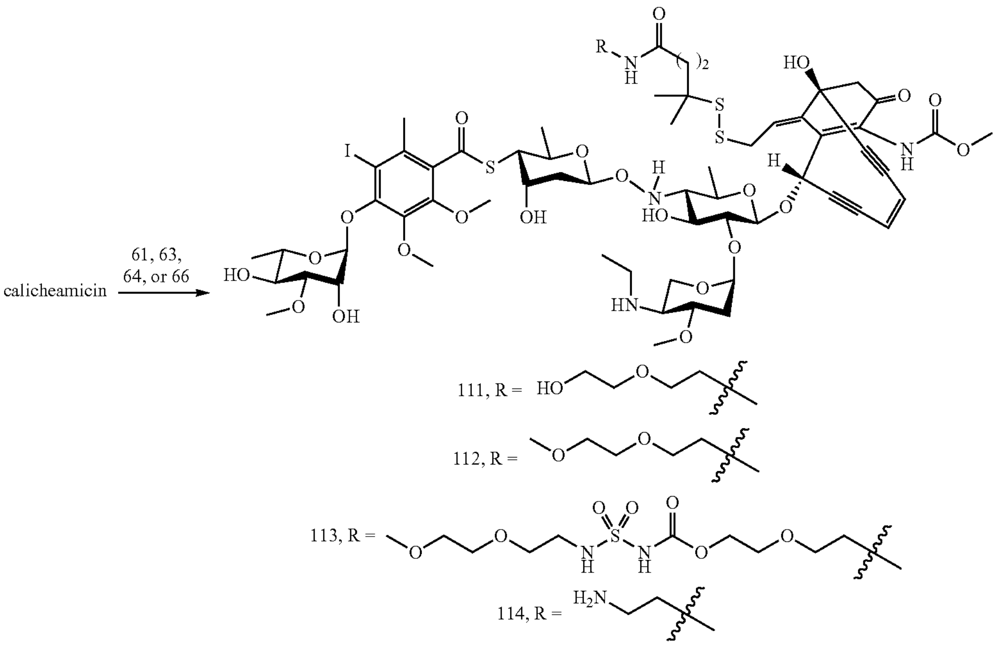

111, R =

112, R =

113, R =

114, R =

To a cooled (−15° C.) solution of calicheamicin γ1 (23.5 mg; 17.2 μmol) in a mixture of DMF (119 μL) and MeCN (25 mL) were added a solution of 61 (38 mg, 0.17 mmol) in DMF (0.38 mL) and $Et_3N$ (17.4 mg, 24 μL, 0.17 mmol). After 1 h, the mixture was slowly allowed to come to rt. After another 2 h, the mixture was concentrated and the residue was purified by silica chromatography (0%→15% MeOH in DCM). The desired product was obtained as a colorless film (18.0 mg, 11.8 μmol, 69%). LCMS ($ESI^+$) calculated for $C_{64}H_{92}IN_4O_{24}S_3^+$ ($M+H^+$) 1523.43, found 1523.65.

To a cooled (−15° C.) solution of calicheamicin γ1 (42 mg; 30.7 μmol) in a mixture of DMF (300 μL) and MeCN (8 mL) were added a solution of 63 (74 mg, 0.34 mmol) in MeCN (300 μL) and $Et_3N$ (47 μL, 34 mg, 0.34 mmoL). The mixture was stirred and slowly allowed to come to rt. After 1h, the mixture was concentrated and purified by silica chromatography (DCM→15% MeOH in DCM). The desired product was obtained as a white film (38.7 mg; 25 μmol). LCMS ($ESI^+$) calculated for $C_{65}H_{94}IN_4O_{24}S_3$+($M+H^+$) 1537.45. found 1537.79.

To a cooled (−25° C.) solution of calicheamicin γ1 (5.0 mg; 3.7 μmol) in DMF (100 μL) and MeCN (1 mL) were added a solution of 64 (17 mg, 0.037 mmol) in MeCN (200 μL) and $Et_3N$ (5.2 μL, 3.7 mg, 0.37 mmoL). The mixture was stirred and slowly allowed to come to rt. After 2.5 h, the mixture was concentrated till 700 μL diluted with MeCN (100 μL) and purified via RP HPLC (C18, 5%→90% MeCN (1% AcOH) in water (1% AcOH). The desired product was obtained as a colorless film (5.7 mg; 3.3 μmol). LCMS ($ESI^+$) calculated for $C_{70}H_{104}IN_6O_{29}S_4$+($M+H^+$) 1747.48 found 1748.90.

To a cooled (−15° C.) solution of calicheamicin γ1 (5.0 mg; 3.7 μmol) in DMF (100 μL) were added a solution of 66 (7.0 mg, 37 μmol) in MeCN (0.32 mL) and $Et_3N$ (5.1 μL, 3.7 mg, 37 μmol). The mixture was slowly allowed to come to rt. After 75 min, the mixture was purified by RP-HPLC (5%→90% MeCN (1% AcOH) in H2O (1% AcOH). The product was obtained as colorless film (2.6 mg, 1.8 μmol, 49%). LCMS ($ESI^+$) calculated for $C_{62}H_{89}IN_5O_{22}S_3^+$ ($M+H^+$) 1478.42, found 1478.58.

Example 5-4: Direct Acylation of Disulfide-Exchanged Calicheamicin 111 with 42 to Give BCN-Calicheamicin 121 with Non-Cleavable Linker

111 + 42

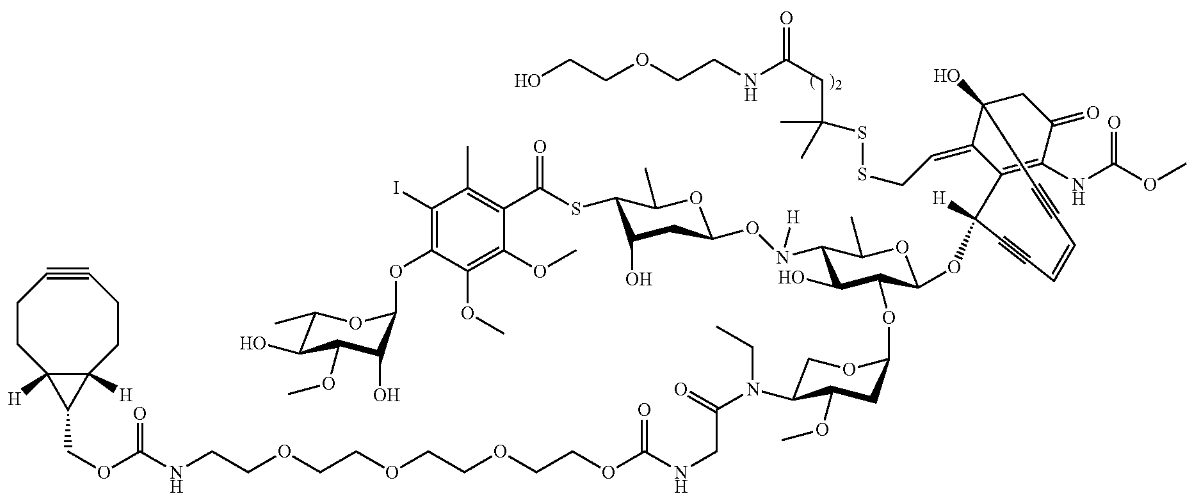

121

To a solution of 42 (7.7 mg, 16.4 μmol) in DMF (40 μL) were added a solution of bis(pentafluorophenyl) carbonate (5.8 mg, 14.8 μmol) in DMF (18 μL) and N-methylmorpholine (5.4 μL, 5.0 mg, 49.2 μmol). The mixture was left standing for 2h and a solution of 111 (5.0 mg, 3.3 μmol) in DMF (59 μL). The reaction mixture was heated to 37° C. and shaken for 21.5 h. Molsieves (spherical, 11 mg, 4 Å) were added. Next, to a vial with molsieves (spherical, 16 mg, 4 Å) were added a solution of 42 (7.6 mg, 16.1 μmol) in DMF (40 μL), a solution of bis(pentafluorophenyl) carbonate (5.9 mg, 15.0 μmol) in DMF (18 μL) and NMM (5.4 μL, 5.0 mg, 49.2 μmol). The mixture was left standing for 1h and then without molsieves transferred to the reaction mixture. The mixture was then left standing for 2d, diluted with DCM (0.8 mL) and purified by silica gel chromatograph (without molsieves) (0%→20% MeOH in DCM). The fractions containing the product were concentrated and purified by RP-HPLC (C18, MeCN (1% AcOH) in H2O (1% AcOH), which yielded 2.4 mg (1.2 μmol, 36%) of the desired product. LCMS (ESI+) calculated for $C_{86}H_{124}IN_6O_{32}S_3^+$ (M+$H^+$) 1975.65, found 1977.24.

Example 5-5: Step-Wise Acylation of Disulfide-Exchanged Calicheamicins 111 and 112 to Give BCN-Calicheamicins 124 and 127 with Cleavable Linker

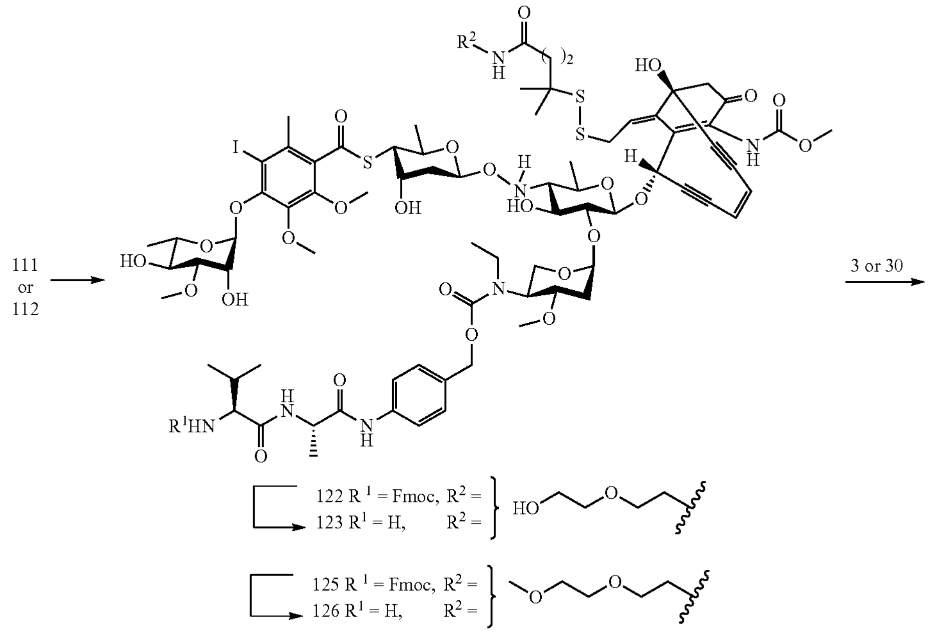

-continued

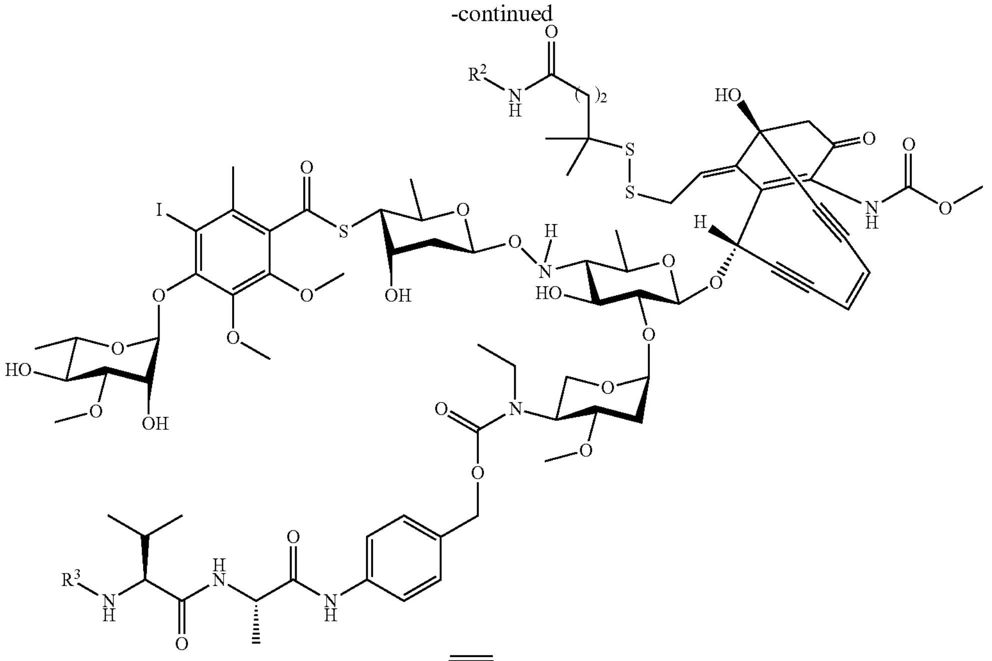

124 $R^2$ = 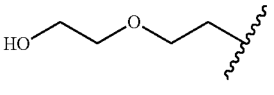 $R^3$ = 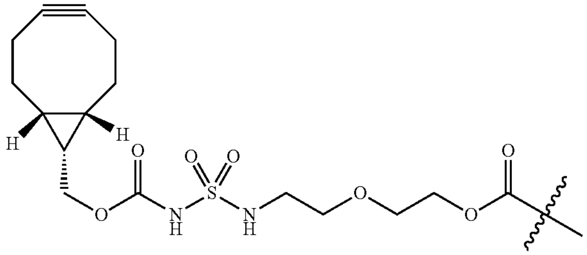

127 $R^2$ = 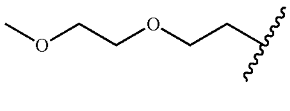 $R^3$ = 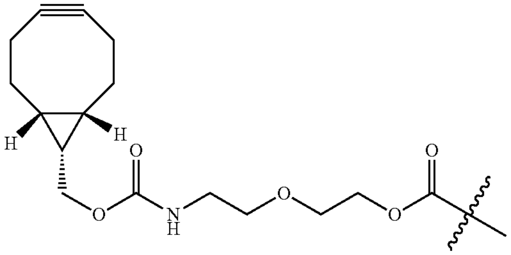

To a vial containing Fmoc-Val-Ala-PAB-OSu (11, 37.1 mg, 56.5 μmol) was added a solution of 111 (17.2 mg, 11.3 μmol) in DMF (0.28 mL). DMF was added (100 μL) and the resulting mixture was heated to 37° C. and shaken for 19h. The mixture was diluted with DMF (100 μL) and concentrated. The residue was purified by silica gel chromatography (0%→15% MeOH in DCM). The desired product was obtained as a colorless film (9.9 mg, 4.8 μmol, 42%). LCMS ($ESI^+$) calculated for $C_{95}H_{124}IN_7O_{30}S_{32}^+$ $(M+2H^+)/2$ 1033.33, found 1033.60.

To a solution of 122 (9.9 mg, 4.8 μmol) in a mixture of THE and $H_2O$ (25:1, 2 mL) was added diethylamine (0.5 mL). The mixture was left standing for 2h and was concentrated. The residue was dissolved in DMF (0.54 mL) and purified by RP-HPLC (C18, 5%→90% MeCN (1% AcOH) in $H_2O$ (1% AcOH). The desired product was obtained as a colorless film (3.6 mg, 2.0 μmol, 42%). LCMS (ESI+) calculated for $C_{80}H_{113}IN_7O_{28}S_3^+$ $(M+H^+)$ 1842.58, found 1843.83.

To a solution of 123 (3.6 mg, 2.0 μmol) in DMF (33 μL) were added a solution of 3 (5.3 mg, 10 μmol) in DMF (19 μL) and $Et_3N$ (0.84 μL, 0.61 mg, 6.0 μmol). After 3h, the reaction mixture was purified by silica chromatography (0%→20% MeOH in DCM), which afforded 2.4 mg (1.1 μmol, 55%) of the desired product. LCMS ($ESI^+$) calculated for $C_{96}H_{136}IN_9O_{35}S_4^{2+}$ $(M+2H^+)/2$ 1115.35, found 1115.40.

To a vial containing 52 (6.6 mg, 9.1 μmol, 6.3 equiv.) was added a solution of 112 (2.19 mg, 1.43 μmol, 1.00 equiv.) in DMF (72 μL). The resulting solution was conc. in vacuo to a volume of circa 18 μL. The mixture was left for 42h at rt and then diluted in THE (205 μL) and $H_2O$ (10 μL). To the resulting solution, containing crude 125, was added diethylamine (55 μL). The reaction mixture was left at rt for 1 hour and then conc. in vacuo. The residue was purified by RP-HPLC (C18, 30→90% MeCN (1% AcOH) in water (1% AcOH). The desired product was obtained as a colorless oil (3.0 mg, quant.). LCMS ($ESI^+$) calculated for $C_{81}H_{115}IN_7O_{28}S_3^+$ $(M+H^+)$ 1856.60, found 1856.67.

To a solution of 125 (3.0 mg, 1.6 μmol, 1.0 equiv.) in DMF (100 μL) was added a solution of 30 (3.95 mg, 8.84 μmol, 5.5 equiv.) in DMF (14.3 μL), followed by a 50% v/v solution of $Et_3N$ in DMF (3.15 μL). The resulting mixture was mixed thoroughly and left at rt for 4.5 hours and was then purified by silica chromatography (0→20% MeOH in DCM). The desired product was obtained as a white residue (2.4 mg, 1.1 μmol, 68% yield). LCMS ($ESI^+$) calculated for $C_{97}H_{137}IN_8O_{33}S_3^{2+}$ $(M+2H^+)/2$ 1082.88, found 1083.12.

Example 5-6: Step-Wise Acylation of Disulfide-Exchanged Calicheamicin 113 to Give BCN-Calicheamicin 130 with Cleavable Linker

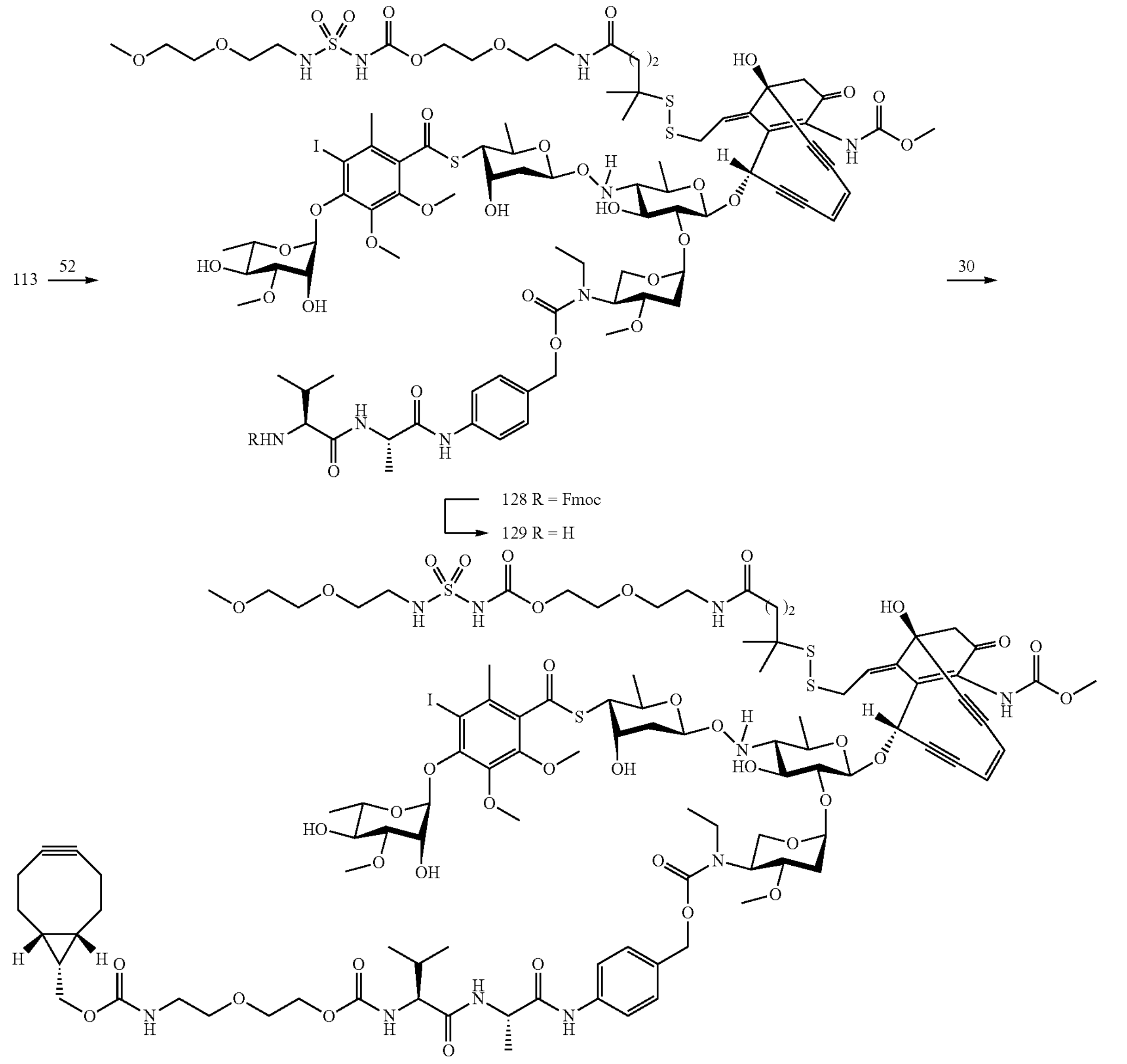

130

To a vial containing 52 (5.9 mg, 8.1 μmol) was added a solution of 113 (2.7 mg, 1.5 μmol) in DMF (300 μL). The reaction mixture was diluted with DMF (50 μL), heated to 37° C. and shaken for 19h. The r.m. was concentrated till 0.1 mL, heated to 37° C. and shaken for 2d. Extra 52 (11.8 mg, 16 μmol) was added and the r.m. was agitated for 1d at 37° C. The mixture was diluted with DCM (0.8 mL) and purified by silica chromatography (0%→20% MeOH in DCM). The desired product was obtained as a white film (2.3 mg, 1.0

μmol, 67%). LCMS ($ESI^+$) calculated for $C_{101}H_{136}IN_9O_{35}S_4^{2+}$ $(M+2H^+)/2$ 1145.35, found 1145.44.

To a solution of 128 (2.3 mg, 1.0 μmol) in DMF (200 μL) was added diethylamine (10 μL). After 80 min, the mixture was purified by RP-HPLC (5%→90% MeCN (1% AcOH) in $H_2O$ (1% AcOH), which afforded 0.5 mg (0.24 μmol, 24%) of the desired product. LCMS ($ESI^+$) calculated for $C_{86}H_{126}IN_9O_{33}S_4^{2+}$ $(M+2H^+)/2$ 1033.82, found 1034.43.

To a solution of 129 (0.5 mg, 0.24 μmol) in DMF (240 μL) were added a solution of 30 (0.21 mg, 0.48 μmol) in DMF (4.0 μL) and $Et_3N$ (1.7 μL of 10% solution in DMF). The mixture was left standing for 65h and 2,2'-(ethylenedioxy)bis(ethylamine) (2.8 μL of 10% solution in DMF, 0.28 μg, 1.9 μmol) was added. After 2h, the mixture was purified by RP-HPLC (30%→90% MeCN (1% AcOH) in $H_2O$ (1% AcOH). The product was obtained a colorless film (0.4 mg, 0.17 μmol, 71%). LCMS (ESI+) calculated for $C_{102}H_{147}IN_{10}O_{38}S_4^{2+}$ $(M+2H^+)/2$ 1187.89, found 1187.93.

Example 5-7: Synthesis of Fmoc-6-Aminohexanoic Anhydride 51 and BCN-Calicheamicin Derivative 134 with Cleavable Linker

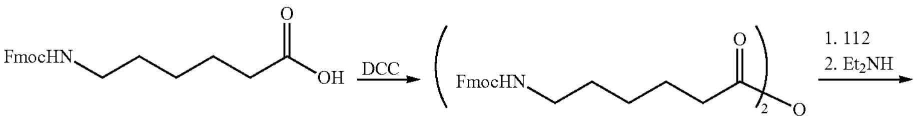

51

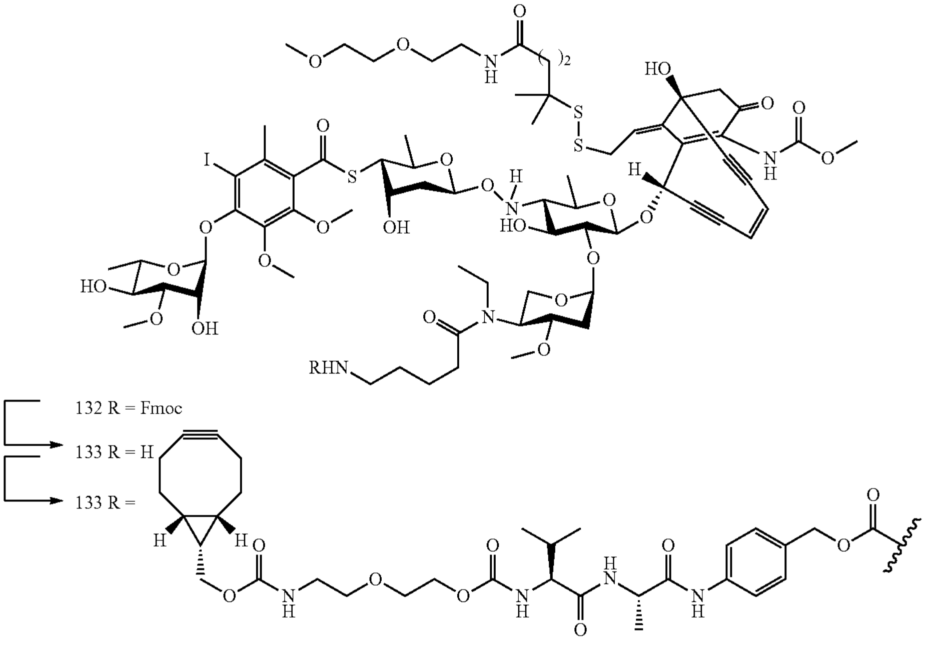

To a mixture of Fmoc-6-aminohexanoic acid (120 mg, 0.34 mmol) in DCM (10 mL) and DMF (0.5 mL) was added DCC (35 mg, 0.17 mmol). The mixture was stirred for 15 min and partially concentrated until all DCM was removed. The residue was diluted with DMF (1.0 mL), filtered and used crude in the next step (51). To a solution of 112 (5.0 mg, 3.3 μmol) in DMF (163 μL) was added a crude solution of 51 (22 mg, 32 μmol) in DMF (287 μL). The mixture was left standing for 18h and purified by RP-HPLC (C18, 30%→90% MeCN (1% AcOH) in $H_2O$ (1% AcOH). The desired product was obtained as a white solid (4.4 mg, 2.3 μmol, 72%). LCMS (ESI+) calculated for $C_{86}H_{115}IN_5O_{27}S_3^+$ (M+H$^+$) 1872.60, found 1873.77.

To a solution of 132 (4.4 mg, 2.3 μmol) in DMF (470 μL) was added diethylamine (10 μl). The mixture was left standing for 65 min and purified by RP-HPLC (C18, 5%→90% MeCN (1% AcOH) in $H_2O$ (1% AcOH), which yielded 4.2 mg (2.5 μmol, quant.) of the desired product. LCMS (ESI$^+$) calculated for $C_{71}H_1O_5IN_5O_{25}S_3^+$ (M+H$^+$) 1650.53, found 1650.75.

To a solution of 133 (4.2 mg, 2.5 μmol) in DMF (250 μL) were added a solution of 32 (2.3 mg, 3.0 μmol) in DMF (150 μL) and $Et_3N$ (1.7 μL, 1.3 mg, 13 μmol). The mixture was left standing for 65 h and 2,2'-(ethylenedioxy)bis(ethylamine) (1.5 μL, 1.5 mg, 10 μmol) was added. After 30 min, the mixture was purified by RP-HPLC (C18, 30%→90% MeCN (1% AcOH) in $H_2O$ (1% AcOH). The desired product was obtained as a white solid (3.4 mg, 1.5 μmol, 60%). LCMS (ESI$^+$) calculated for $C_{103}H_{148}IN_9O_{34}S_3^{2+}$ (M+H$^+$) 1139.42, found 1139.52.

Example 5-8: Synthesis of Glutaric Acid Calicheamicin 135 and BCN-Calicheamicin Derivative 136 with Cleavable Linker

112

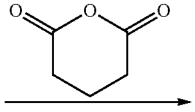

-continued

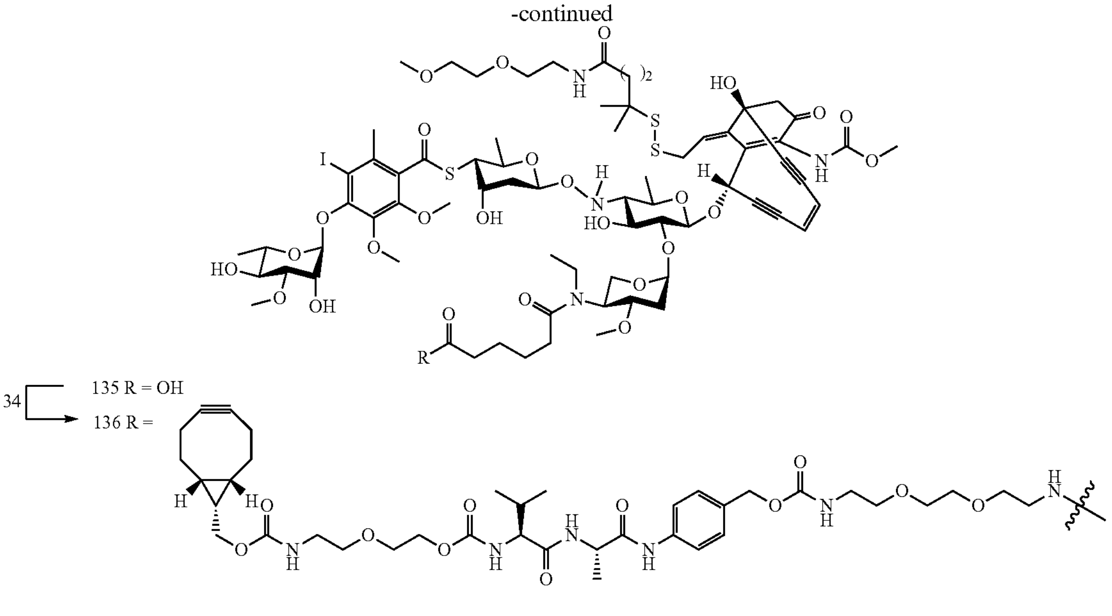

To a solution of 112 (5.0 mg, 3.3 μmol) in DMF (163 μL) was added a solution of glutaric anhydride (3.7 mg, 32 μmol) in DMF (20 μL). The reaction mixture was left standing for 20h and then heated to 37° C. The mixture was left standing for 22h and then allowed to come to rt. The mixture was left standing for 25h and diluted with DMF (100 μL). After 3h, the mixture was purified by RP-HPLC (C18, 5%→90% MeCN in $H_2O$). The desired product was obtained as a white film (4.6 mg, 2.8 μmol, 86%). LCMS ($ESI^+$) calculated for $C_{70}H_{100}IN_4O_{27}S_3^+$ ($M+H^+$) 1651.48, found 1651.71.

To a solution of 135 (4.6 mg, 2.8 μmol) in DMF (280 μL) was added a solution of 34 (2.2 mg, 2.8 μmol) in DMF (280 μL), a solution of NHS (0.39 mg, 3.4 μmol) in DMF (5.7 μL) and a solution of EDCl (0.64 mg, 3.4 μmol) in DMF (85 μL). The resulting mixture was left standing for 18 h and purified by RP-HPLC (018, 30%→90% MeCN (1% AcOH) in $H_2O$ (1% AcOH)). The desired product was obtained as a colorless film (0.8 mg, 0.33 μmol). LCMS ($ESI^+$) calculated for $C_{108}H_{157}IN_{10}O_{37}S_3^2$. ($M+2H^+$)/2 1204.95, found 1205.24.

Example 5-9: Synthesis of BCN-Calicheamicin Derivatives 139 and 140 with Cleavable Linker

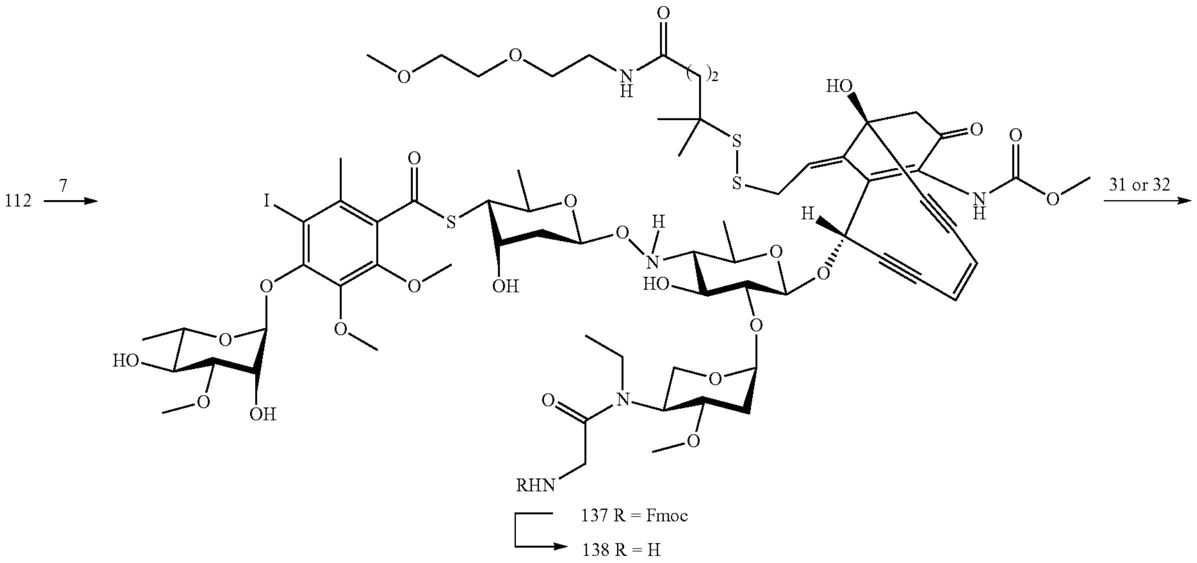

-continued

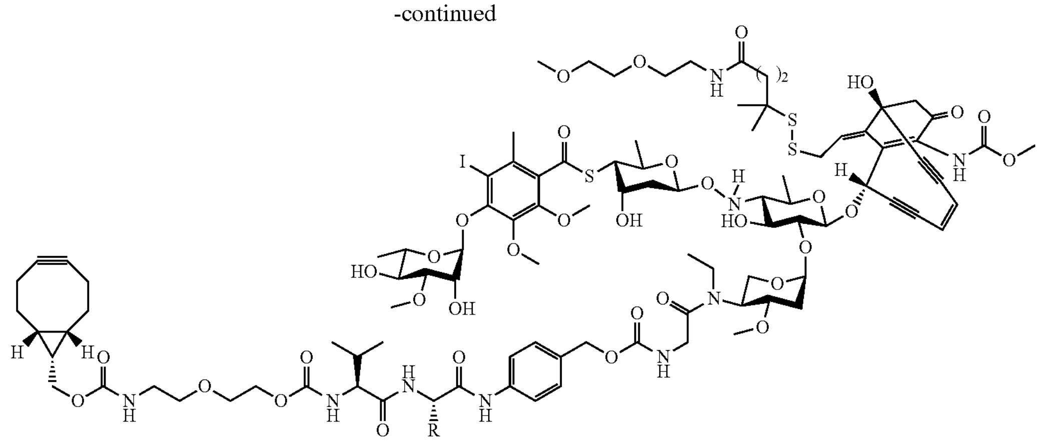

139 R = $CH_3$

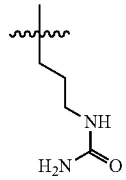

140 R =

To a suspension of Fmoc-Gly-OH (0.10 g, 0.34 mmol) in DCM (10 mL) were added DMF (500 μL) and N,N-dicyclohexylcarbodiimide (35 mg, 0.17 mmol. The resulting mixture was stirred for 15 min. and concentrated until DCM was evaporated. The suspension was diluted with DMF (1000 μL), filtered and used crude in the next step. 172 μL of this mixture, containing 7, was added to a solution of 112 (3.0 mg, 2.0 μmol) in DMF (97 μL). The resulting mixture was left standing for 19h and purified by RP HPLC (C18, 30%→90% MeCN (1% AcOH) in $H_2O$ (1% AcOH), which yielded 2.5 mg (1.38 μmol, 71%) of the desired product as a white solid. LCMS (ESI$^+$) calculated for $C_{82}H_{107}IN_5O_{27}S_3^+$ (M+H$^+$) 1816.54, found 1816.77.

To a solution of 137 (10.2 mg, 5.6 μmol) in DMF (560 μL) was added piperidine (20 μL). The mixture was left standing for 1.5h and was purified by RP HPLC (C18, 5%→90% MeCN (1% AcOH) in $H_2O$ (1% AcOH). The desired product was obtained as a slightly brown film (9.3 mg, 5.8 μmol, quant.). LCMS (ESI$^+$) calculated for $C_{67}H_{97}IN_5O_{25}S_3^+$ (M+H$^+$) 1594.47 found 1594.87.

To a solution of 138 (1.8 mg, 1.1 μmol) in DMF (210 μL) were added 31 (0.94 mg, 1.1 μmol) as a solution in DMF (55 μL) and $Et_3N$ (1.5 μL, 1.1 mg, 11 μmol). The mixture was left standing for 19 h and was purified by RP HPLC (C18, 30%→90% MeCN (1% AcOH) in $H_2O$ (1% AcOH). The desired product was obtained as a white solid (1.5 mg, 0.65 μmol, 59%). LCMS (ESI$^+$) calculated for $C_{102}H_{146}IN_{11}O_{35}S_3^2$. (M+2H$^+$)/2 1154.41 found 1154.78.

To a solution of 138 (2.9 mg, 1.8 μmol) in DMF (180 μL) were added 32 (2.1 mg, 2.7 μmol) as a solution in DMF (41 μL) and $Et_3N$ (2.5 μL, 1.8 mg, 18 μmol). The mixture was left standing for 19h and was purified by RP HPLC (C18, 30%→90% MeCN (1% AcOH) in $H_2O$ (1% AcOH). The desired product was obtained as a white solid (2.5 mg, 1.1 μmol, 63%). LCMS (ESI$^+$) calculated for $C_{99}H_{140}IN_9O_{34}S_3^{2+}$ (M+2H$^+$)/2 1111.39 found 1111.70.

Example 5-10: Synthesis of BCN-Calicheamicin Derivatives 142, 144 and 146 with Cleavable Linker

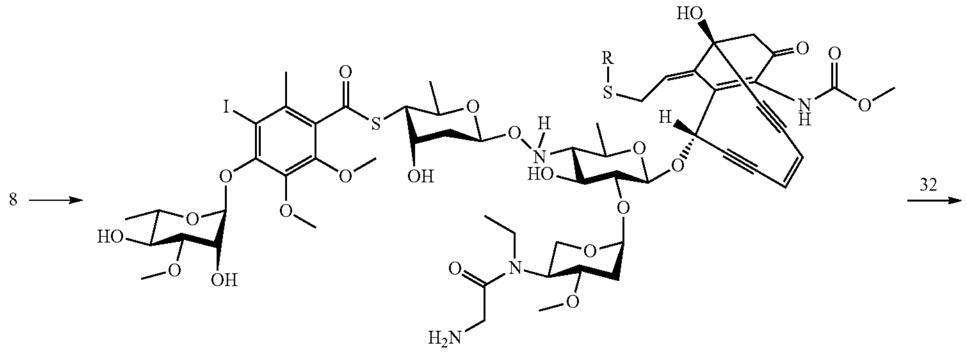

141, R = 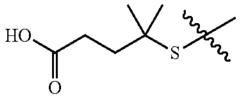

143, R = 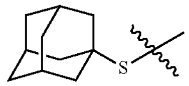

145, R = 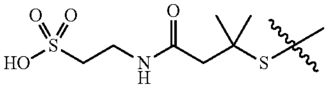

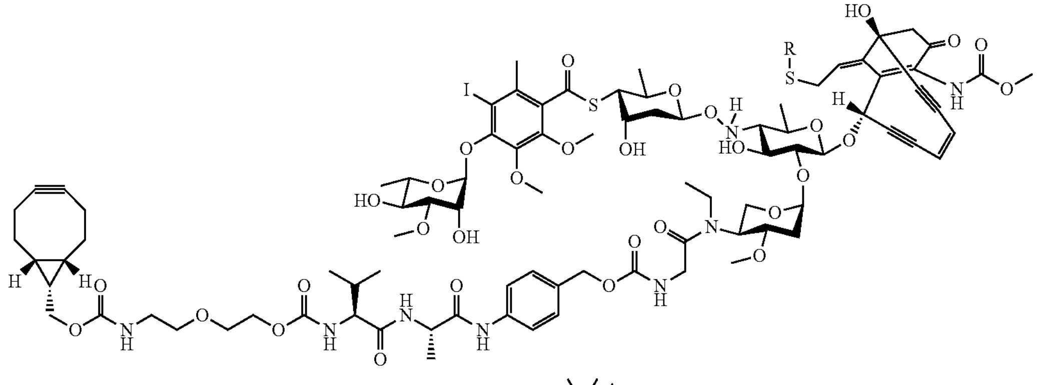

142, R = 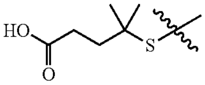

144, R = 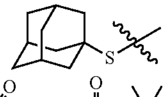

146, R = 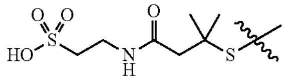

A solution of 8 (4.50 mg, 3.16 μmol, 1.00 equiv.) in DMF (69.2 μL) was diluted with MeCN (1.0 mL) and the resulting light yellow solution was cooled to −15° C. and a solution of 4-mercapto-4-methylpentanoic acid (4.68 mg, 31.6 μmol, 10.0 equiv.) in MeCN (47 μL), followed by $Et_3N$ (4.40 μL, 31.6 μmol, 10.0 equiv.). The resulting light yellow suspension was left in −15° C. for 30 minutes and was then allowed to warm to rt. After circa 1 hour at rt the reaction mixture was stored in the freezer for 2 days and then conc. in vacuo and purified by silica chromatography (0→100% MeOH in DCM). The desired product was obtained as a white residue (2.9 mg, 1.9 μmol, 61% yield). LCMS (ESI+) calculated for $C_{62}H_{86}IN_4O_{24}S_3^+$ (M+H$^+$) 1493.38, found 1493.53.

To a solution of 141 (2.9 mg, 1.9 μmol, 1.0 equiv.) in DMF (140 μL) was added 32 (3.0 mg, 3.9 μmol, 2.0 equiv.) in DMF (60 μL), followed by $Et_3N$ (0.81 μL, 5.8 μmol, 3.0 equiv.), generating a yellow solution. The reaction mixture was left at rt for 4h and then purified by silica chromatography (0→33% MeOH in DCM). The desired product was obtained as a white residue (2.4 mg, 1.1 μmol, 58% yield). LCMS (ESI$^+$) calculated for $C_{94}H_{129}IN_8O_{33}S_3^{2}$. (M+2H$^+$)/2 1060.84, found 1061.14. A solution of 8 (4.50 mg, 3.16 μmol, 1.00 equiv.) in DMF (69.2 μL) was diluted with MeCN (1.0 mL) and the resulting light yellow solution was cooled to −15° C. and a solution of 1-adamantanethiol (5.30 mg, 31.6 μmol, 10.0 equiv.) in MeCN (53.1 μL), followed by $Et_3N$ (4.40 μL, 31.6 μmol, 10.0 equiv.). The resulting light yellow suspension was left in −15° C. for 47 minutes and was then allowed to warm to rt. After circa 50 minutes at rt the reaction mixture was conc. in vacuo and purified by silica chromatography (0→25% MeOH in DCM). The desired product was obtained as an off-white residue (3.3 mg, 2.2 μmol, 70% yield). LCMS (ESI$^+$) calculated for $C_{66}H_{9}0IN_4O_{22}S_3^+$ (M+H$^+$) 1513.42, found 1513.45.

To a solution of 143 (3.3 mg, 2.2 μmol, 1.0 equiv.) in DMF (42 μL) was added 32 (3.3 mg, 4.3 μmol, 2.0 equiv.) in DMF (42 μL), followed by $Et_3N$ (0.91 μL, 6.5 μmol, 3.0 equiv.) generating a yellow solution. The reaction mixture was left at rt for 2 hours and then stored in the freezer. The mixture was removed from the freezer after 21 h and then purified by silica chromatography (0→20% MeOH in DCM), which afforded 2.3 mg (1.1 μmol, 50% yield) of the desired product. LCMS (ESI+) calculated for $C_{98}H_{133}IN_8O_{31}S_3^{2+}$ (M+2H$^+$)/2 1070.87, found 1070.99.

To a cooled (−20° C.) solution of 8 (4.25 mg, 3.0 μmol) in a mixture of MeCN (0.3 mL) and DMF (65 μL) were added a solution of 68 (14.4 mg, 60 μmol) in MeCN (35 μL) and $Et_3N$ (8.4 μL, 6.1 mg, 60 μmol). The mixture was slowly allowed to come to rt during 2h and purified by RP-HPLC (5%→90% MeCN (1% AcOH) in $H_2O$ (1% AcOH). The desired product was obtained as a colorless film (1.4 mg, 0.88 μmol, 29%). LCMS (ESI$^+$) calculated for $C_{63}H_{89}IN_5O_{26}S_4$+(M+H$^+$) 1586.37, found 1586.50.

To a solution of 145 (1.4 mg, 0.88 μmol) in DMF (177 μL) were added a solution of 32 (0.65 mg, 0.85 μmol) in DMF (63 μL) and $Et_3N$ (1.2 μL, 0.89 mg, 8.8 μmol). After 17h, the mixture was diluted with DCM (0.6 mL) and purified via silica chromatography (DCM→20% MeOH in DCM). The product was obtained as a white film (1.8 mg, 0.81 μmol, 95%). LCMS (ESI$^+$) calculated for $C_{95}H_{132}IN_9O_{35}S_4^{2+}$ (M+2H$^+$)/2 1107.34, found 1107.40.

Example 5-11: Synthesis of BCN-Calicheamicin Derivative 149 with Cleavable Linker

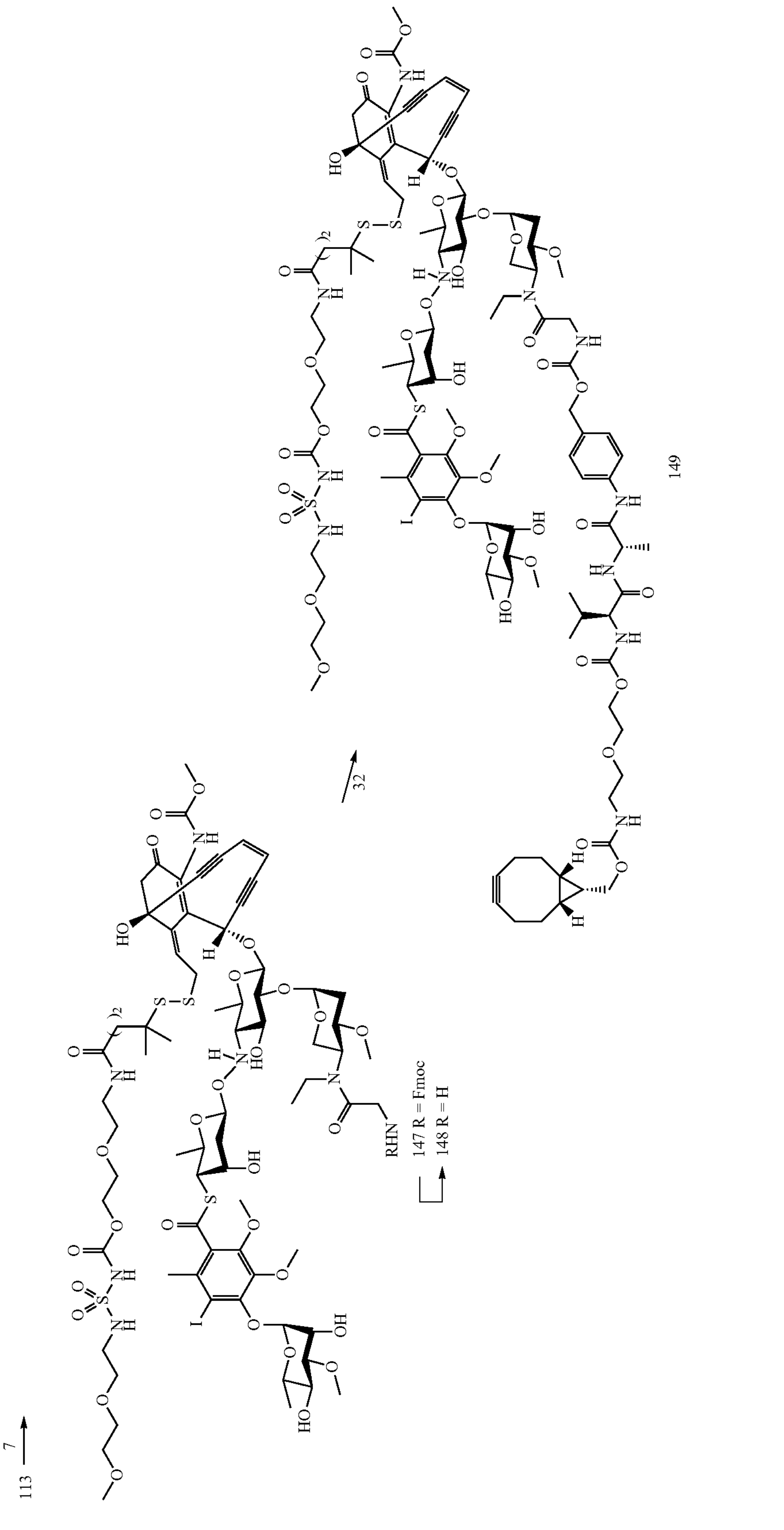
113
147 R = Fmoc
148 R = H
149

To a suspension of Fmoc-Gly-OH (0.10 g, 0.34 mmol) in CM (10 ml) were added DMF (500 μL) and N,N-dicyclohexylcarbodiimide (35 mg, 0.17 mmol. The resulting mixture was stirred for 15 min. and concentrated until CM was evaporated. The suspension was diluted with DMF (1.0 mL), filtered and used crude in the next step (7). To a solution of 113 (5.7 mg, 3.3 μmol) in DMF (330 μL) was added a crude solution of 7 (292 μL). The mixture was left standing for 5d, diluted with DMF (100 μL) and purified via HPLC (C18, 30%→90% MeCN (1% AcOH) in $H_2O$ (1% AcOH). The desired product was obtained as a white solid (0.9 mg, 0.44 μmol, 13%). LCMS (ESI+) calculated for $C_{87}H_{118}IN_7O_{32}S_4^{2+}$ (M+2H$^+$)/2 1013.79 found 1014.59.

To a solution of 147 (0.9 mg, 0.44 mmol) in DMF (176 μL) was added diethylamine (10 μL). The mixture was left standing for 30 min and purified by RP HPLC (C18, 5%→90% MeCN (1% AcOH) in $H_2O$ (1% AcOH), which yielded >0.9 mg (0.44 μmol, quant.) of the desired product. LMS (ESI$^+$) calculated for $C_{72}H_{107}IN_7O_{30}S_4^{2+}$ (M+H$^+$) 1804.50 found 1805.82.

To a solution of 148 (>0.9 mg, 0.44 μmol) in DMF (266 μL) were added a solution of 32 (1.0 mg, 1.34 μmol) in DMF (20 μL) and $Et_3N$ (0.93 μL, 0.68 mg, 6.7 μmol). The mixture was left standing for 44h and purified by RP-HPLC (C18, 30%→90% MeCN (1% AcOH) in $H_2O$ (1% AcOH), which yielded 0.5 mg (0.21 μmol, 48%) of the desired product. LCMS (ESI+) calculated for $C_{104}H_{150}IN_{11}O_{39}S_4^{2}$. (M+2H$^+$)/2 1216.40 found 1216.79.

Example 5-12: Synthesis of BCN-Calicheamicin Derivative 150 with Cleavable Linker

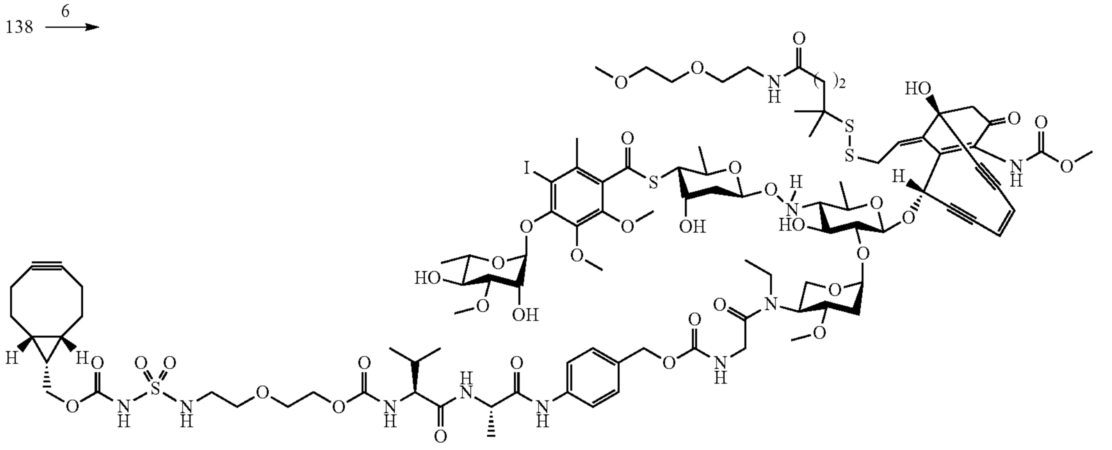

150

To a solution of 138 (210 μL of a 5 mM solution in DMF) were added a solution of 6 (1.4 mg, 1.7 μmol) in DMF (109 μL) and $Et_3N$ (0.8 μL). The resulting mixture was left standing for 2.5h and purified by RP-HPLC (C18, 30%→90% MeCN (1% AcOH) in $H_2O$ (1% AcOH), which yielded 1.0 mg (0.43 μmol, 39%) of the desired product. LCMS (ESI+) calculated for $C_{99}H_{141}IN_{10}O_{36}S_4^{2+}$ (M+2H$^+$)/2 1150.87 found 1151.83.

Example 5-13: Synthesis of BCN-Calicheamicin Derivative 154 with Cleavable Linker

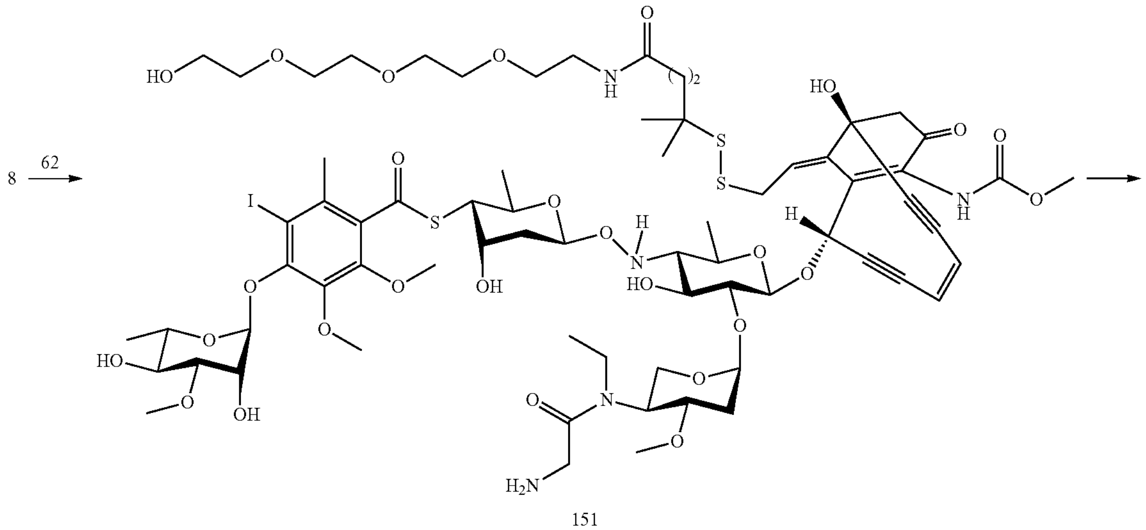

151

-continued

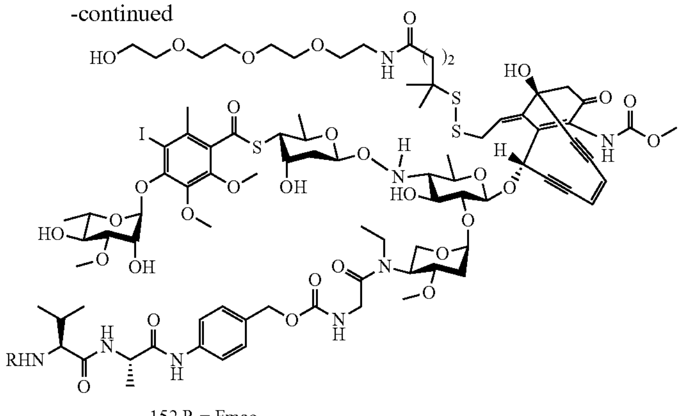

152 R = Fmoc

153 R = H

154 R =

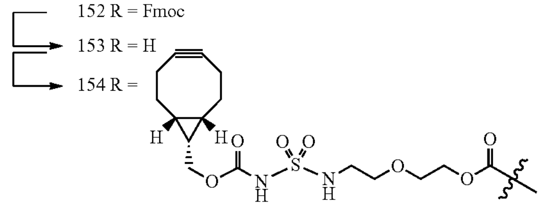

A solution of 8 (12.7 mg, 8.89 µmol, 1.00 equiv.) in DMF (195 µL) was diluted with MeCN (3.0 mL) and the resulting light orange solution was cooled to −15° C. by using a brine/ice-bath. Next, a solution of 62 (30.0 mg, 88.9 µL, 10.0 equiv.) in MeCN (300 µL) was added, followed by $Et_3N$ (12.4 µL, 88.9 µmol, 10.0 equiv.). The resulting light yellow suspension was left in the ice-bath for 80 minutes and was then allowed to warm to rt. The reaction mixture was left at rt for a few minutes and then conc. in vacuo, followed by purification by silica chromatography (0→33% MeOH in DCM). The desired product was obtained as a white residue (9.1 mg, 5.4 µmol, 61% yield). LCMS (ESI+) calculated for $C_{70}H_{103}IN_5O_{27}S_3^+$ (M+H$^+$) 1668.50, found 1668.59.

To a solution of 151 (9.1 mg, 5.4 µmol, 1.0 equiv.) in DMF (100 µL) was added a solution of 9-fluorenylmethyloxycarbonyl-valyl-alanyl-(4-aminobenzyl)-(4-nitrophenyl) carbonate (4.42 mg, 6.49 µmol, 1.20 equiv.) in DMF (48.6 µL). The resulting reaction mixture turned yellow and was left at rt for circa 30 minutes and then put in the freezer for 16h. The sample was then allowed to warm to rt and left for another 100 minutes and then additional 9-fluorenylmethyloxycarbonyl-valyl-alanyl-(4-aminobenzyl)-(4-nitrophenyl)carbonate (2.95 mg, 4.32 µmol, 0.8 equiv.) in DMF (32.4 µL) was added, followed by $Et_3N$ (1.89 µL, 13.5 µmol, 2.0 equiv.). The mixture was stirred at rt for 45 minutes and then diluted with THE (900 µL) and treated with diethylamine (100 µL). The resulting yellow solution was left at rt for 72 minutes and was then conc. in vacuo. The residue was purified by RP-HPLC (C18, 5%-95% MeCN (1% AcOH) in $H_2O$ (1% AcOH). The desired product was obtained as a brown oil (8.5 mg, 4.3 µmol, 79%). LCMS (ESI$^+$) calculated for $C_{86}H_{124}IN_8O_{31}S_3^+$ (M+H$^+$) 1987.66, found 1987.76.

To a vial containing 153 (0.60 mg, 0.30 µmol, 1.0 equiv.) in DMF (10.7 µL) was added a solution of 3 (0.79 mg, 1.50 µmol, 5.0 equiv.), followed by $Et_3N$ (0.25 µL, 6.0 equiv.). The resulting yellow solution was left at rt for 8 minutes and was then diluted with DMF (125 µL). The mixture was left at rt for 18 hours and was then concentrated in vacuo and dissolved in DMF (50 µL), followed by the addition of $Et_3N$ (0.25 µL). The resulting mixture was left at rt for 110 minutes and was then purified by silica chromatography (0→25% MeOH in DCM). The desired product was obtained as a white residue (3.1 mg, quant.). LCMS (ESI+) calculated for $C_{102}H_{147}IN_{10}O_{38}S_4^{2+}$ (M+2H$^+$)/2 1187.89, found 1188.00.

Example 5-14: Synthesis of BCN-Calicheamicin Derivative 155 with Non-Cleavable Linker

138 + 41

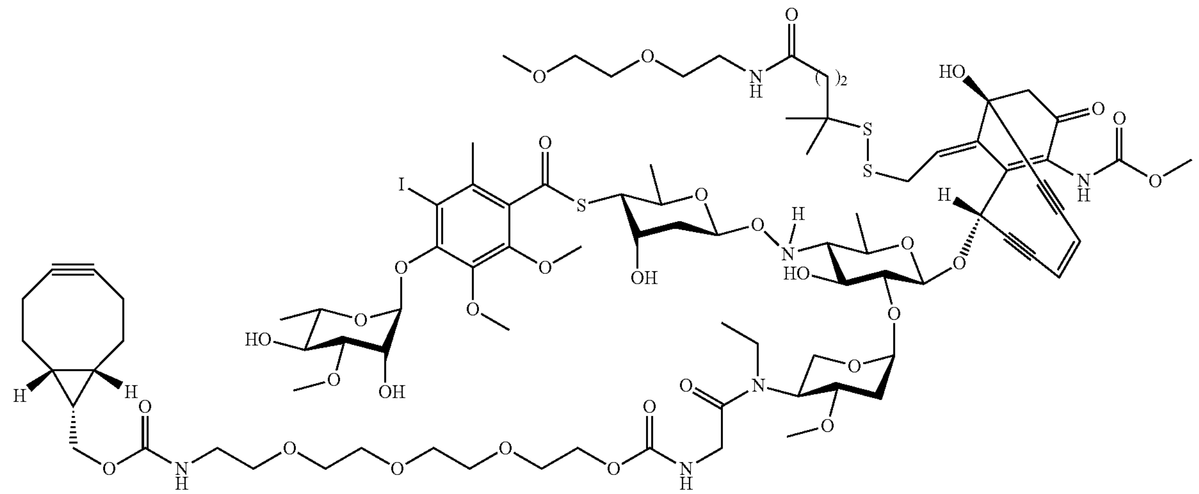

155

To a solution of 138 (3.0 mg, 1.9 μmol) in DMF (180 μL) were added a solution of 41 (1.5 mg, 2.8 μmol) in DMF (34 μL) and a 10% solution of $Et_3N$ in DMF (7.9 μL, 0.57 mg, 5.6 μmol). The mixture was left standing for 75 min, diluted with DCM (700 μL) and purified by silica column chromatography (DCM→10% MeOH in DCM). The desired product was obtained as a colorless film (3.2 mg, 1.6 μmol). LCMS (ESI+) calculated for $C_{87}H_{126}IN_6O_{32}S_3^+$ (M+H⁺) 1989.66, found 1991.31.

Example 5-15: Synthesis of Acetylene- or DBCO-Modified Calicheamicin Derivatives 156 and 157, Respectively, with Cleavable Linker

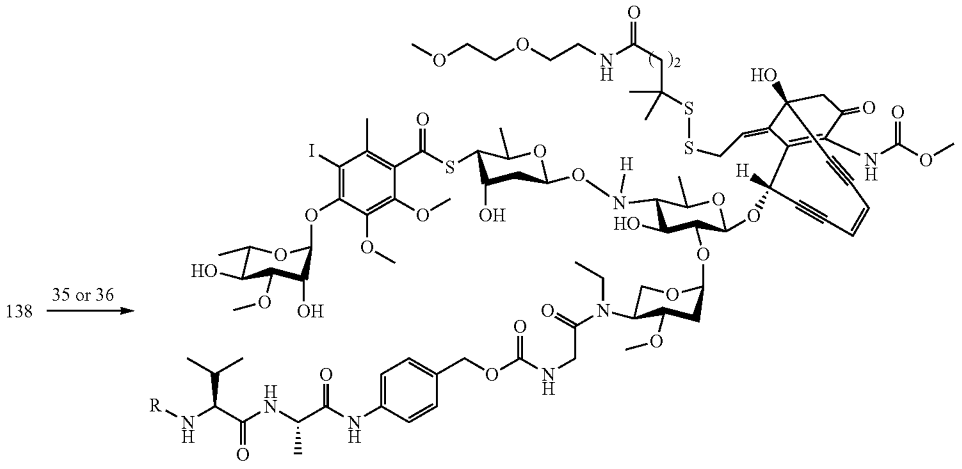

156, R =

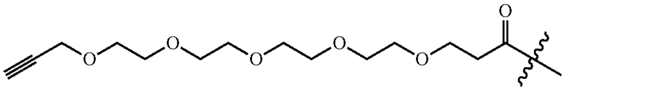

157, R =

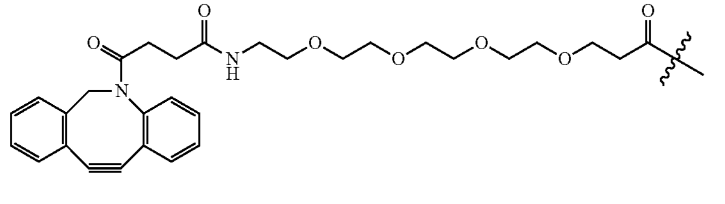

To a solution of 138 (2.8 mg, 1.8 μmol) in DMF (360 μL) were added a solution of 35 (1.6 mg, 2.2 μmol) in DMF (33 μL) and $Et_3N$ (1.3 μL, 0.91 mg). The mixture was left standing for 20h and 2,2'-(ethylenedioxy)bis(ethylamine) (1.3 μL, 1.3 mg, 8.8 μmol) was added. After 1.5h, the r.m. was purified by RP-HPLC (C18, 30%→90% MeCN (1% AcOH) in $H_2O$ (1% AcOH). The desired product was obtained as a colorless film (2.3 mg, 1.0 μmol, 48%) LCMS ($ESI^+$) calculated for $C_{97}H_{141}IN_8O_{35}S_3{}^{2}$. ($M+H^+$) 1100.89, found 1101.11.

To a solution of 138 (3.5 mg, 2.2 μmol) in DMF (220 μL) were added a solution of 36 (3.3 mg, 3.3 μmol) in DMF (97 μL) and $Et_3N$ (3.1 μL, 2.2 mg, 22 μmol). The mixture was left standing for 100 min, diluted with DMF (100 μL) and purified by RP-HPLC (C18, 30%→90% MeCN (1% AcOH) in $H_2O$ (1% AcOH). The desired product was obtained as a colorless film (3.9 mg, 1.6 μmol). LCMS (ESI+) calculated for $C_{113}H_{153}IN_{10}O_{36}S_3{}^{2+}$ ($M+2H^+$)/2 1224.93, found 1225.40.

Example 5-16: Synthesis of Disulphide-Linked BCN-Calicheamin Derivative 158 with Cleavable Linker

114

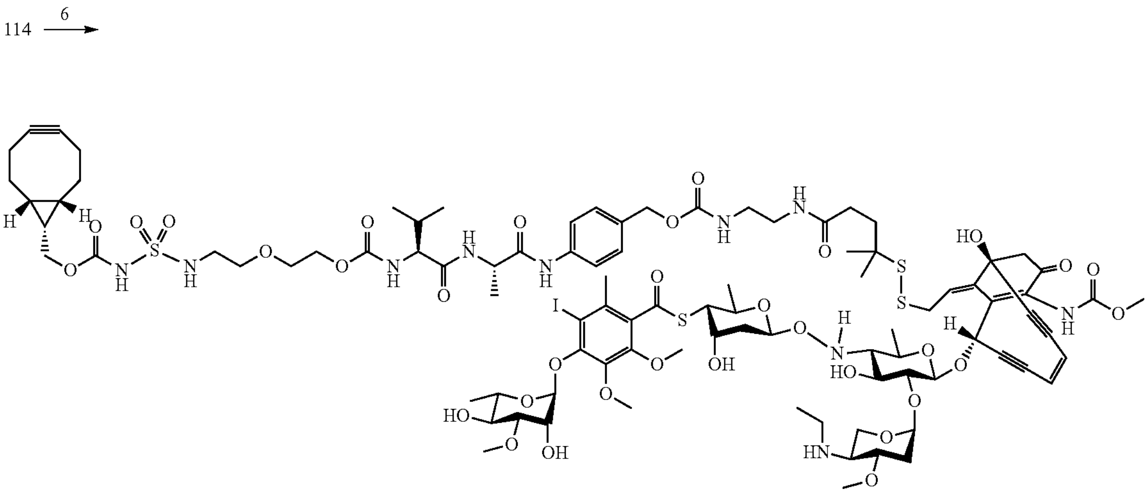

158

To a solution of 114 (2.6 mg, 1.8 μmol) in DMF (352 μL) were added a solution of 6 (2.2 mg, 2.64 μmol) in DMF (171 μL) and $Et_3N$ (1.2 μL, 0.89 mg, 8.8 μmol). After 3h, the mixture was purified by RP-HPLC (30%→90% MeCN (1% AcOH) in H2O (1% AcOH). The product was obtained as colorless film (2.6 mg, 1.2 μmol, 68%). LCMS ($ESI^+$) calculated for $C_{94}H_{133}IN_{10}O_{33}S_4{}^{2+}$ ($M+2H^+$)/2 1092.85, found 1092.89.

Example 5-16: Synthesis of Disulphide-Linked BCN-(Calicheamin)$_2$ Derivative 159 with Cleavable Linker

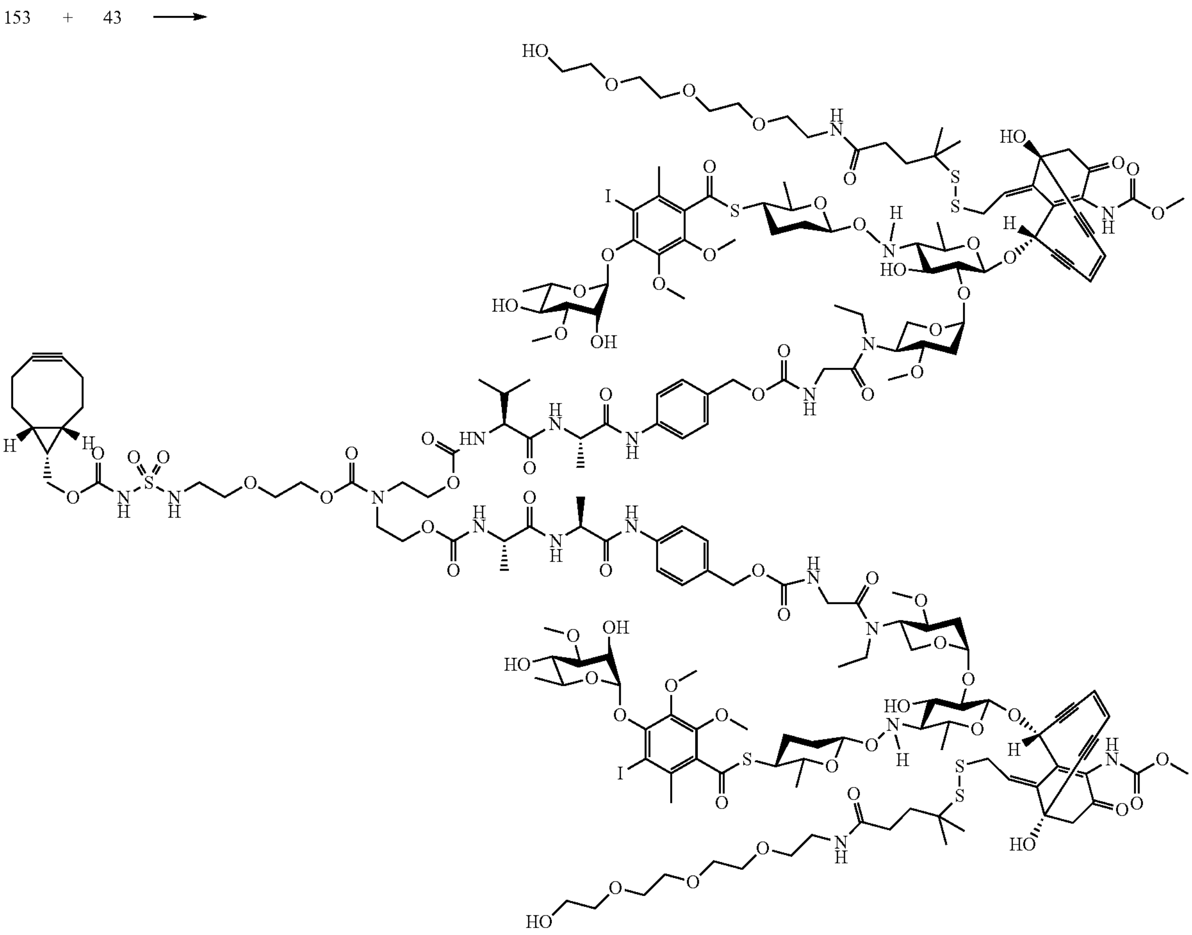

159

To a vial containing 153 (4.90 mg, 2.46 μmol, 1.00 equiv.) in DMF (86.4 μL) was added a solution of 43 (1.01 mg, 1.23 μmol, 0.50 equiv.) followed by $Et_3N$ (0.68 μL). The resulting brown solution was left at rt for 15.5 hours and was then partially concentrated to a volume of 40-45 μL. The concentrated reaction mixture was left for another 4 hours and was then purified by RP-HPLC (018, 30%→90% MeCN (1% AcOH) in $H_2O$ (1% AcOH). The desired product was obtained as a white solid (1.0 mg, 0.22 μmol, 18%). LCMS (ESI+) calculated for $C_{194}H_{278}I_2N_{19}O_{73}S_7^{3+}$ (M+3H$^+$)/3 1507.16, found 1507.38.

Example 6-1: Conjugation of Azido-Remodeled Trastuzumab 17 with BCN-Val-Cit-PABC-Gly-Calicheamicin 9 to Obtain Conjugate ADC170

To a solution of trastuzumab-(6-$N_3$-GalNAc)$_2$ (17) (90 μL, 2.58 mg, 28.7 mg/ml in PBS pH 7.4), prepared as described in WO 2014/065661 and WO 2016/170186, was added DMF (7.5 μL) and 9 (35 μL, 10 mM solution in DMF), to form conjugate 18 (also referred to as ADC170). The reaction was incubated at rt for approximately 40 h followed by purification on a Superdex200 10/300 GL (GE Healthcare) on an AKTA Purifier-10 (GE Healthcare). Mass spectral analysis of the fabricator-digested sample showed one major product (observed mass 26496 Da, approximately 90% of total Fc/2 fragment), corresponding to the conjugated Fc/2 fragment. RP-HPLC analysis of the reduced sample indicated an average OAR of 1.82.

Example 6-2: Conjugation of Azide-Modified Trastuzumab 17 with BCN-Calicheamicin 156 to Obtain Conjugate ADC211

To a solution of trastuzumab-(6-$N_3$-GalNAc)$_2$ (17) (210 μL, 5 mg, 24 mg/ml in PBS pH 7.4) was added PBS pH 7.4 (180 μL) and compound 156 (167 μL, 2.4 mM solution in DMF). In a separate tube, to a solution of $CuSO_4$ (71 μL, 15 mM solution in MQ) was added tris[(1-hydroxypropyl-1H-1,2,3-triazol-4-yl)methyl]amine (THPTA) (13 μL, 160 mM solution in DMF), amino guanidine·HCl (53 μL, 100 mM solution in MQ) and sodium ascorbate (40 μL, 400 mM solution in MQ). The THPTA-$CuSO_4$ complex was mixed and incubated at rt for 10 minutes. An aliquot of the THPTA-$CuSO_4$ complex (111 μL) was added to the solution containing trastuzumab-(6-$N_3$-GalNAc)$_2$ (17) and compound 156. The reaction was mixed and incubated at rt.

After 1 hr the reaction was quenched by adding PBS pH 7.4 containing 1 mM EDTA (2.7 mL). The reaction was concentrated to approximately 0.5 mL by spinfiltration (Amicon Ultra-0.5, Ultracel-10 Membrane, Millipore) followed by purification on a Superdex200 10/300 GL (GE Healthcare) on an AKTA Purifier-10 (GE Healthcare). Mass spectral analysis of the fabricator-digested sample showed one major product (observed mass 26572 Da, approximately 90% of total Fc/2 fragment, calculated mass 26563 Da), corresponding to the conjugated Fc/2 fragment.

Example 6-3: Conjugation of Azide-Modified Trastuzumab 17 with BCN-Calicheamicin 149 to Obtain Conjugate ADC212

To a solution of trastuzumab-(6-$N_3$-GalNAc)$_2$ (17) (136 μL, 3 mg, 22 mg/ml in PBS pH 7.4) was added DMF (19.8 μL) and compound 149 (19.8 μL, 5 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26794 Da, observed mass 26801 Da, approximately 90% of total Fc/2 fragment), corresponding to the conjugated Fc/2 fragment.

Example 6-4: Conjugation of Azide-Modified Trastuzumab 17 with BCN-Calicheamicin 139 to Obtain Conjugate ADC213

To a solution of trastuzumab-(6-$N_3$-GalNAc)$_2$ (17) (100 μL, 3 mg, 31.7 mg/ml in PBS pH 7.4) was added PG (70 μL) and compound 139 (30 μL, 10 mM solution in DMF). The reaction was incubated at rt for approximately 48 hrs followed by purification on a Superdex200 10/300 GL (GE Healthcare) on an AKTA Purifier-10 (GE Healthcare). Mass spectral analysis of the fabricator-digested sample showed one major product (calculated mass 26670 Da, observed mass 26678 Da, approximately 90% of total Fc/2 fragment), corresponding to the conjugated Fc/2 fragment.

Example 6-5: Conjugation of Azide-Modified Trastuzumab 17 with BCN-Calicheamicin 140 to Obtain Conjugate ADC214

To a solution of trastuzumab-(6-$N_3$-GalNAc)$_2$ (17) (100 μL, 3 mg, 31.7 mg/ml in PBS pH 7.4) was added PG (70 μL) and compound 140 (30 μL, 10 mM solution in DMF). Since the reaction mixture was not clear. An additional 20 μL PG was added. Hereafter the reaction mixture was still hazy. An additional 10 μL PG was added. The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26584 Da, observed mass 26592 Da, approximately 90% of total Fc/2 fragment), corresponding to the conjugated Fc/2 fragment.

Example 6-6: Conjugation of Azide-Modified Trastuzumab 17 with BCN-Calicheamicin 150 to Obtain Conjugate ADC215

To a solution of trastuzumab-(6-$N_3$-GalNAc)$_2$ (17) (136 μL, 3 mg, 22 mg/ml in PBS pH 7.4) was added DMF (20 μL) and compound 150 (20 μL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26663 Da, observed mass 26670 Da, approximately 90% of total Fc/2 fragment), corresponding to the conjugated Fc/2 fragment.

Example 6-7: Conjugation of Azide-Modified Trastuzumab 17 with BCN-Calicheamicin 157 to Obtain Conjugate ADC216

To a solution of trastuzumab-(6-$N_3$-GalNAc)$_2$ (17) (136 μL, 3 mg, 22 mg/ml in PBS pH 7.4) was added PG (116 μL) and compound 157 (20 μL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26811 Da, observed mass 26819 Da, approximately 90% of total Fc/2 fragment), corresponding to the conjugated Fc/2 fragment.

Example 6-8: Conjugation of Azide-Modified Trastuzumab 17 with BCN-Calicheamicin 155 to Obtain Conjugate ADC217

To a solution of trastuzumab-(6-$N_3$-GalNAc)$_2$ (17) (136 μL, 3 mg, 22 mg/ml in PBS pH 7.4) was added PG (116 μL) and compound 155 (20 μL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26353 Da, observed mass 26360 Da, approximately 90% of total Fc/2 fragment), corresponding to the conjugated Fc/2 fragment.

Example 6-9: Conjugation of Azide-Modified Trastuzumab 17 with BCN-Calicheamicin 134 to Obtain Conjugate ADC218

To a solution of trastuzumab-(6-$N_3$-GalNAc)$_2$ (17) (136 μL, 3 mg, 22 mg/ml in PBS pH 7.4) was added PG (106 μL) and compound 134 (30 μL, 10 mM solution in DMF). The reactions mixture was not clear. An additional amount of PG was added (2×14.4 μL PG) the mixture did not become entirely clear. The reaction was incubated at rt for approximately 48 hrs followed by purification on a Superdex200 10/300 GL (GE Healthcare) on an AKTA Purifier-10 (GE Healthcare). Mass spectral analysis of the fabricator-digested sample showed one major product (calculated mass 26640 Da, observed mass 26647 Da, approximately 90% of total Fc/2 fragment), corresponding to the conjugated Fc/2 fragment.

Example 6-10: Conjugation of Azide-Modified Trastuzumab 17 with BCN-Calicheamicin 127 to Obtain Conjugate ADC219

To a solution of trastuzumab-(6-$N_3$-GalNAc)$_2$ (17) (136 μL, 3 mg, 22 mg/ml in PBS pH 7.4) was added PG (122 μL) and compound 127 (13.3 μL, 10 mM solution in DMF). The reaction was incubated at rt for approximately 48 hrs. After 2 days complete conversion has not been reached. The sample was centrifuged due to precipitation. Five equivalents in 50% PG (9 μL 10 mM 127, 9 μL PG) were added and the reaction was incubated at rt for 20 hrs followed by purification on a Superdex200 10/300 GL (GE Healthcare) on an AKTA Purifier-10 (GE Healthcare). Mass spectral analysis of the fabricator-digested sample showed one major product (calculated mass 26527 Da, observed mass 26535 Da, approximately 90% of total Fc/2 fragment), corresponding to the conjugated Fc/2 fragment.

Example 6-11: Conjugation of Azide-Modified Trastuzumab 17 with BCN-Calicheamicin 136 to Obtain Conjugate ADC220

To a solution of trastuzumab-(6-$N_3$-GalNAc)$_2$ (17) (91 µL, 2 mg, 22 mg/ml in PBS pH 7.4) was added PG (77 µL) and compound 136 (15.8 µL, 10 mM solution in DMF). The reaction was incubated at rt for approximately 24 hrs followed by purification on a Superdex200 10/300 GL (GE Healthcare) on an AKTA Purifier-10 (GE Healthcare). Mass spectral analysis of the fabricator-digested sample showed one major product (calculated mass 26771 Da, observed mass 26778 Da, approximately 90% of total Fc/2 fragment), corresponding to the conjugated Fc/2 fragment.

Example 6-12: Conjugation of Azide-Modified Trastuzumab 17 with BCN-Calicheamicin 101 to Obtain Conjugate ADC221

To a solution of trastuzumab-(6-$N_3$-GalNAc)$_2$ (17) (136 µL, 3 mg, 22 mg/ml in PBS pH 7.4) was added PG (116 µL) and compound 101 (20 µL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26437 Da, observed mass 26444 Da, approximately 90% of total Fc/2 fragment), corresponding to the conjugated Fc/2 fragment.

Example 6-13: Conjugation of Azide-Modified Trastuzumab 17 with BCN-Calicheamicin 121 to Obtain Conjugate ADC222

To a solution of trastuzumab-(6-$N_3$-GalNAc)$_2$ (17) (136 µL, 3 mg, 22 mg/ml in PBS pH 7.4) was added PG (122 µL) and compound 121 (13.3 µL, 10 mM solution in DMF). The reaction was incubated at rt for approximately 48 hrs followed by purification on a Superdex200 10/300 GL (GE Healthcare) on an AKTA Purifier-10 (GE Healthcare). Mass spectral analysis of the fabricator-digested sample showed one major product (calculated mass 26339 Da, observed mass 26347 Da, approximately 90% of total Fc/2 fragment), corresponding to the conjugated Fc/2 fragment.

Example 6-14: Conjugation of Azide-Modified Trastuzumab 17 with BCN-Calicheamicin 146 to Obtain Conjugate ADC224

To a solution of trastuzumab-(6-$N_3$-GalNAc)$_2$ (17) (136 µL, 3 mg, 22 mg/ml in PBS pH 7.4) was added PG (108.8 µL) and compound 146 (27.2 µL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26576 Da, observed mass 26582 Da, approximately 90% of total Fc/2 fragment), corresponding to the conjugated Fc/2 fragment.

Example 6-15: Conjugation of Azide-Modified Trastuzumab 17 with BCN-Calicheamicin 142 to Obtain Conjugate ADC246

To a solution of trastuzumab-(6-$N_3$-GalNAc)$_2$ (17) (136 µL, 3 mg, 22 mg/ml in PBS pH 7.4) was added PG (90.6 µL) and compound 142 (45.4 µL, 6 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26483 Da, observed mass 26488 Da, approximately 90% of total Fc/2 fragment), corresponding to the conjugated Fc/2 fragment.

Example 6-16: Conjugation of Azide-Modified Trastuzumab 17 with BCN-Calicheamicin 158 to Obtain Conjugate ADC247

To a solution of trastuzumab-(6-$N_3$-GalNAc)$_2$ (17) (136 µL, 3 mg, 22 mg/ml in PBS pH 7.4) was added PG (108.8 µL) and compound 158 (27.2 µL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 26547 Da, observed mass 26549 Da, approximately 90% of total Fc/2 fragment), corresponding to the conjugated Fc/2 fragment.

Example 6-17: Conjugation of Azide-Modified Trastuzumab 17 with BCN-Calicheamicin 130 to Obtain Conjugate ADC249

To a solution of trastuzumab-(6-$N_3$-GalNAc)$_2$ (17) (91 µL, 3 mg, 22 mg/ml in PBS pH 7.4) was added compound 130 (91 µL, 2.2 mM solution in PG). The reaction was incubated at rt for approximately 144 hrs followed by purification on a Superdex200 10/300 GL (GE Healthcare) on an AKTA Purifier-10 (GE Healthcare). Mass spectral analysis of the fabricator-digested sample showed one major product (calculated mass 26737 Da, observed mass 26740 Da, approximately 90% of total Fc/2 fragment), corresponding to the conjugated Fc/2 fragment.

Example 6-18: Conjugation of Azide-Modified Trastuzumab 17 with BCN-Calicheamicin 159 to Obtain Conjugate ADC250

To a solution of trastuzumab-(6-$N_3$-GalNAc)$_2$ (17) (68 µL, 1.5 mg, 22 mg/ml in PBS pH 7.4) was added PG (75 µL), DMF (6 µL) and compound 159 (16 µL, 10 mM solution in DMF). The reaction was incubated at rt for approximately 20 hrs followed by purification on a Superdex200 10/300 GL (GE Healthcare) on an AKTA Purifier-10 (GE Healthcare). Mass spectral analysis of the fabricator-digested sample showed one major product (calculated mass 28880 Da, observed mass 28884 Da, approximately 90% of total Fc/2 fragment), corresponding to the conjugated Fc/2 fragment.

Example 7-1: In Vitro Cytotoxicity

BT-474 (Her2 3+), MDA-MB-453 (Her2 2+) and JIMT-1 (Her2 1+) cells were plated in 96-well plates (5000 cells/well) in RPMI 1640 GlutaMAX (Invitrogen) supplemented with 10% fetal calf serum (FCS) (Invitrogen, 200 µL/well)

and incubated overnight in a humidified atmosphere at 37° C. and 5% $CO_2$. Kadcyla and conjugate 18 were added in quadruplo in a three-fold dilution series to obtain a final concentration ranging from 0.1 pM to 18 nM. The cells were incubated for 5 days in a humidified atmosphere at 37° C. and 5% $CO_2$. The culture medium was replaced by 0.01 mg/mL resazurin (Sigma Aldrich) in RPMI 1640 GlutaMAX supplemented with 10% FCS (200 µL/well). After approximately 2 hours in a humidified atmosphere at 37° C. and 5% $CO_2$ the fluorescence was detected with a fluorescence plate reader (Envision multipabel plate reader) at 531 nm excitation and 590 nm emission. The relative fluorescent units (RFU) were normalized to cell viability percentage by setting wells without cells at 0% viability and wells with untreated cells at 100% viability. IC50 values were calculated by non-linear regression using Graphpad prism software and are shown in Table 1 below.

TABLE 1

$IC_{50}$ values for Kadcyla and ADC170.

| Conjugate | BT-474 (Her2 3+) | MDA-MB-453 (Her2 2+) | JIMT-1 (Her2 1+) |
|---|---|---|---|
| Kadcyla | 460 pM | 613 pM | No effect |
| ADC170 | 200 pM | 155 pM | 41 pM |

Example 7-2: In Vitro Cytotoxicity

Figure 3:
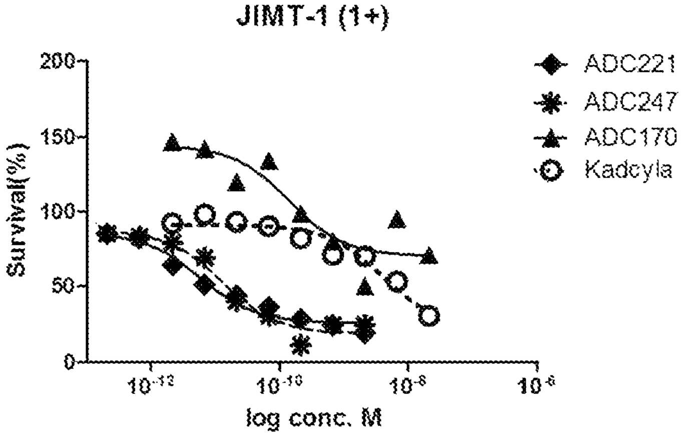
FIG. 3 shows the in vitro cytotoxicity plots for calicheamicin-based ADC170, ADC221, ADC247 and Kadcyla® on HER2 1+-positive JIMT-1 cell lines.
Figure 4A:
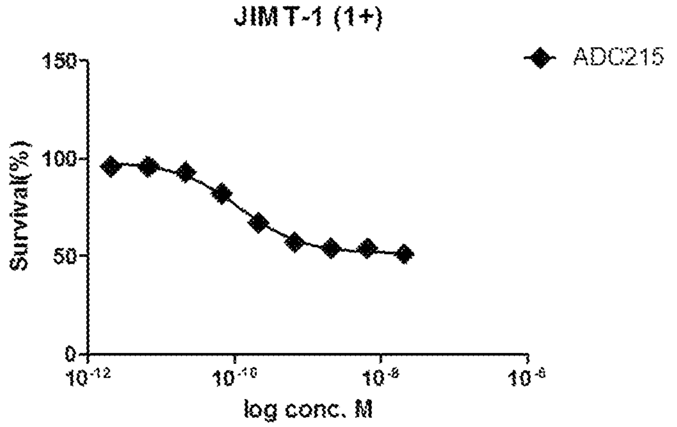
FIG. 4A shows the in vitro cytotoxicity plots for calicheamicin-based ADC215 and Kadcyla® on HER2 1+-positive JIMT-1 cell lines.
Figure 4B:
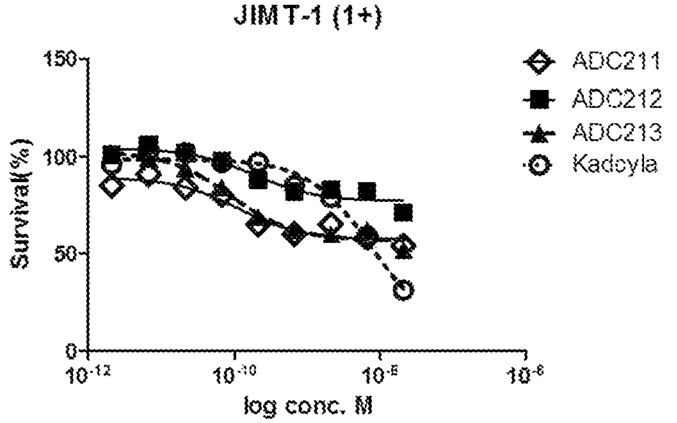
FIG. 4B shows the in vitro cytotoxicity plots for calicheamicin-based ADC211-213 and Kadcyla® on HER2 1+-positive JIMT-1 cell lines.
Figure 4C:
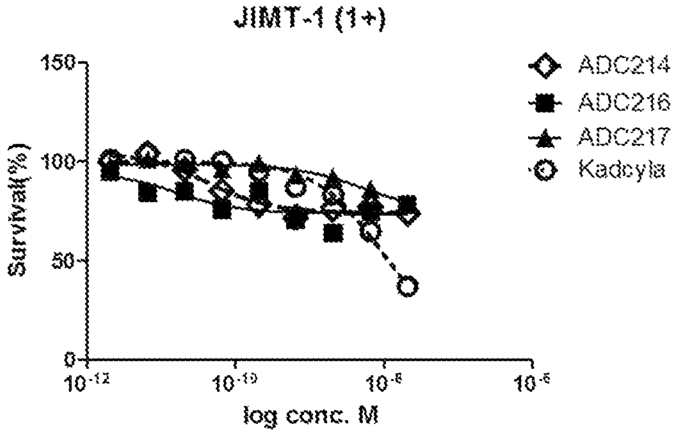
FIG. 4C shows the in vitro cytotoxicity plots for calicheamicin-based ADC214, ADC216 and ADC217 and Kadcyla® on HER2 1+-positive JIMT-1 cell lines.
Figure 4D:
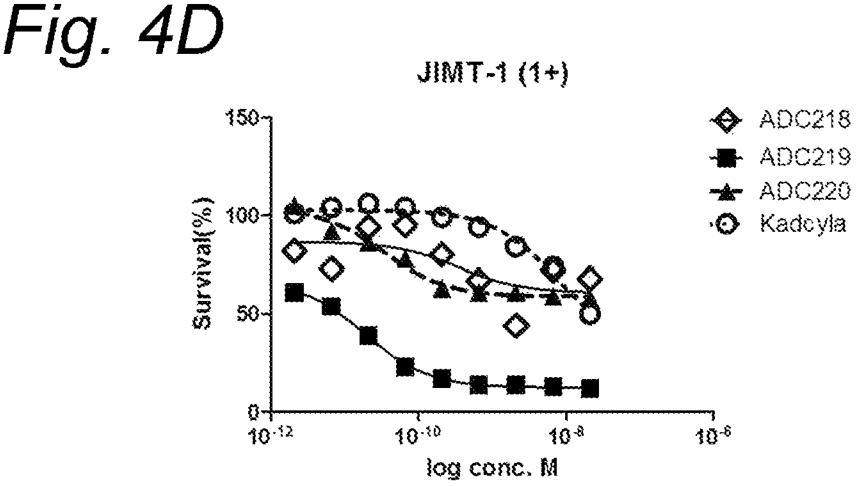
FIG. 4D shows the in vitro cytotoxicity plots for calicheamicin-based ADC218-220 and Kadcyla® on HER2 1+-positive JIMT-1 cell lines.
Figure 4E:
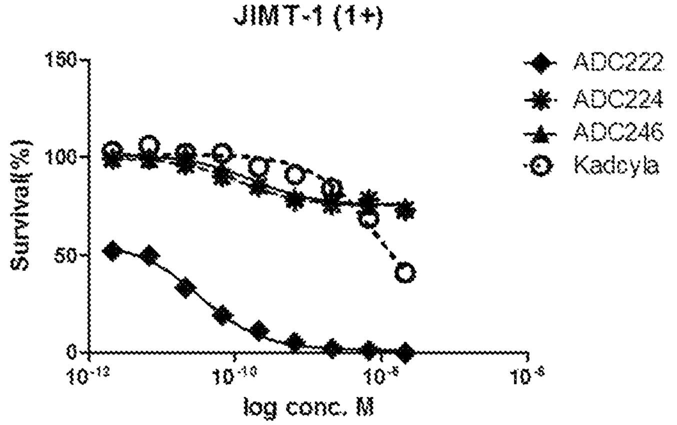
FIG. 4E shows the in vitro cytotoxicity plots for calicheamicin-based ADC222, ADC224 and ADC246, and Kadcyla® on HER2 1+-positive JIMT-1 cell lines.
Figure 5:
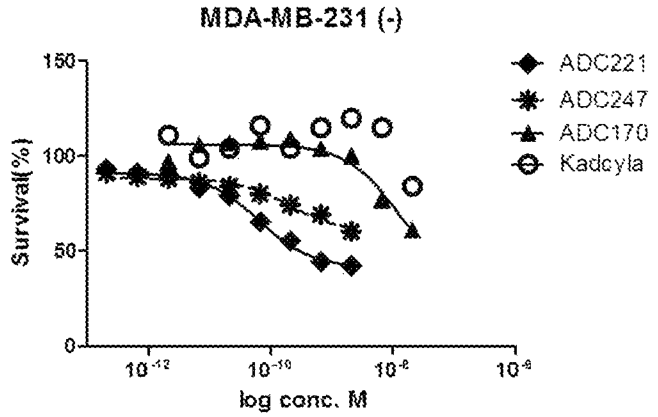
FIG. 5 shows the in vitro cytotoxicity plots for calicheamicin-based ADCs ADC170, ADC221, ADC247 and Kadcyla® on HER2 negative MDA-MB-231 cell lines.
Figure 6A:
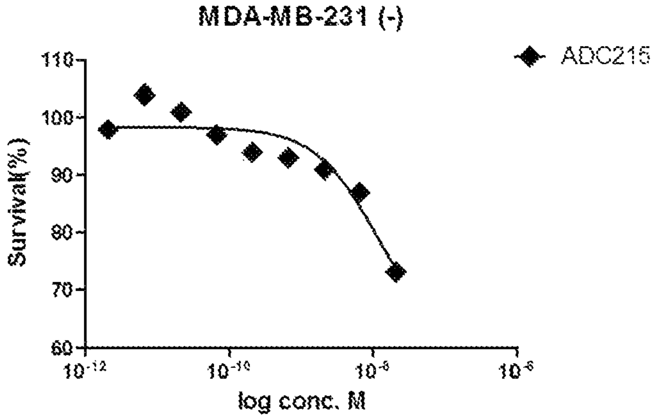
FIG. 6A shows the in vitro cytotoxicity plots for calicheamicin-based ADC215 and Kadcyla® on HER2 negative MDA-MB-231 cell lines.
Figure 6B:
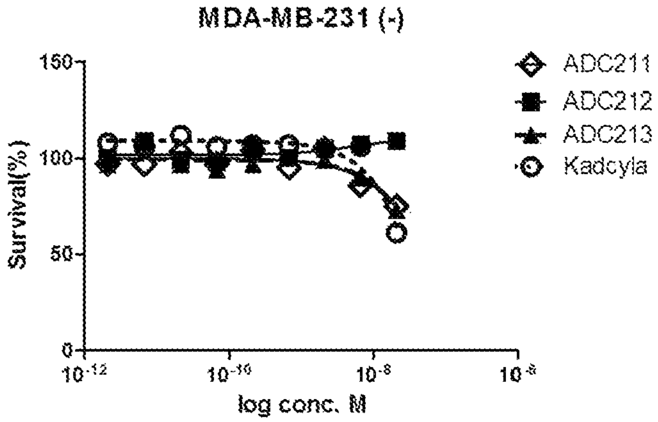
FIG. 6B shows the in vitro cytotoxicity plots for calicheamicin-based ADC211-213 and Kadcyla® on HER2 negative MDA-MB-231 cell lines.
Figure 6C:
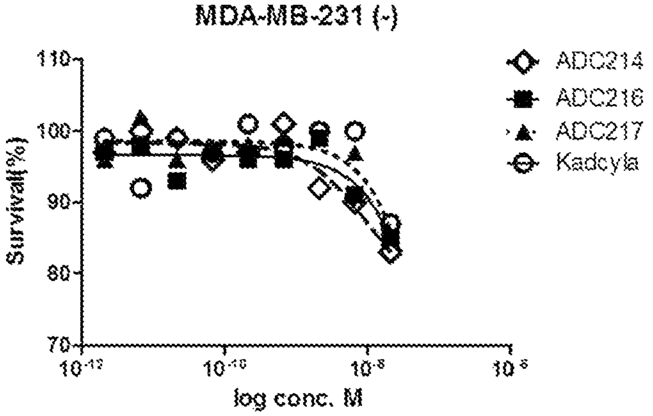
FIG. 6C shows the in vitro cytotoxicity plots for calicheamicin-based ADC214, ADC216 and ADC217 and Kadcyla® on HER2 negative MDA-MB-231 cell lines.
Figure 6D:
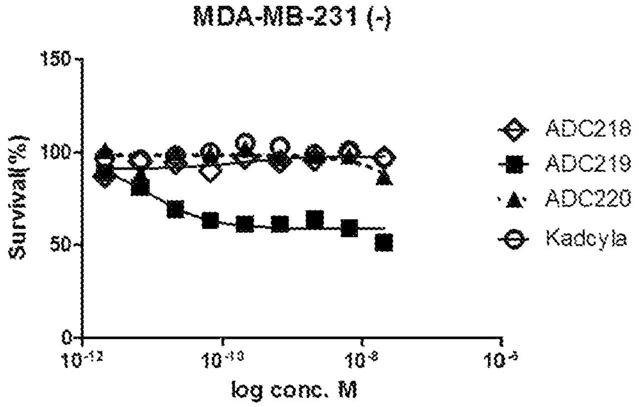
FIG. 6D shows the in vitro cytotoxicity plots for calicheamicin-based ADC218-220 and Kadcyla® on HER2 negative MDA-MB-231 cell lines.
Figure 6E:
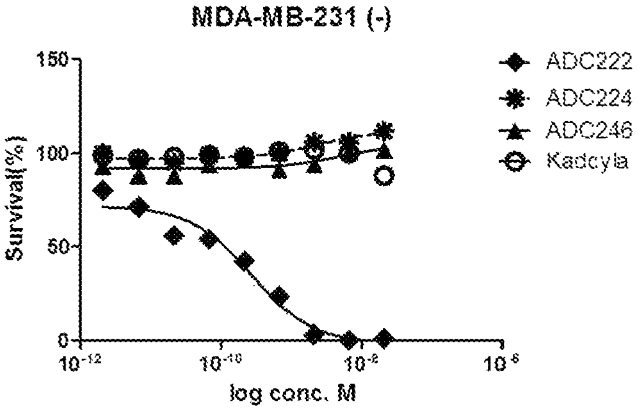
FIG. 6E shows the in vitro cytotoxicity plots for calicheamicin-based ADC222, ADC224 and ADC246, and Kadcyla® on HER2 negative MDA-MB-231 cell lines.

BT-474 (Her2 3+), JIMT-1 (Her2 1+) and MDA-MB-231 (Her2−) cells were plated in 96-well plates (5000 cells/well) in RPMI 1640 GlutaMAX (Invitrogen) supplemented with 10% fetal calf serum (FCS) (Invitrogen, 200 µL/well) and incubated overnight in a humidified atmosphere at 37° C. and 5% $CO_2$. Kadcyla and compounds ADC170, ADC211-ADC220, ADC222, ADC224 and ADC246 were added in quadruplo in a √10-fold dilution series to obtain a final concentration ranging from 2.1 pM to 21 nM. The cells were incubated for 5 days in a humidified atmosphere at 37° C. and 5% $CO_2$. The culture medium was replaced by 0.01 mg/mL resazurin (Sigma Aldrich) in RPMI 1640 GlutaMAX supplemented with 10% FCS (200 µL/well). After approximately 3 hours in a humidified atmosphere at 37° C. and 5% $CO_2$ the fluorescence was detected with a fluorescence plate reader (Envision multilabel plate reader) at 531 nm excitation and 590 nm emission. The relative fluorescent units (RFU) were normalized to cell viability percentage by setting wells without cells at 0% viability and wells with untreated cells at 100% viability. Dose-response curves for Kadcyla and ADC170 on BT-474 are provided in FIG. 1. Dose-response curves for Kadcyla and ADC170 on JIMT-1 are provided in FIG. 3. Dose-response curves for Kadcyla and ADC170 on MDA-MB-231 are provided in FIG. 5. Dose-response curves for Kadcyla and ADC211-ADC220, ADC222, ADC224 and ADC246 on BT-474 are provided in FIG. 2. Dose-response curves for Kadcyla and ADC211-ADC220, ADC222, ADC224 and ADC246 on JIMT-1 are provided in FIG. 4. Dose-response curves for Kadcyla and ADC211-ADC220, ADC222, ADC224 and ADC246 on MDA-MB-231 are provided in FIG. 6. $IC_{50}$ values were calculated by non-linear regression using Graphpad prism software and are shown in Table 2 below:

TABLE 2

$IC_{50}$ values for Kadcyla and ADC170, ADC211-ADC220, ADC222, ADC224 and ADC246

| | BT-474 (Her2 3+) | JIMT-1 (Her2 1+) | MDA-MB-231 (Her2−) |
|---|---|---|---|
| Kadcyla | 49 pM | >1000 pM | >1000 pM |
| ADC211 | 292 pM | 143 pM | >1000 pM |
| ADC212 | 354 pM | 240 pM | >1000 pM |
| ADC213 | 189 pM | 112 pM | >1000 pM |
| ADC214 | 178 pM | 56 pM | >1000 pM |
| ADC215 | 223 pM | 116 pM | >1000 pM |
| ADC216 | 140 pM | 21 pM | >1000 pM |
| ADC217 | 582 pM | >1000 pM | >1000 pM |
| ADC218 | 182 pM | 354 pM | 176 pM |
| ADC219 | 2 pM | 19 pM | 9 pM |
| ADC220 | 170 pM | 34 pM | >1000 pM |
| ADC222 | 6 pM | 33 pM | 263 pM |
| ADC224 | 277 pM | 120 pM | >1000 pM |
| ADC246 | 295 pM | 174 pM | >1000 pM |
| ADC170 | 268 pM | 138 pM | >1000 pM |

Example 7-3: In Vitro Cytotoxicity

BT-474 (Her2 3+), JIMT-1 (Her2 1+) and MDA-MB-231 (Her2−) cells were plated in 96-well plates (5000 cells/well) in RPMI 1640 GlutaMAX (Invitrogen) supplemented with 10% fetal calf serum (FCS) (Invitrogen, 200 µL/well) and incubated overnight in a humidified atmosphere at 37° C. and 5% $CO_2$. Kadcyla and compound ADC221 and ADC247 were added in quadruplo in a 10-fold dilution series to obtain a final concentration ranging from 0.21 pM to 2.1 nM. The cells were incubated for 5 days in a humidified atmosphere at 37° C. and 5% $CO_2$. The culture medium was replaced by 0.01 mg/mL resazurin (Sigma Aldrich) in RPMI 1640 GlutaMAX supplemented with 10% FCS (200 µL/well). After approximately 3 hours in a humidified atmosphere at 37° C. and 5% $CO_2$ the fluorescence was detected with a fluorescence plate reader (Envision multilabel plate reader) at 531 nm excitation and 590 nm emission. The relative fluorescent units (RFU) were normalized to cell viability percentage by setting wells without cells at 0% viability and wells with untreated cells at 100% viability. Dose-response curves for Kadcyla and ADC221 and ADC247 on BT-474 are provided in FIG. 1. Dose-response curves for Kadcyla and ADC221 and ADC247 on JIMT-1 are provided in FIG. 3. Dose-response curves for Kadcyla and ADC221 and ADC247 on MDA-MB-231 are provided in FIG. 5. $IC_{50}$ values were calculated by non-linear regression using Graphpad prism software and are shown in Table 3 below:

TABLE 3

$IC_{50}$ values for Kadcyla and ADC221 and ADC247

| Conjugate | BT-474 (Her2 3+) | JIMT-1 (Her2 1+) | MDA-MB-231 (Her2−) |
|---|---|---|---|
| Kadcyla | 70 pM | >1000 pM | >1000 pM |
| ADC221 | 52 pM | 6 pM | 64 pM |
| ADC247 | 64 pM | 13 pM | 206 pM |

Example 8-1: Aggregation Study

The effect of different calicheamicin variants on the aggregation potential of the corresponding ADCs was studied using 12 ADCs consisting of trastuzumab conjugated to different calicheamicin variants. The naked antibody was included as a control. ADCs (300 μg each) were diluted in PBS pH 7.4 to a concentration of 1 mg/mL and incubated at 37° C. The aggregation level was measured after 0, 2, 7, 14 and 21 days using a XBridge Protein BEH SEC 200 Å column (Waters) on an Agilent 1100 HPLC. Aggregation levels are shown in Table 4 below:

TABLE 4

Aggregation levels (percentage) of calicheamicin ADCs incubated in PBS pH 7.4 at 37° C.

| Conjugate | Incubation time (days) 0 | 2 | 7 | 14 | 21 |
|---|---|---|---|---|---|
| trastuzumab | 0.6 | 0.0 | 0.0 | 0.0 | 0.0 |
| ADC211 | 0.0 | 0.0 | 0.0 | 0.0 | 0.0 |
| ADC212 | 0.0 | 0.0 | 0.0 | 0.0 | 0.0 |
| ADC213 | 0.0 | 0.0 | 0.0 | 0.0 | 0.0 |
| ADC214 | 0.0 | 0.0 | 0.0 | 0.0 | 0.0 |
| ADC215 | 0.0 | 0.0 | 0.0 | 0.0 | 0.0 |
| ADC216 | 0.0 | 0.0 | 0.0 | 0.0 | 0.0 |
| ADC217 | 0.0 | 0.0 | 0.0 | 0.0 | 0.0 |
| ADC218 | 0.0 | 0.0 | 0.0 | 0.0 | 0.0 |
| ADC219 | 0.0 | 0.0 | 0.0 | 0.0 | 0.0 |
| ADC220 | 0.0 | 0.0 | 0.0 | 0.0 | 0.0 |
| ADC221 | 0.0 | 0.0 | 0.0 | 0.0 | 0.8 |
| ADC222 | 0.0 | 0.0 | 0.0 | 0.0 | 0.0 |

Example 8-2: Accelerated Aggregation Study

The effect of different calicheamicin variants on the aggregation potential of the corresponding ADCs was studied using 12 ADCs consisting of trastuzumab conjugated to different calicheamicin variants. The naked antibody was included as a control. For each ADO, the pH was adjusted to 5.0 by adding 0.1 M sodium citrate pH 4.65 (50 μL) to the solution of ADC (250 μL, 300 μg, 1.2 mg/mL in PBS pH 7.4). The ADCs were incubated at 40° C. and the aggregation level was measured after 0, 2, 7, 14 and 21 days using a XBridge Protein BEH SEC 200 Å column (Waters) on an Agilent 1100 HPLC. Aggregation levels are shown in Table 5 below.

TABLE 5

Aggregation levels (percentage) of calicheamicin ADCs incubated in sodium citrate/PBS pH 5.0 at 40° C.

| Conjugate | Incubation time (days) 0 | 2 | 7 | 14 | 21 |
|---|---|---|---|---|---|
| trastuzumab | 0.6 | 0.0 | 0.0 | 0.0 | 0.0 |
| ADC211 | 0.0 | 0.3 | 0.7 | 0.9 | 1.0 |
| ADC212 | 0.0 | 0.0 | 0.2 | 0.3 | 0.3 |
| ADC213 | 0.0 | 0.0 | 0.0 | 0.3 | 0.3 |
| ADC214 | 0.0 | 0.0 | 0.2 | 0.6 | 0.6 |
| ADC215 | 0.0 | 0.0 | 0.2 | 0.3 | 0.4 |
| ADC216 | 0.0 | 0.0 | 0.3 | 0.4 | 0.6 |
| ADC217 | 0.0 | 0.0 | 0.0 | 0.0 | 0.0 |
| ADC218 | 0.0 | 0.2 | 0.7 | 1.0 | 1.3 |
| ADC219 | 0.0 | 0.0 | 0.4 | 0.6 | 0.9 |
| ADC220 | 0.0 | 0.0 | 0.0 | 0.3 | 0.3 |
| ADC221 | 0.0 | 0.7 | 2.6 | 4.0 | 4.6 |
| ADC222 | 0.0 | 0.0 | 0.0 | 0.0 | 0.0 |

Example 9-1: Hydrophobic Interaction Chromatography Measurement of Calicheamicin ADCs A bioconjugate according to the invention was diluted to 1 mg/mL in PBS and loaded (10 μL) on Butyl HIC NPR column (4.6 mm ID×3.5 cm L, 2.5 μm, Tosoh biosciences). The column was rinsed with 2M ammonium sulfate in 50 mM sodium phosphate buffer pH 6. A 13 min gradient was performed to reach 100% buffer B (50 mM sodium phosphate pH 6 with 20% isopropanol) at a flow rate of 0.8 mL/min. Native trastuzumab was used as a reference and calculate relative retention times. The results are presented in Table 6 below.

TABLE 6

HIC retention times (r.t.) and relative retention times (r.r.t.)

| Conjugate | DAR | r.t. (min) | r.r.t |
|---|---|---|---|
| trastuzumab | | 6.49 | |
| ADC211 | 2 | 6.88 | 1.06 |
| ADC212 | 2 | 6.87 | 1.06 |
| ADC213 | 2 | 6.90 | 1.06 |
| ADC214 | 2 | 6.91 | 1.06 |
| ADC215 | 2 | 6.99 | 1.08 |
| ADC216 | 2 | 6.97 | 1.07 |
| ADC217 | 2 | 6.69 | 1.03 |
| ADC218 | 2 | 6.99 | 1.08 |
| ADC219 | 2 | 6.90 | 1.06 |
| ADC220 | 2 | 6.94 | 1.07 |
| ADC221 | 2 | 7.00 | 1.08 |
| ADC222 | 2 | 6.78 | 1.04 |
| ADC224 | 2 | 6.60 | 1.02 |
| ADC246 | 2 | 6.76 | 1.04 |
| ADC247 | 2 | 6.75 | 1.04 |
| ADC249 | 2 | 6.91 | 1.06 |
| ADC250 | 4 | 7.81 | 1.20 |

The invention claimed is:

1. An enediyne-glycoprotein conjugate according to general structure:

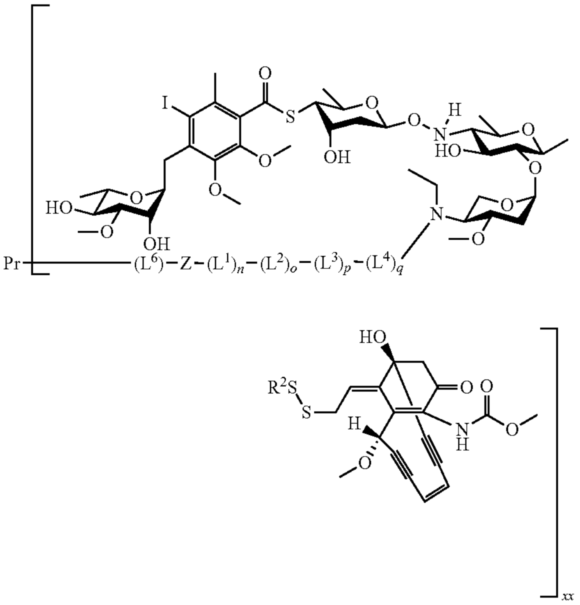

wherein:

Pr is an antibody;

Z is a connecting group that is formed in a click reaction between a (hetero)cycloalkyne moiety and a 1,3-dipole;

$L^6$ is a linker that links Z to Pr, wherein $L^6$ is GlcNAc $(Fuc)_w$¬-S-$(L^7)_{w'}$-, wherein GlcNAc is N-acetylglucosamine, Fuc is fucose, w is 0 or 1, S is a monosaccharide, $L^7$ is —N(H)C(O)$CH_2$—, —N(H)C(O)$CF_2$— or —$CH_2$—, and w' is 0 or 1;

n, o, p, and q are each individually 0 or 1, provided that n+o+p+q=1, 2, 3 or 4, xx is an integer in the range 1-8, $R^2$ is —S($C_1$-$C_{10}$ alkyl) or —C($R^6$)$_2R^7$, wherein each $R^6$ is independently selected from H or optionally substituted $C_1$-$C_6$ alkyl and $R^7$ is selected from H, $C_1$-$C_{12}$ alkyl, -$L^5$-$OR^8$, $(CH_2)_s$O-$L^5$-$OR^8$ and $(CH_2)_s$C(O)$NR^{29}$-$L^5$-$OR^8$, wherein $L^5$ is a linker having 1-100 optionally substituted backbone atoms selected from C, N, O and S, $R^8$ is H or methyl, s=1, 2 or 3 and $R^{29}$ is selected from H and -$L^5$-$OR^8$;

$L^1$ is a linker represented by -$(W)_k$-$(A)_d$-$(B)_e$-$(A)_f$-$(B)_g$—C(O)—, wherein:

k=0 or 1 with the proviso that if k=1 then d=0;

d=0 or 1;

e=an integer in the range 1-10;

f=0 or 1;

g=an integer in the range 0-10;

W is —OC(O)—, —C(O)O—, —C(O)NH—, —NHC(O)—, —OC(O)NH—, —NHC(O)O—, —C(O)$(CH_2)_m$C(O)—, —C(O)$(CH_2)_m$C(O)NH— or -(4-Ph)$CH_2$NHC(O)$(CH_2)_m$C(O)NH—, wherein m is an integer in the range 0-10;

A is a sulfamide group according to structure (23):

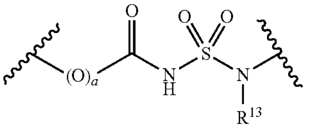

(23)

wherein a=0 or 1, and $R^{13}$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^{14}$ wherein $R^{14}$ is independently selected from the group consisting of hydrogen and $C_1$-$C_4$ alkyl groups, or $R^{13}$ is connected to an enediyne moiety via a spacer moiety;

B is a —$CH_2$—$CH_2$—O— or a —O—$CH_2$—$CH_2$— moiety, or $(B)_e$ is a —$(CH_2$—$CH_2$—$O)_{e1}$—$CH_2$—$CH_2$— moiety, wherein e1 is defined the same way as e;

$L^2$ is a peptide spacer;

$L^3$ is a self-immolative para-aminobenzyloxycarbonyl (PABC) derivative according to structure (25):

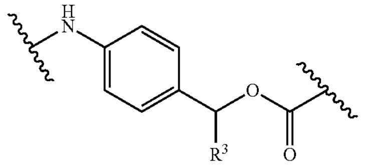

(25)

wherein $R^3$ is H, $R^4$ or C (O) $R^4$, wherein $R^4$ is $C_1$-$C_{24}$ (hetero)alkyl groups, $C_3$-$C_{10}$ (hetero)cycloalkyl groups, $C_2$-$C_{10}$ (hetero)aryl groups, $C_3$-$C_{10}$ alkyl(hetero)aryl groups and $C_3$-$C_{10}$ (hetero)arylalkyl groups, which are optionally substituted and optionally interrupted by one or more heteroatoms selected from O, S and $NR^5$ wherein $R^5$ is independently selected from the group consisting of hydrogen and $C_1$-$C_4$ alkyl groups; and $L^4$ is an aminoalkanoic acid spacer according to the structure —N—($C_x$-alkylene)-C(O)—, wherein x is an integer in the range 1-10; or linker $L^4$ is a an ethyleneglycol spacer according to the structure —N—$(CH_2$—$CH_2$—$O)_{e6}$—$(CH_2)_{e7}$—C(O)—, wherein e6 is an integer in the range 1-10 and e7 is an integer in the range 1-3.

2. The enediyne-glycoprotein conjugate according to claim 1, wherein the GlcNAc$(Fuc)_w$¬ moiety is directly bonded to the peptide chain of the antibody.

3. The enediyne-glycoprotein conjugate according claim 1, wherein Z is a connecting group that is formed by reaction between a click probe F on a modified antibody and a click probe Q on a compound according to structure (15):

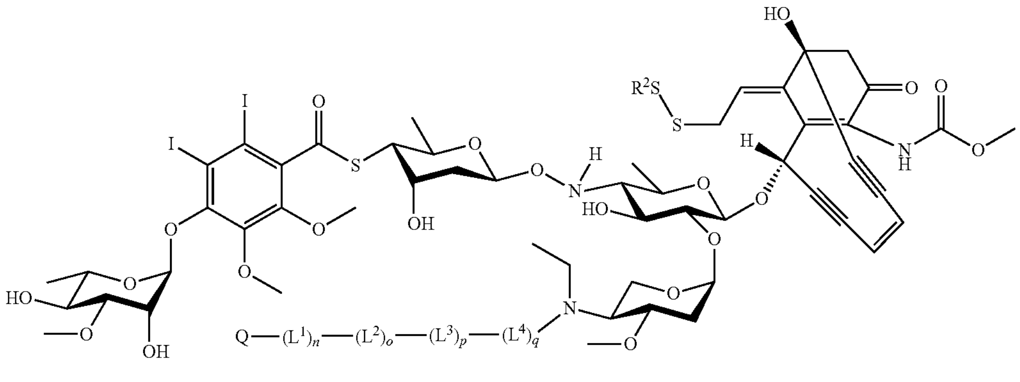

(15)

wherein $L^1$, $L^2$, $L^3$ and $L^4$ are each individually linkers that together link Q to $NR^{12}$;

n, o, p, and q are each individually 0 or 1, provided that n+o+p+q=1, 2, 3 or 4, $R^2$ is —S($C_1$-$C_{10}$ alkyl) or —C($R^6$)$_2R^7$, wherein each $R^6$ is independently selected from H or optionally substituted $C_1$-$C_6$ alkyl and $R^7$ is selected from H, $C_1$-$C_{12}$ alkyl, -$L^5$-$OR^8$, $(CH_2)_sO$-$L^5$-$OR^8$ and $(CH_2)_sC(O)NR^{29}$-$L^5$-$OR^8$, wherein $L^5$ is a linker having 1-100 optionally substituted backbone atoms selected from C, N, O and S, $R^8$ is H or methyl, s=1, 2 or 3 and $R^{29}$ is selected from H and -$L^5$-$OR^8$;

Q is the (hetero)cycloalkyne moiety;

$L^1$ is a linker represented by $-(W)_k-(A)_d-(B)_e-(A)_f(B)_g-C(O)-$, wherein:

d=0 or 1;

e=an integer in the range 1-10;

f=0 or 1;

g=an integer in the range 0-10;

k=0 or 1 with the proviso that if k=1 then d=0;

A is a sulfamide group according to structure (23):

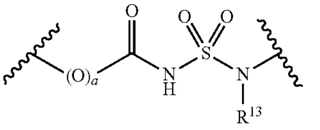

(23)

wherein a=0 or 1, and $R^{13}$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^{14}$ wherein $R^{14}$ is independently selected from the group consisting of hydrogen and $C_1$-$C_4$ alkyl groups, or $R^{13}$ is connected to an enediyne moiety via a spacer moiety;

B is a $-CH_2-CH_2-O-$ or a $-O-CH_2-CH_2-$ moiety, or (B) e is a $-(CH_2-CH_2-O)_{e1}-CH_2-CH_2-$ moiety, wherein e1 is defined the same way as e;

W is $-OC(O)-$, $-C(O)O-$, $-C(O)NH-$, $-NHC(O)-$, $-OC(O)NH-$, $-NHC(O)O-$, $-C(O)(CH_2)_m C(O)-$, $-C(O)(CH_2)_mC(O)NH-$ or $-(4\text{-}Ph)CH_2NHC(O)(CH_2)_mC(O)NH-$, wherein m is an integer in the range 0-10;

$L^2$ is a peptide spacer;

$L^3$ is a self-immolative para-aminobenzyloxycarbonyl (PABC) derivative according to structure (25):

(25)

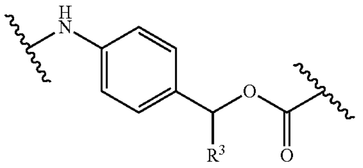

wherein $R^3$ is H, $R^4$ or $C(O)R^4$, wherein $R^4$ is $C_1$-$C_{24}$ (hetero)alkyl groups, $C_3$-$C_{10}$ (hetero)cycloalkyl groups, $C_2$-$C_{10}$ (hetero)aryl groups, $C_3$-$C_{10}$ alkyl(hetero)aryl groups and $C_3$-$C_{10}$ (hetero)arylalkyl groups, which are optionally substituted and optionally interrupted by one or more heteroatoms selected from O, S and $NR^5$ wherein $R^5$ is independently selected from the group consisting of hydrogen and $C_1$-$C_4$ alkyl groups; and $L^4$ is an aminoalkanoic acid spacer according to the structure $-N-(C_x\text{-alkylene})-C(O)-$, wherein x is an integer in the range 1-10; or linker $L^4$ is a an ethyleneglycol spacer according to the structure $-N-(CH_2-CH_2-O)_{e6}-(CH_2)_{e7}-C(O)-$, wherein e6 is an integer in the range 1-10 and e7 is an integer in the range 1-3.

4. The enediyne-glycoprotein conjugate according to claim 1, wherein the (hetero)cycloalkyne moiety is selected from the group consisting of bicyclononyne (BCN), azadibenzocyclooctyne (DIBAC/DBCO) and dibenzocyclooctyne (DIBO), and the 1,3-dipole is an azide.

5. The enediyne-glycoprotein conjugate according to claim 1, wherein Z comprises a triazole moiety.

6. The enediyne-glycoprotein conjugate according to claim 1, wherein $R^2$ is selected from $-SCH_3$, $C_1$-$C_8$ alkyl, $C(CH_3)_2CH_2CH_2OR^8$, $C(CH_3)_2CH_2CH_2C(O)OH$, $C(CH_3)_2CH_2CH_2C(O)-NHR^{27}$, wherein $R^{27}=R^8$, $(B')_h-H$, $-(B')_i-S(O)_2NHC(O)NH-(B')_h-H$, wherein $R^8$ is as defined in claim 1, B' is a $-CH_2-CH_2\text{-}O-$ moiety, h is an integer in the range 0-24 and i is an integer in the range 0-4.

7. The enediyne-glycoprotein conjugate according to claim 1, wherein $R^2$ is selected from:

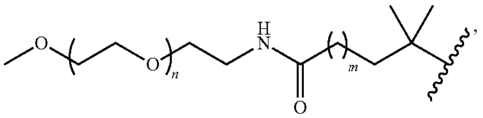

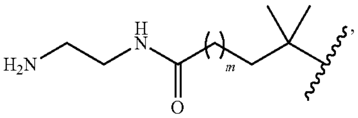

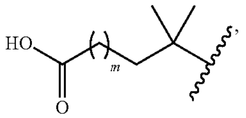

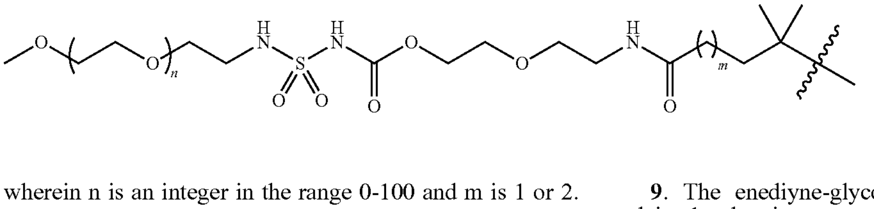

wherein n is an integer in the range 0-100 and m is 1 or 2.

8. The enediyne-glycoprotein conjugate according to claim 7, wherein in $R^2$, n is an integer in the range 1-100, and m is 1.

9. The enediyne-glycoprotein conjugate according to claim 1, wherein n=o=p=1 or n=1 and o=p=0.

10. The enediyne-glycoprotein conjugate according to claim 1, selected from the group consisting of compounds (Xz)-(XXIVz):

(Xz)
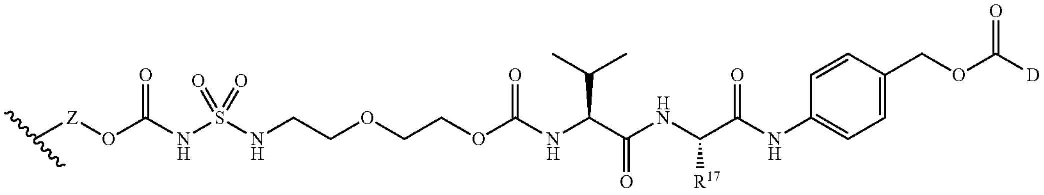
(XIz)
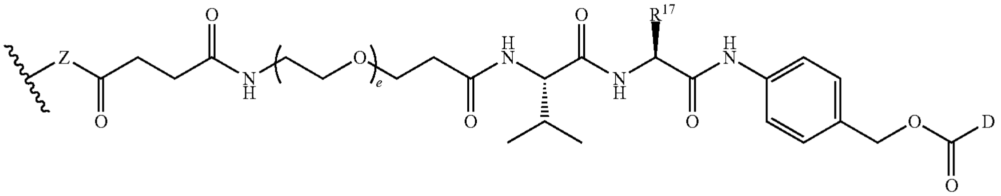
(XIIz)
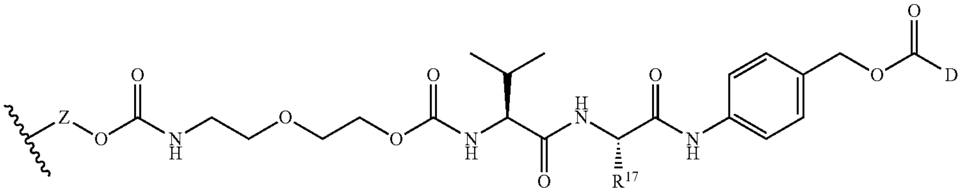
(XIIIz)
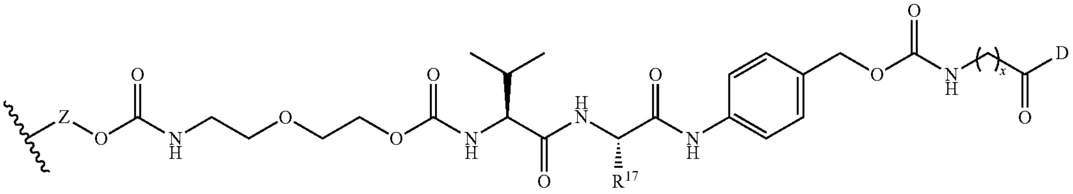
(XIVz)
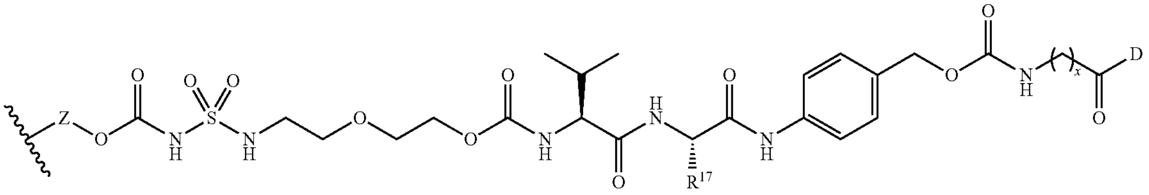
(XVz)
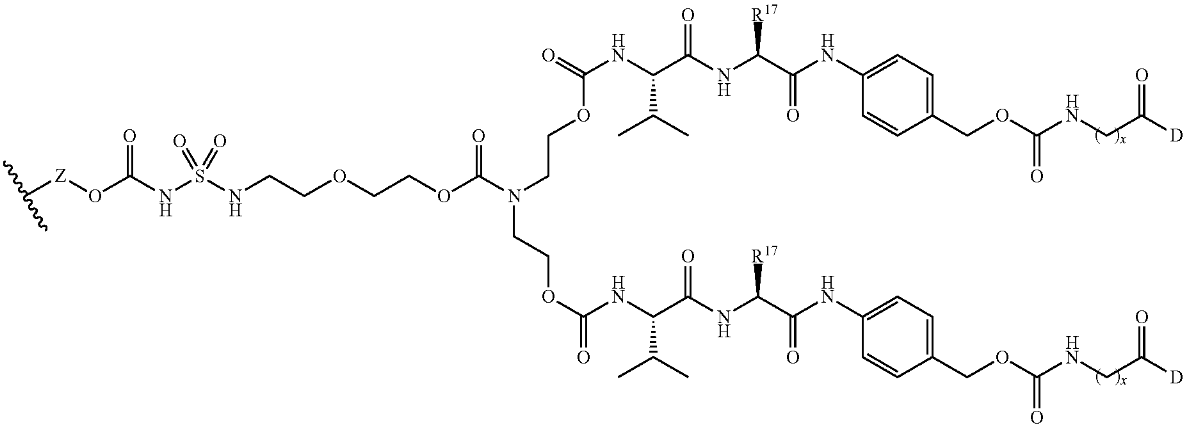

-continued
(XVIz)
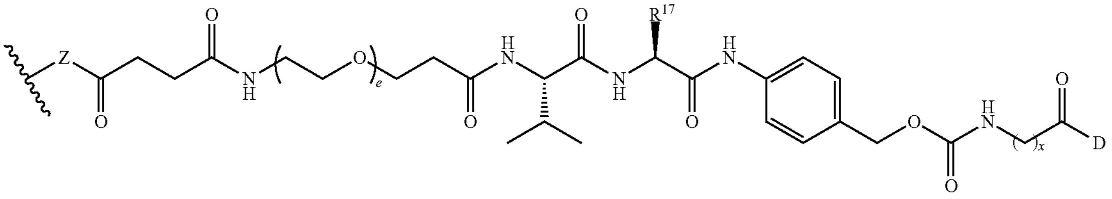
(XVIIz)
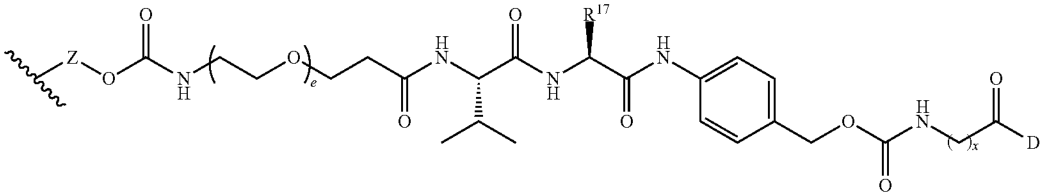
(XVIIIz)
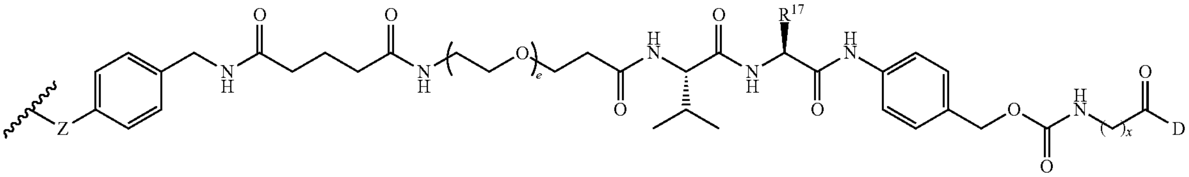
(XIXz)
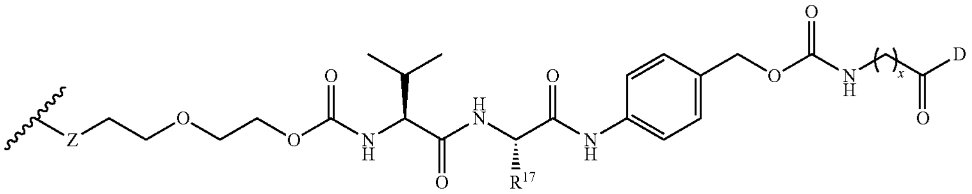
(XX)
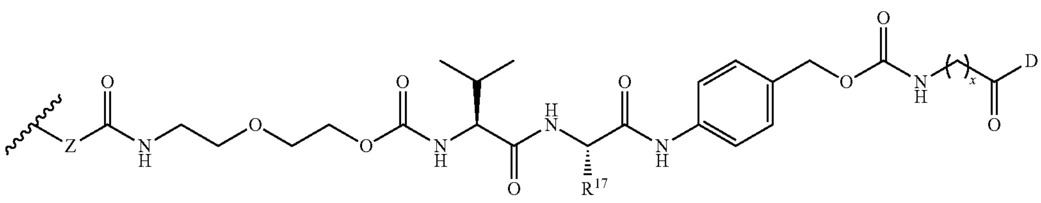
(XXIz)
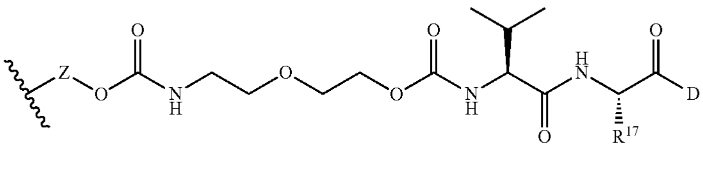

-continued (XXIIz)

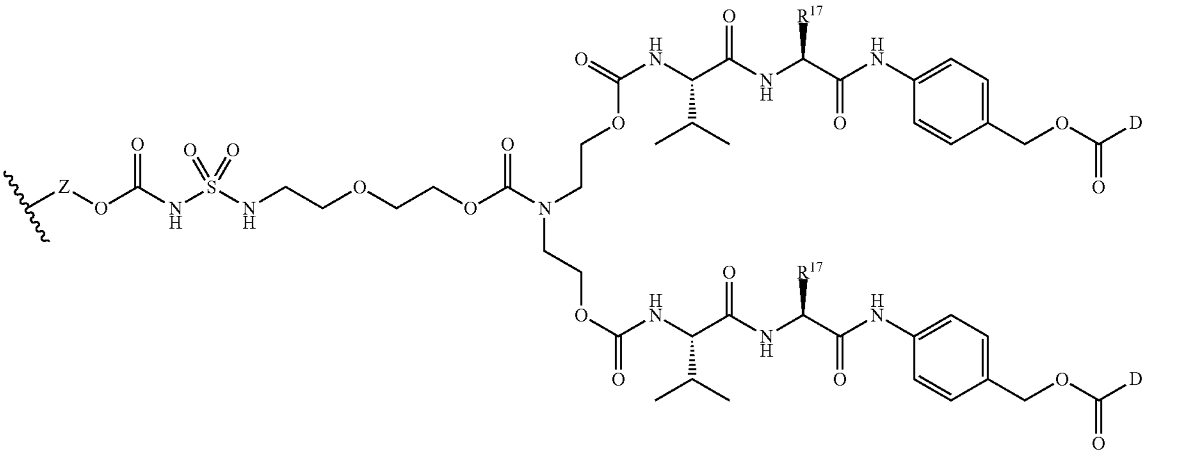

(XXIIIz)

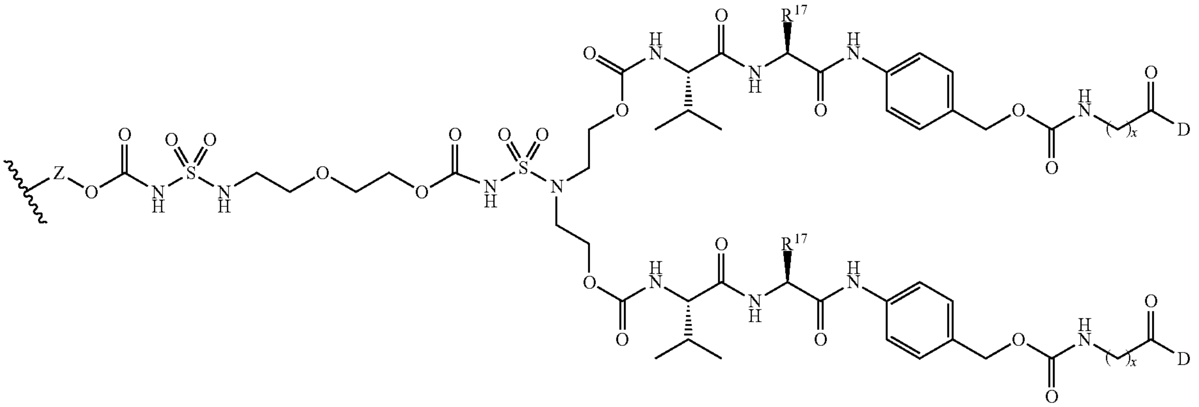

(XXIVz)

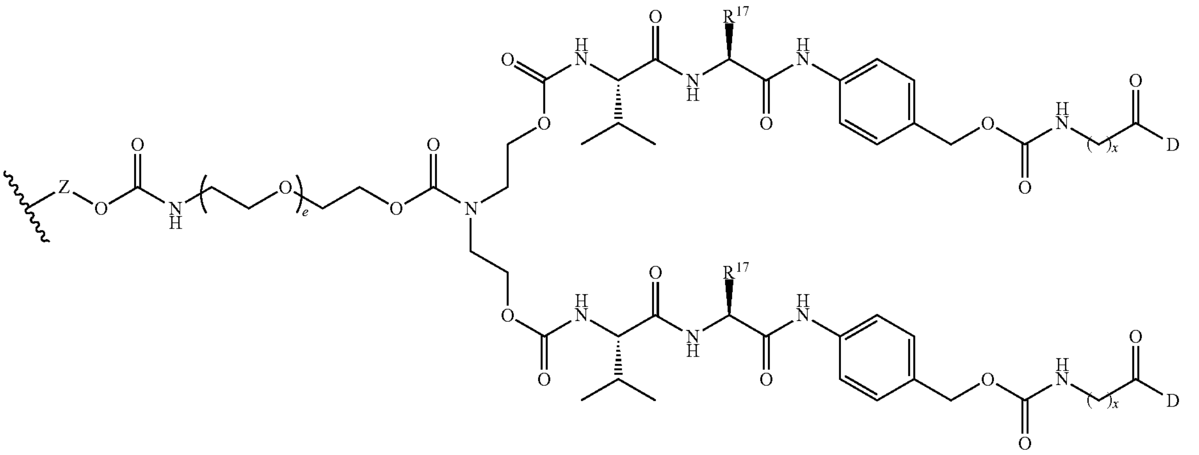

wherein:

$R^{17}$ is $CH_3$ or $CH_2CH_2CH_2NHC(O)NH_2$;

x is an integer in the range of 1 to 20;

e is an integer in the range of 0-10;

the wavy line represents the connection to ($L^6$);

D is the enediyne moiety connected via $NCH_2CH_3$.

11. A pharmaceutical composition comprising the enediyne-glycoprotein conjugate according to claim 1 and a pharmaceutically acceptable carrier.

12. A method of treating cancer in a subject in need thereof, comprising administering to the subject the enediyne-glycoprotein conjugate according to claim 1.

13. An enediyne compound of structure (15):

(15)

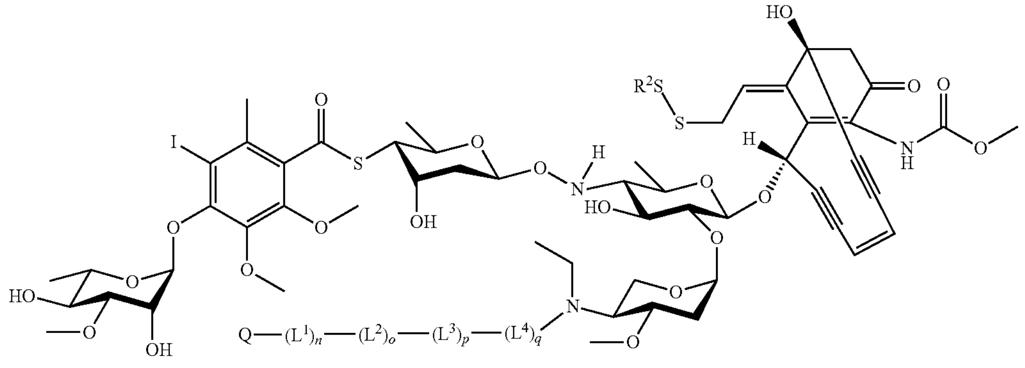

wherein:

Q is a click probe;

n, o, p, and q are each individually 0 or 1, provided that n+o+p+q=1, 2, 3 or 4, $R^2$ is —S($C_1$-$C_{10}$ alkyl) or —C($R^6$)$_2$$R^7$, wherein each $R^6$ is independently selected from H or optionally substituted $C_1$-$C_6$ alkyl and $R^7$ is selected from H, $C_1$-$C_{12}$ alkyl, -$L^5$-$OR^8$, $(CH_2)_s$O-$L^5$-$OR^8$ and $(CH_2)_s$C(O)$NR^{29}$-$L^5$-$OR^8$, wherein $L^5$ is a linker having 1-100 optionally substituted backbone atoms selected from C, N, O and S, $R^8$ is H or methyl, s=1, 2 or 3 and $R^{29}$ is selected from H and -$L^5$-$OR^8$;

$L^1$ is a linker represented by-$(W)_k$-$(A)_d$-$(B)_e$-$(A)_f$$(B)_g$-C(O)-, wherein:

k=0 or 1 with the proviso that if k=1 then d=0;

d=0 or 1;

e=an integer in the range 1-10;

f=0 or 1;

g=an integer in the range 0-10;

W is —OC(O)—, —C(O)O—, —C(O)NH—, —NHC(O)—, —OC(O)NH—, —NHC(O)O—, —C(O)$(CH_2)_m$C(O)-, —C(O)$(CH_2)_m$C(O)NH— or —(4-Ph)$CH_2$NHC(O)(CH2)$_m$C(O)NH—, wherein m is an integer in the range 0-10;

A is a sulfamide group according to structure (23):

(23)

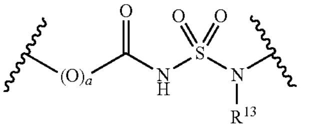

wherein a =0 or 1, and $R^{13}$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$—$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$—$C_{24}$ (hetero)arylalkyl groups optionally substituted and optionally interrupted by one or more heteroatoms selected from O, S and $NR^{14}$ wherein $R^{14}$ is independently selected from the group consisting of hydrogen and $C_1$-$C_4$ alkyl groups, or $R^{13}$ is connected to an enediyne moiety via a spacer moiety;

B is a —$CH_2$-$CH_2$—O—or a —O-$CH_2$-$CH_2$-moiety, or $(B)_e$ is a -$(CH_2$-$CH_2$-$O)_{e1}$-$CH_2$- $CH_2$-moiety, wherein e1 is defined the same way as e;

$L^2$ is a peptide spacer;

$L^3$ is a self-immolative para-aminobenzyloxycarbonyl (PABC) derivative according to structure (25):

(25)

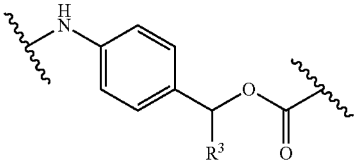

wherein $R^3$ is H, $R^4$ or C (O)$R^4$, wherein $R^4$ is $C_1$-$C_{24}$ (hetero)alkyl groups, $C_3$-$C_{10}$ (hetero)cycloalkyl grou.ps, $C_2$-$C_{10}$ (hetero)aryl groups, $C_3$-$C_{10}$ alkyl(hetero)aryl groups and $C_3$-$C_{10}$ (hetero)arylalkyl groups, which are optionally substituted and optionally interrupted by one or more heteroatoms selected from O, S and $NR^5$ wherein $R^5$ is independently selected from the group consisting of hydrogen and $C_1$-$C_4$ alkyl groups;

$L^4$ is an aminoalkanoic acid spacer according to the structure -N-($C_x$-alkylene)—C(O)—, wherein x is an integer in the range 1-10; or linker $L^4$ is a an ethyleneglycol spacer according to the structure-N-$(CH_2$-$CH_2$-$O)_{e6}$- $(CH_2)_{e7}$-C(O)-, wherein e6 is an integer in the range 1-10 and e7 is an integer in the range 1-3.

14. The enediyne-glycoprotein conjugate according to claim 1, wherein:

n=1 and $L^1$ is present, wherein k=0, d=1, e=1, 2, 3 or 4, f=0 and g=1, and wherein A is according to structure (23), (23)

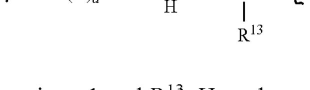

wherein a=1 and $R^{13}$=H, and

B=—$CH_2$—$CH_2$—O—;

o=1 and $L^2$ is a dipeptide or a tripeptide;

p=1 and $L^3$ is according to structure (25), (25)

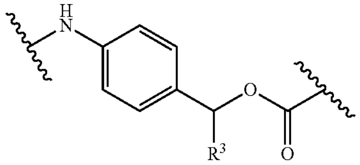

wherein $R^3$=H;

within $L^6$, S=GalNAc, w'=0 and the GlcNAc(Fuc)$_w$- moiety is directly bonded to the peptide chain of the antibody;

Z is a connecting group that is formed in a click reaction between the (hetero)cycloalkyne according to structure (9f) and an azide;

(9f)

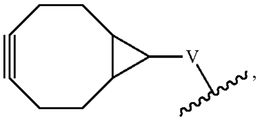

wherein V=$CH_2$.

15. The enediyne-glycoprotein conjugate according to claim 14, wherein:

e=1;

o=1 and $L^2$=Val-Cit, Val-Ala or Ala-Ala-Asn;

q=o or q=1 and $L^4$ is an aminoalkanoic acid spacer according to the structure —N—($C_x$-alkylene)-C(O)—, wherein x=1 or 6.

16. The enediyne compound according to claim 13, wherein Q is a (hetero)cycloalkyne according to structure (9f)

(9f)

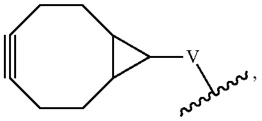

wherein V=$CH_2$.

* * * * *